(12) United States Patent
Bonny

(10) Patent No.: US 8,981,052 B2
(45) Date of Patent: Mar. 17, 2015

(54) JNK INHIBITOR MOLECULES

(75) Inventor: Christophe Bonny, Lausanne (CH)

(73) Assignee: Xigen Inflammation Ltd., Limassol (CY)

( * ) Notice: Subject to any disclaimer, the term of this patent is extended or adjusted under 35 U.S.C. 154(b) by 0 days.

(21) Appl. No.: 13/805,758

(22) PCT Filed: Jun. 21, 2011

(86) PCT No.: PCT/EP2011/003074
§ 371 (c)(1),
(2), (4) Date: Mar. 11, 2013

(87) PCT Pub. No.: WO2011/160827
PCT Pub. Date: Dec. 29, 2011

(65) Prior Publication Data
US 2013/0172530 A1 Jul. 4, 2013

(30) Foreign Application Priority Data
Jun. 21, 2010 (WO) ................ PCT/EP2010/003729

(51) Int. Cl.
*C07K 7/06* (2006.01)
*C07K 7/08* (2006.01)
*C07K 14/47* (2006.01)
*C07K 14/00* (2006.01)
*C07K 16/44* (2006.01)

(52) U.S. Cl.
CPC ............. *C07K 7/06* (2013.01); *C07K 14/4702* (2013.01); *C07K 7/08* (2013.01); *C07K 14/001* (2013.01); *C07K 16/44* (2013.01)
USPC ........ 530/324; 530/326; 530/327; 530/387.9; 424/185.1

(58) Field of Classification Search
CPC .......... C07K 7/06; C07K 7/08; C07K 14/001; C07K 14/4702
USPC ............. 530/324, 326, 327, 387.9; 424/185.1
See application file for complete search history.

(56) References Cited

U.S. PATENT DOCUMENTS

| | | |
|---|---|---|
| 4,631,211 A | 12/1986 | Houghten |
| 4,698,327 A | 10/1987 | Nagarajan et al. |
| 4,732,890 A | 3/1988 | Bonelli et al. |
| 5,169,933 A | 12/1992 | Anderson et al. |
| 5,597,895 A | 1/1997 | Gaynor et al. |
| 5,670,617 A | 9/1997 | Frankel et al. |
| 5,672,479 A | 9/1997 | Johnson et al. |
| 5,674,980 A | 10/1997 | Frankel et al. |
| 5,686,264 A | 11/1997 | Gaynor et al. |
| 5,747,641 A | 5/1998 | Frankel et al. |
| 5,756,684 A | 5/1998 | Johnson et al. |
| 5,804,604 A | 9/1998 | Frankel et al. |
| 5,840,313 A | 11/1998 | Vahlne et al. |
| 5,880,261 A | 3/1999 | Waeber et al. |
| 5,989,814 A | 11/1999 | Frankel et al. |
| 5,994,108 A | 11/1999 | Gaynor et al. |
| 5,994,109 A | 11/1999 | Woo et al. |
| 6,043,083 A | 3/2000 | Davis et al. |
| 6,117,632 A | 9/2000 | O'Mahony |
| 6,265,386 B1 | 7/2001 | Campbell |
| 6,284,456 B1 | 9/2001 | Jones et al. |
| 6,300,317 B1 | 10/2001 | Szoka et al. |
| 6,316,003 B1 | 11/2001 | Frankel et al. |
| 6,348,185 B1 | 2/2002 | Piwnica-Worms |
| 6,420,031 B1 | 7/2002 | Parthasarathy et al. |
| 6,448,283 B1 | 9/2002 | Ylikoski et al. |
| 6,495,663 B1 | 12/2002 | Rothbard et al. |
| 6,586,403 B1 | 7/2003 | Mathison et al. |
| 6,610,820 B1 | 8/2003 | Bonny |
| 6,630,351 B1 | 10/2003 | Monahan et al. |
| 6,653,443 B2 | 11/2003 | Zhang et al. |
| 6,673,908 B1 | 1/2004 | Stanton, Jr. |
| 6,740,524 B1 | 5/2004 | Akuta et al. |
| 6,780,970 B2 | 8/2004 | Bonny |
| 6,881,825 B1 | 4/2005 | Robbins et al. |
| 6,960,648 B2 | 11/2005 | Bonny |
| 7,034,109 B2 | 4/2006 | Bonny |
| 7,148,215 B2 | 12/2006 | Ratcliffe et al. |
| 7,166,692 B2 | 1/2007 | Karas |
| 7,635,681 B2 | 12/2009 | Bonny |
| 7,943,574 B2 | 5/2011 | Bonny |
| 8,236,924 B2 | 8/2012 | Bonny |
| 8,278,413 B2 | 10/2012 | Bonny |
| 2002/0042423 A1 | 4/2002 | Richert et al. |
| 2002/0103229 A1 | 8/2002 | Bhagwat et al. |

(Continued)

FOREIGN PATENT DOCUMENTS

| | | |
|---|---|---|
| EP | 0375040 | 12/1989 |
| EP | 0 679 716 A1 | 11/1995 |
| EP | 0 897 002 A2 | 2/1999 |
| EP | 1 364 949 A1 | 11/2003 |
| JP | 58-146538 | 9/1983 |
| JP | 02-221294 | 4/1990 |
| JP | 2-221294 | 9/1990 |
| WO | 92-18138 A1 | 10/1992 |
| WO | 93-18759 A1 | 9/1993 |
| WO | 94-04562 A1 | 3/1994 |

(Continued)

OTHER PUBLICATIONS

Nori, Aparna and Kopecek, Jindrich—Intracellular Targeting of Polymer-Bound Drugs for Cancer Chemotherapy—Advanced Drug Delivery Reviews—Dec. 24, 2004—pp. 609-636—vol. 57—ScienceDirect—Elsevier B.V.—The Netherlands.

(Continued)

*Primary Examiner* — Julie Ha
(74) *Attorney, Agent, or Firm* — Morgan Lewis & Bockius LLP

(57) ABSTRACT

JNK inhibitor molecules are described. In addition, methods for raising antibodies against such JNK inhibitor molecules are disclosed. These antibodies and cells producing these antibodies are also described.

15 Claims, 32 Drawing Sheets

(56) References Cited

U.S. PATENT DOCUMENTS

Figure 1A:
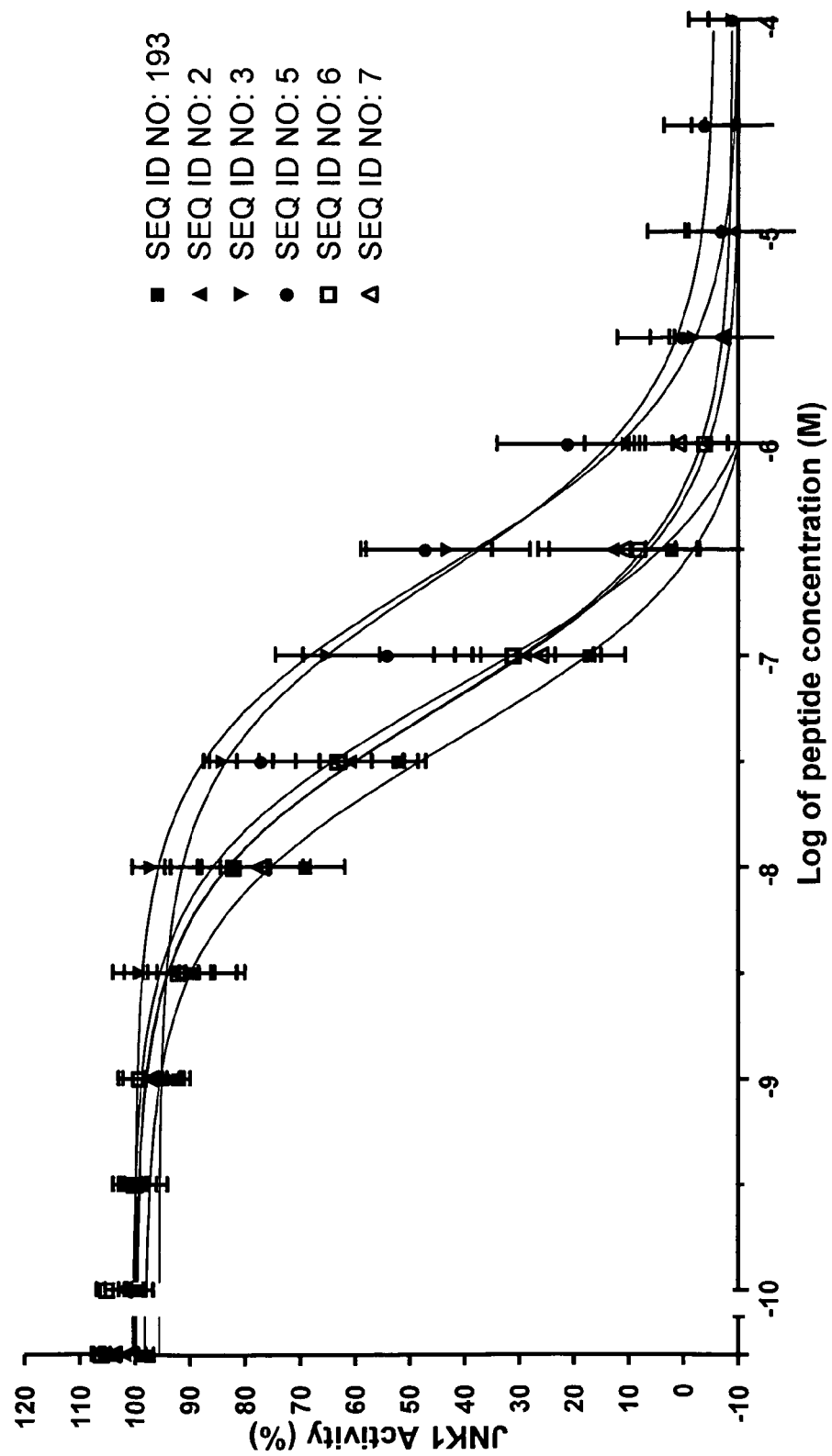

| | | |
|---|---|---|
| 2003/0100549 A1 | 5/2003 | Salituro et al. |
| 2003/0104622 A1 | 6/2003 | Robbins et al. |
| 2003/0108539 A1 | 6/2003 | Bonny |
| 2003/0124113 A1 | 7/2003 | Hillman et al. |
| 2003/0220480 A1 | 11/2003 | Bonny |
| 2004/0058875 A1 | 3/2004 | Gamache |
| 2004/0082509 A1 | 4/2004 | Bonny |
| 2004/0265879 A1 | 12/2004 | Iversen et al. |
| 2005/0059597 A1 | 3/2005 | Tymianski |
| 2005/0106695 A1 | 5/2005 | Bonny |
| 2006/0223807 A1 | 10/2006 | Davis et al. |
| 2006/0258706 A1 | 11/2006 | Saindane |
| 2006/0270646 A1 | 11/2006 | Graczyk et al. |
| 2007/0003531 A1 | 1/2007 | Mukherji et al. |
| 2007/0060514 A1 | 3/2007 | Bonny |
| 2008/0008749 A1 | 1/2008 | Pearlman et al. |

FOREIGN PATENT DOCUMENTS

| | | |
|---|---|---|
| WO | 94-04686 | 3/1994 |
| WO | 94-05311 A1 | 3/1994 |
| WO | 94-23751 A1 | 10/1994 |
| WO | 95-34295 | 12/1995 |
| WO | 96/34093 | 10/1996 |
| WO | 97-05265 | 2/1997 |
| WO | 97-10836 | 3/1997 |
| WO | 98-11907 | 3/1998 |
| WO | 98-23781 A1 | 6/1998 |
| WO | 98-44106 A1 | 10/1998 |
| WO | 98-47913 A1 | 10/1998 |
| WO | 98-49188 | 11/1998 |
| WO | 98-51325 A2 | 11/1998 |
| WO | 98-51825 A1 | 11/1998 |
| WO | 98-52614 | 11/1998 |
| WO | 99-07728 A2 | 2/1999 |
| WO | 99-16787 A1 | 4/1999 |
| WO | 99-49879 | 10/1999 |
| WO | 99-50282 A2 | 10/1999 |
| WO | 99-58561 A1 | 11/1999 |
| WO | 99-67284 A2 | 12/1999 |
| WO | 00-12587 A2 | 3/2000 |
| WO | 00-41719 A1 | 7/2000 |
| WO | 01-10888 A1 | 2/2001 |
| WO | 01-13957 A2 | 3/2001 |
| WO | 01-15511 A2 | 3/2001 |
| WO | 01-27268 | 4/2001 |
| WO | 01/39784 | 6/2001 |
| WO | 01/82975 | 11/2001 |
| WO | 02-31109 A2 | 4/2002 |
| WO | 02/32437 | 4/2002 |
| WO | 02-061105 A2 | 8/2002 |
| WO | 02-062396 A2 | 8/2002 |
| WO | 02-065986 A2 | 8/2002 |
| WO | 02-069930 A1 | 9/2002 |
| WO | 02-081504 A2 | 10/2002 |
| WO | 02-081505 A2 | 10/2002 |
| WO | 03/008553 | 1/2003 |
| WO | 03/057725 | 7/2003 |
| WO | 03-075917 A1 | 9/2003 |
| WO | 03-103698 A1 | 12/2003 |
| WO | 03-103718 A2 | 12/2003 |
| WO | 03/106491 | 12/2003 |
| WO | 2004-022580 A2 | 3/2004 |
| WO | 2004-035793 A1 | 4/2004 |
| WO | 2004/037196 | 5/2004 |
| WO | 2004-045535 A2 | 6/2004 |
| WO | 2004-054501 A2 | 7/2004 |
| WO | 2004-070052 A2 | 8/2004 |
| WO | 2004-092339 A2 | 10/2004 |
| WO | 2005-084158 A2 | 9/2005 |
| WO | 2005-097116 A1 | 10/2005 |
| WO | 2006/001582 | 1/2006 |
| WO | 2006/050930 | 5/2006 |
| WO | 2007-031098 A1 | 3/2007 |
| WO | 2007/031280 | 3/2007 |
| WO | 2008-028860 A1 | 3/2008 |
| WO | 2009/137602 | 11/2009 |
| WO | 2009-143864 A1 | 12/2009 |
| WO | 2009-143865 A1 | 12/2009 |
| WO | 2009/144038 | 12/2009 |
| WO | 2010/065850 | 6/2010 |
| WO | 2011/160653 A1 | 12/2011 |
| WO | 2011/160827 A2 | 12/2011 |
| WO | 2012/048721 A1 | 4/2012 |
| WO | 2012/048893 A1 | 4/2012 |
| WO | 2013/091670 | 6/2013 |
| WO | 2013/091896 | 6/2013 |

OTHER PUBLICATIONS

Okitsu et al.—Protein Transduction Domains Enable Isolated Islets to Efficiently Internalize the Target Protein—Transplantation Proceedings—Feb. 2003—p. 479—vol. 35—Elsevier Science inc.—USA.

Pan et al.—Small Peptide Inhibitor of JNKs Protects Against MPTP-Induced Nigral Dopaminergic Injury via Inhibiting the JNK-Signaling Pathway—Laboratory Investigation—Feb. 2010—pp. 156-167—vol. 90—USCAP, Inc.—USA.

Parkinson's Disease: Challenges, Progress, and Promise—Publication—National Institute of Neurological Disorders and Stroke—National Institutes of Health—2004—22 pages—No. 05-5595—<http://www.ninds.nih.gov/disorders/parkinsons_disease/parkinsons_research_pr.htm.

Penco et ai.—Identification of an Import Signal for, and the Nuclear Localization of, Human Lactoferrin—Biotechnology and Applied Biochemistry—Dec. 2001—pp. 151-159—vol. 34—Portland Press Ltd—United Kingdom.

Pennington, Michael W. and Dunn, Ben M. (Editors)—Chapter 11—Design of Novel Synthetic Peptides including Cyclic Conformationally and Topgraphically Constrained Analogs—Hruby, Victor and Bonner, G. Gregg—Methods in Molecular Biology—vol. 35—Peptide Synthesis Protocols—1994—pp. 201-239—Humana Press Inc.—USA.

Pennington, Michael W. and Dunn, Ben M. (Editors)—Chapter 12—Solid-Phase Synthesis of Peptides Containing the CH2NH Reduced Bond Surrogate—Pennington, Michael W.—Methods in Molecular Biology—vol. 35—Peptide Synthesis Protocols—1994—pp. 241-247—Humana Press Inc.—USA.

Pratner et al.—Synthesis and Characterization of a Gd-DOTA-D-Permeation Peptide for Magnetic Resonance Relaxation Enhancement of Intracellular Targets—Research Article—Massachusetts Institute of Technology—Molecular Imaging—Oct. 2003—pp. 333-341—vol. 2—No. 4—The Society of Molecular Imaging—USA.

Ramage, Robert and Epton, Roger (Editors)—Chapters 165 and 166—Guichard et al.—Chapter 167—Gur'yanov et al.—EPS—Proceedings of the Twenty-Fourth European Peptide Symposium, Sep. 8-13, 1996, Edinburgh, Scotland—pp. 447-451—The European Peptide Society—Mayflower Scientific Ltd.—United Kingdom.

Ramage, Robert and Epton, Roger (Editors)—Chapter—183—Horvath et al.—Chapter 184—Hruby et al.—EPS—Proceedings of the Twenty-Fourth European Peptide Symposium, Sep. 8-13, 1996, Edinburgh, Scotland—pp. 483-486—The European Peptide Society—Mayflower Scientific Ltd.—United Kingdom.

Ramanathan et al.—Targeting the Sodium-Dpendent Multivitamin Transporter (SMVT) for Improving the Oral Absorption Properties of a Retro-Inverso Tat Nonapeptide—Pharmaceutical Research—Jul. 2001—pp. 950-956—vol. 18—No. 7—USA.

Ribeiro et al.—Heme Oxygenase-1 Fused to a TAT Peptide Transduces and Protects Pancreatic β-Cells—BBRC—Biochemical and Biophysical Research Communications—Apr. 4, 2003—pp. 876-881—vol. 305—ScvienceDirect—Academic Press—Eleseveir Science (USA)—USA.

Rickels et al.—Phage Display Selection of Ligand Residues Important for Src Homology 3 Domain Binding Specificity—Biochemistry—Proceedings of the National Academy of Science—Nov. 1995—pp. 10909-10913—vol. 92—National Academy of Science—USA.

(56) References Cited

OTHER PUBLICATIONS

Robinson et al.—Properties and Structure-Activity Studies of Cyclic β-hairpin Peptidomimetics Based on the Cationic Antimicrobial Peptide Protegrin I—Bioorganic & Medicinal Chemistry—Jan. 7, 2005—pp. 2055-2064—vol. 13—ScienceDirect—Elsevier Ltd.—USA.
Roduit, Raphaël and Schorderet, Daniel F.—MAP Kinase Pathways in UV-Induced Apoptosis of Retinal Pigment—Epithelium ARPE19 Cells—Apoptosis—2008—pp. 343-353—DOI 10.1007/s10495-008-0179-8—Springer Science+Business Media, LLC—USA.
Rojas et al.—Controlling Epidermal Growth Factor (EGF)-Stimulated Ras Activation in Intact Cells by a Cell-Permeable Peptide Mimicking Phosphorylated EGF REceptor—Journal of Biological Chemistry—Nov. 1, 1996—pp. 27456-27461—vol. 271—No. 44—The American Society for Biochemistry and Molecular Biology, Inc.—USA.
Roy et al.—Role of the JNK Signal Transduction Pathway in Inflammatory Bowel Disease—World Journal of Gastroenterol—Jan. 14, 2008—pp. 200-202—vol. 14—No. 2—www.wjgnet.com—USA.
Ruben et al.—Structural and Functional Characterization of Human Immunodeficiency Virus tat Protein—Journal of Virology—Jan. 1989—pp. 1-8—vol. 63—No. 1—American Society for Microbiology—USA.
Rudikoff et al.—Single Amino Acid Substitution Altering Antigen-Binding Specificity—Immunology—Proceedings of the National Academy of Science—Mar. 1982—pp. 1979-1983—vol. 79—National Academy of Science—USA.
Rudinger, J.—Characteristics of the Amino Acids as Components of a Peptide Hormone Sequence—Peptide Hormones—1976—pp. 1-7—University Park Press, Baltimore—USA.
Saito, Naoyuki G. and Paterson, Yvonne—Contribution of Peptide Backbone Atoms to Binding of an Antigenic Peptide to Class 1 Major Histocompatibility Complex Module—Molecular Immunology—Nov. 13, 1997—pp. 1133-1145—vol. 34—No. 16-17—Pergamon—Elsevier Science Ltd.—United Kingdom.
Schimmer et al—The BH3 Domain of BAD Fused to the Antennapedia Peptide Induces Apoptosis via its Alpha Helical Structure and Independent of Bcl-2—Cell Death and Differentiation—Feb. 18, 2001 pp. 725-733—vol. 8—No. 7—Canada.
Schinzel, R. and Drueckes, P.—The Phosphate Recognition Site of *Escherichia coli* Maltodextrin Phosphorylase—FEBS Letters—Jul. 29, 1991—pp. 125-128—vol. 286—Nos. 1 and 2—Federation of European Biochemical Societies—Elsevier Science Publishers B.V.—The Netherlands.
Schwarze et al.—In Vivo PRotein Transduction: Delivery of a Biologically Active Protein into the Mouse—Science—Sep. 3, 1999—pp. 1569-1572—vol. 285—Science Magazine—USA.
Sebestyen et al.—DNA Vector Chemistry: The Covalent Attachment of Signal Peptides to Plasmid DNA—Research—Nature Biotechnology—Jan. 16, 1998—pp. 80-85—vol. 16—USA.
Selective Dimerisation of Cysteines to form Heterodimers—Aim—Chemistry—Procedure—NJE—Feb. 3, 1997—One Page—USA.
Smilek et al.—A Single Amino Acid Change in a Myelin Basic Protein Peptide Confers the Capacity to Prevent Rather than Induce Experimental Autoimmune Encephalomyelitis—Immunology—Proceedings of the National Academy of Science—Nov. 1, 1991—pp. 9633-9637—vol. 88—No. 21—The National Academy of Science—USA.
Stevens et al.—Efficient Generation of Major Histocompatibility Complex Class I-Peptide Complexes Using Synthetic Peptide Libraries—The Journal of Biological Chemistry—Jan. 3, 1998—pp. 2874-2884—vol. 273—No. 5—The American Society for Biochemistry and Molecular Biology, Inc.—USA.
Fischer, P.M.—The Design, Synthesis and Application of Stereochemical and Directional Peptide Isomers: A Critical Review—Current Protein and Peptide Science—2003—pp. 339-356—vol. 4—Bentham Science Publishes Ltd.—United Kingdom.

Thoren et al.—The Antennapedia Peptide Penetratin Translocates across Lipid Bilayers—The First Direct Observation—FEBS Letters—2000—pp. 265-268—No. 482—Federation of European Biochemical Societies—Elsevier Science B.V.—Europe.
Torchilin et al.—Fluorescence Microscopy to Follow the Targeting of Liposomes and Micelles to Cells and their Intracellular Fate—Advanced Drug Delivery Reviews—Jan. 2005—pp. 95-109—vol. 57—ScienceDirect Elsevier B.V.—The Netherlands.
Torgerson et al.—Regulation of NF-kappa B, AP-1, NFAT, and STAT1 Nuclear Import in T Lymphocytes by Noninvasive Delivery of Peptide Carrying the Nuclear Localization Sequence of NF-kappa B p50—Journal of Immunology—1998—pp. 6084-6092—vol. 161—The American Association of Immunologists—USA.
Touchard et al.—A Peptide Inhibitor of c-Jun N-Terminal Kinase for the Treatment of Endotoxin-Induced Uveitis—Immunology and Microbiology—Investigative Ophthalmology & Visual Science—Sep. 2010—pp. 4683-4693—vol. 51—No. 9—Association for Research in Vision and Ophthalmology—USA.
Tournier et al.—Mitogen-Activated Protein Kinase Kinase 7 is an Activator of the c-Jun NH2-Terminal Kinase—Cell Biology—Proceedings of the National Academy of Science—Jul. 1997—pp. 7337-7342—vol. 94—National Academy of Science—USA.
VAn REgenmortel et al.—D-Peptides as Immunogens and Diagnostics Reagents—Protein Engineering—Current Opinion of Biotechnology—1998—pp. 377-382—vol. 8—Current Biology Publications—France.
Vives et al.—A Truncated HIV-1 Tat Protein Basic Domain Rapidly Translocates Through the Plasma Membrane and Accumulates in the Cell Nucleus—Journal of Biological Chemistry—Jun. 20, 1997—pp. 16010-16017—vol. 272—No. 25—The American Society for Biochemistry and Molecular Biology, Inc.—USA.
Vives et al.—Structure-Activity Relationship Study of the Plasma Membrane Translocating Potential of a Short Peptide from HIV-1 Tat Protein—Letters in Peptide Science—1997—pp. 429-436—vol. 4—Kluwer Academic Publishers—The Netherlands.
Vocero-Akbani et al.—Killing HIV-Infected Cells by Transduction with an HIV Protease-Activated Caspase-3 Protein—Nature Medicine—Jan. 1999—pp. 29-33—vol. 5—No. 1—Nature America Inc.—USA.
Voet, Donald and Voet, Judith G.—Abnormal Hemoglobins—1995—pp. 235-241—Biochemsitry Second Edition—John Wiley & Sons, Inc.—USA.
Wadia et al.—Delivery of Novel Anti-Cancer Peptides by Protein Transduction Domains—Peptides—May 2004—pp. 65-69—American Pharmaceutical Review—USA.
Waldmeier et al.—Recent Clinical Failures in Parkinson's Disease with Apoptosis Inhibitors Underline the Need for a Paradigm Shift in Drug Discovery for Neurodegenerative Diseases—Biochemical Pharmacology—Nov. 15, 2006—pp. 1197-1206—vol. 72—No. 10—ScienceDirect—Elsevier Inc.—USA.
Walsh et al.—Erythrocyte Survival is Promoted by Plasma and Suppressed by a Bak-Derived BH3 Peptide that Interacts with Membrane-Associated Bcl-XL—Red Cells—Blood—May 1, 2002 pp. 3439-3448—vol. 99—No. 9—The American Society of Hematology—USA.
Wender et al.—The Design, Synthesis, and Evaluation of Molecules that Enable or Enhance Cellular Uptake: Peptoid Molecular Transporters—Proceedings of the National Academy of Science—Nov. 21, 2000—pp. 13003-13008—vol. 97—No. 24—The National Academy of Science—USA.
Whitmarsh et al.—A Mammalian Scaffold Complex thet Selectively Mediates MAP Kinase Activation—Science—Sep. 11, 1998—pp. 1671-1674—vol. 281-5383—www.sciencemag.org—USA.
Whitmarsh, A.J. and Davis, R.J.—Transcription Factor AP-1 Regulation by Mitogen-Activated Protein Kinase Signal Transduction Pathways—Review—Journal of Molecular Medicine Oct. 7, 1996—pp. 589-607—vol. 74—No. 10—Springer-Verlag—USA.
Wilson, David—Preventing Nerce Cell Death in ALS—Internet document—<http://www.als.caJ_news/57.aspx>—Dec. 5, 2001—2 pages—USA.

(56) References Cited

OTHER PUBLICATIONS

Wishart et al.—A Single Mutation Converts a Novel Phosphotyrosine Binding Domain into a Dual-specificity Phosphatase—Communication—The Journal of Biological Chemistry—Nov. 10, 1995—pp. 26782-26785—vol. 270—No. 45—The American Society for Biochemistry and Molecular Biology, Inc.—USA.

Witkowski et al.—Conversion of a 6-Ketoacyl Synthase to a Malonyl Decarboxylase by Replacement of the Active—Site Cysteine with Glutamine—Biochemistry—Aug. 18, 1999—pp. 11643-11650—vol. 38—American Chemical Society—USA.

Wyszko et al.—Interaction of Native RNAs with Tat Peptides—NATO Science Series, 3: High Technology 1999, 70 (RNA Biochemistry and Biotechnology), Sep. 9, 2002—pp. 277-290—Institute of Bioorganic Chemistry of the Polish the Polish Academy of Sciences, Poznan—Poland—Kluwer Academic Publishers—Chemical Abstracts Database Accession No. 133:204452 CA—XP002554007—Poland.

Yamamoto et al.—Molecular Design of Bioconjugated Cell Adhesian Peptide with a Water-Soluble Polymeric Modifer for Enhancement of Antimetastatic Effect—Current Drug Targets—2002—pp. 123-130—vol. 3—Bentham Science Publishers Ltd.—USA.

Yang et al.—Differential Targeting of MAP Kinases to the ETS-Domain Transcription Factor Elk-1—The EMBO Journal—1998—pp. 1740-1749—vol. 17—No. 6—European Molecular Biology Organisation—Oxford University Press—United Kingdom.

Yasuda et al.—The JIP Group of Mitogen-Activated Protein Kinase Scaffold Proteins—Molecular and Cellular Biology—Oct. 1999—pp. 7245-7254—vol. 19—No. 10—American Society for Microbiology—USA.

Zhang et al.—Preparation of Functionally Active Cell-Permeable Peptides by Single-Step Ligation of Two Peptide Modules—Proceedings of National Academy of Sciences—Biochemistry—Aug. 1998—pp. 9184-9189—vol. 95—National Academy of Sciences—USA.

Zoukhri et al.—c-Jun NH2-Terminal Kinase Mediates Interleukin-1 β-Inuced Inhibition of Lacrimal Gland Secretion—Journal of Neurochemistry—2006—pp. 126-135—vol. 96—International Society for Neurochemistry—USA.

NCBI Sequence Viewer—Accession No. AAD20443—Reports—Islet-Brain 1 (Homo sapiens)—Two References—Mooser et al.—Mar. 17, 1999—2 pages—USA.

NCBI Sequence Viewer—Accession No. AAD22543—Reports—Islet-Brain 1 (Rattus norvegicus)—Three References—Bonny et al.—Mar. 1, 2006—2 pages—USA.

NCBI Sequence Viewer—Accession No. AAF32323—Reports—Islet-Brain 2 (Homo sapiens)—Two References—Negri et al.—Feb. 9, 2000—2 pages—USA.

NCBI Sequence Viewer—Accession No. AF074091—Reports—Homo sapiens Islet-Brain 1 mRNA—Complete Cds.—Two References—Mooser et al.—Mar. 17, 1999—2 pages—USA.

NCBI Sequence Viewer—Accession No. AF108959—Reports—Rattus norvegicus Islet-Brain 1 (IB1) mRNA—Complete Cds.—Three References—Bonny et al.—Mar. 1, 2006—2 pages—USA.

NCBI Sequence Viewer—Accession No. AF218778—Reports—Homo sapiensIslet-Brain 2 mRNA—Complete Cds—Three References—Kristensen et al.—Mar. 2, 2006—2 pages—USA.

NCBI Sequence Viewer—Accession No. PH0878—Reports—Ig Kappa Chain V Region (Anti-DNA, SNA)—Human (Fragment) One Reference—Manheimer-Lory et al.—May 30, 1997—1 page—USA.

Ahmed, Shafiq Uddin and Milner, Jo—Basal Cancer Cell Survival Involves JNK2 Suppression of a Novel JNK1/c-Jun/Bcl-3 Apoptotic Network—PLoS ONE—Oct. 2009—pp. 1-13—vol. 4—Issue 10—University of York—United Kingdom.

Bowie et al., "Deciphering the message in protein sequences: tolerance to amino acid substitutions," Science, 247 (4948): 1306-1310 (1990).

Database WPI, Thompson Scientific, Accession No. 2010-M79716, 2010, 3 pages; XP002643212.

Ferrandi et al., "Inhibition of c-Jun N-terminal kinase decreases cardiomyocyte apoptosis and infarct size after myocardial ischemia and reperfusion in anaesthetized rats," British Journal of Pharmacology, 142(6): 953-960 (2004).

Hirt et al., "D-JNKI1, a cell-penetrating c-Jun-N-terminal kinase inhibitor, protects against cell death in severe cerebral ischemia," Stroke, 35(7): 1738-1743 (2004).

Kugler et al., "MAP kinase pathways involved in glioblastoma response to erucylphosphocholine," International Journal of Oncology, 25(6):1721-1727 (2004).

Stedman's Online Dictionary Definition of "inflammation", Obtained from www.pdrel.com, last viewed on Dec. 18, 2010, 2 pages.

Wang et al., "A single amino acid determines lysophospholipid specificity of the S1P1 (EDG1) and LPA1 (EDG2) phospholipid growth factor receptors," Journal of Biological Chemistry, 276(52): 49213-49220 (2001).

Wells, "Additivity of mutational effects in proteins," Biochemistry, 29(37): 8509-8517 (1990).

Tan et al., "Selective inhibition of ErbB2-overexpressing breast cancer in vivo by a novel TAT-based ErbB2-targeting signal transducers and activators of transcription 3-blocking peptide," Cancer Res. 66:3764-3772, 2008.

De Paiva et al., "Essential role for c-Jun N-terminal kinase 2 in corneal epithelial response to desiccating stress," Arch Ophthalmol., 127(12): 1625-1631, 2009.

Adele-Biassette et al.—Neuronal Apoptosis does not Correlate with Dementia in HIV Infection but is Related to Microglial Activation and Axonal Damage—Neuropathology and Applied Neurobiology—1999—pp. 123-133—vol. 25—Blackwell Science Ltd.—USA.

Adler, et al.—Regulation of JNK Signaling by GSTp—The EMBO Journal—Mar. 1, 1999—pp. 1321-1334—vol. 18—No. 5—European Molecular Biology Organization—USA.

Brady, Leo and Dodson, Guy—Reflections on a Peptide—Nature—News and Views—Drug Design—Apr. 21, 1994—pp. 692-693—vol. 368 (6473)—Nature Publishing Group—USA.

Briand et al—A Retro-Inverso Peptide Corresponding to the GH Loop of Foot-and-Mouth Disease Virus Elicits High Levels of Long-Lasting Protective Neutralizing Antibodies—Proceedings of National Academy of Sciences—Immunology—Nov. 1997—pp. 12545-12550—vol. 94—National Academy of Sciences—USA.

Brugidou et al.—The Retro-Inverso Form of a Homeobox-Derived Short Peptide is Rapidly Internalized by Cultured Neurons: A New Basis for an Efficient Intracellular Delivery System—Biochemical and Biophysical Research Communications—Sep. 14, 1995—pp. 685-693—vol. 214—No. 2—Academic Press, Inc.—USA.

Chie et al.—Identification of the Site of Inhibition of Oncogenic ras-p21-Induced Signal Transduction by a Peptide from a Ras Effector Domain—Journal of Protein Chemistry—Nov. 4, 1999—pp. 881-884—vol. 18—No. 8—USA.

Chorev et al.—a Dozen Years of Retro-Inverso Peptidomimetics—Accounts of Chemical Research—1993—pp. 266-273—vol. 26—American Chemical Society—USA.

Chorev et al.—Recent Developments in Retro Peptides and Proteins—An Ongoing Topochemical Exploration—Oct. 1995—pp. 438-445—vol. 13—No. 10—TIBTECH (Trends in Biotechnology) Elsevier Science Ltd.—USA.

Dang et al.—Nuclear and Nucleolar Targeting Sequences of c-erb-A, c-myb, N-myc, p53, HSP70, and HIV tat Proteins—Journal of Biological Chemistry—Oct. 25, 1989—pp. 18019-18023—vol. 264—No. 30—The American Society for Biochemistry and Molecular Biology, Inc.—USA.

Duby et al. (Contributors)—Using Synthetic Oligonucleotides as Probes—Current Protocols in Molecular Biology—Supplement 2—Apr. 1988—pp. 6.4.1-6.4.10—John Wiley & Sons—Document No. XP 0020444485—USA.

Elliott et al.—Intercellular Trafficking and Protein Delivery by a Herpesvirus Structural Protein—Cell—Jan. 24, 1997—pp. 223-233—vol. 88—No. 2—Cell Press—United Kingdom.

(56) References Cited

OTHER PUBLICATIONS

Frankel et al.—Activity of Synthetic Peptides from the Tat Protein of Human Immunodeficiency Virus Type 1—Proceedings of National Academy of Sciences—Biochemistry—Oct. 1989—pp. 7397-7401—vol. 86—National Academy of Sciences—USA.

Giorello et al.—Inhibition of Cancer Cell Growth and c-Myc Transcriptional Activity by a c-Myc Helix 1-Type Peptide Fused to an Internalization Sequence—Cancer Research—Aug. 15, 1998—pp. 3654-3659—vol. 58—USA.

Guichard et al.—Partially Modified Retro-Inverso Pseudopeptides as Non-Natural Ligands for the Human Class I Histocompatibility Molecule HLA-A2—Journal of Medicinal Chemistry—1996—pp. 2030-2039—vol. 39—American Chemical Society—USA.

Hauber et al.—Mutational Analysis of the Conserved Basic Domain of Human Immunodeficiency Virus tat Protein—Journal of Virology—Mar. 1989—pp. 1181-1187—vol. 63—No. 3—American Society of Microbiology—USA.

Inhibit.Dictionary.com—The American Heritage® Stedman's Medical Dictionary—Houghton Mifflin Company—One Page—Internet document: http://dictionary.reference.com/browse/inhibit—Accessed on Oct. 10, 2007—USA.

Jackson et al.—Heat Shock Induces the Release of Fibroblast Growth Factor 1 from NIH 3T3 Cells—Proceedings of National Academy of Sciences—Cell Biology—Nov. 1992—pp. 10691-10695—vol. 89—National Academy of Sciences—USA.

Jameson et al.—A Rationally Designed CD4 Analogue Inhibits Experimental Allergic Encephalomyelitis—Nature—Letters to Nature—Apr. 21, 1994—pp. 744-746—vol. 368 Nature Publishing Group—USA.

Kennedy, Norman J. and Davis, Roger J.—Perspectives: Role of JNK in Tumor Development—Cell Cycle—May/Jun. 2003—pp. 199-201—vol. 2—No. 3—www.landesbioscience.com—USA.

Kida et al.—Design and Synthesis of a Tat-related Gene Transporter: A Tool for Carrying the Adenovirus Vector into Cells—Bioorganic and Medicinal Chemistry Letters—Dec. 6, 2005—pp. 743-745—vol. 16—ScienceDirect—Elsevier Ltd—USA.

Kieber-Emmons et al.—Therapeutic Peptides and Peptidomimetics—Current Opnion in Biotechnology—1997—pp. 435-441—vol. 8—Current Biology Ltd.—USA.

Kishan, K.V. Radha and Agrawal, Vishal—SH3-like Fold Proteins are Structurally Conserved and Functionally Divergent—Current Protein and Peptide Science—1995—pp. 143-150—vol. 6—Nentham Science Publishers Ltd.—USA.

Kisselev, Lev—Polypeptide Release Factors in Prokaryotics and Eukaryotes: Same Function, Different Structure—Jan. 2002—pp. 8-9—vol. 10—Structure—Elsevier Science Ltd—USA.

Lebleu, Bernard—Delivering Information-Rich Drugs—Prospects and Challenges—Meeting Report—Apr. 1996—pp. 109-110—vol. 14—No. 4—TIBTECH (Trends in Biotechnology) Elsevier Science Ltd.—USA.

Lee et al.—c-Jun N-terminal Kinasa (JNK) Mediates Feedback Inhibition of the Insulin Signaling Cascade—The Journal of Biological Chemistry—Jan. 31, 2003—pp. 2896-2902—vol. 278—No. 5—The American Society for Biochemistry and Molecular Biology, Inc.—USA.

Lewis et al.—Lymphoma Cell Uptake of Radiometal- and Fluorescent-Labelled BCL-2 Antisense PNA Conjugates is Mediated by a Retro-Inverso Delivery Peptide—Abstracts—Journal of Label Compounds and Radiopharmaceuticals—2003—p. S13—vol. 46—SI-S403—XP-002347557—USA.

Li, Shawn S.C.—Review Article—Specificity and Versatility of SH3 and Other Ptoline-Recognition Domains: Structural Basis and Implications for Cellular Signal Transduction—Biochemical Journal—Sep. 15, 2005—pp. 641-653—Biochemical Society—vol. 390—Part 3—United Kingdom.

Lim et al.—Penetration Enhancement in Mouse Skin and Lipolysis in Adipocytes by TAT-GKH, A New Cosmetic Ingredient—Journal of Cosmetic Science—Sep./Oct. 2003—pp. 483-491—vol. 54—USA.

Lin et al.—Inhibition of Nuclear Translocation of Transcription Factor NF-kappa B by a Synthetic Peptide Containing a Cell Membrane-Permeable Motif and Nuclear Localization Sequence—Journal of Biological Chemistry—Jun. 16, 1995—pp. 14255-14258—vol. 270—No. 24—The American Society for Biochemistry and Molecular Biology, Inc.—USA.

Lloyd-Williams et al.—Chapter 5-13 Chemical Approaches to the Synthesis of Peptides and Proteins—1997—Formation of Disulfide Bridges—pp. 209-236—CRC Press LLC—USA.

Lloyd-Williams et al.—Chapter 6—Chemical Approaches to the Synthesis of Peptides and Proteins—1997—Peptides Libraries—pp. 237 and 264-267—CRC Press LLC—USA.

Mann, David A. and Frankel, Alan D.—Endocytosis and Targeting of Exogenous HIV-1 Tat Protein—The EMBO Journal—1991—pp. 1733-1739—vol. 10—No. 7—Oxford University Press—United Kingdom.

Marino et al.—Inhibition of Experimental Autoimmune Encephalomyelitis in SJL Mice by Oral Administration of Retro-Inverso Derivative of Encephalitogenic Epitope P87-99—European Journal of Immunology—1999—pp. 2560-2566—vol. 29—Wiley-VCH Verlag GmbH—Weinheim—Germany.

Marks et al.—Protein Targeting by Tyrosine- and Di-leucine-based Signals: Evidence for Distinct Saturable Components—The Journal of Cell Biology—Oct. 1, 1996—pp. 341-354—vol. 135—No. 2—The Rockefeller University Press—USA.

Mayer, Bruce J.—SH3 Domains: Complexity in Moderation—Commentary—Journal of Cell Science—Signal Transduction and Cellular Organization—Apr. 2001—pp. 1253-1263—vol. 114—The Company of Biologists Ltd—USA.

Mazur, Dan J. and Perrino, Fred W.—Identification and Expression of the TREX1 and TREX2 cDNA Sequences Encoding Mammalian 3'→5' Exonucleases—The Journal of Biological Chemistry—Jul. 9, 1999—pp. 19655-19660—vol. 274—No. 28—The American Society for Biochemistry and Molecular Biology, Inc.—USA.

Melikov, K. and Chernomordik, L.V.—Review—Arginine-rich Cell Penetrating Peptides: From Endosomal Uptake to Nuclear Delivery—Cellular and Molecular Life Sciences—Oct. 18, 2005—pp. 2739-2749—vol. 62—Birkhauser Verlag—Switzerland.

Messer, Jr., Dr. William S.—MBC 3320 Posterier Pituitary Hormones—Vasopression and Oxytocin—Apr. 30, 2000—pp. 1-5—, http://www.neurosci.pharm.utoledo.edu/MBC3320/vasopressin.htm>—USA.

Mi et al.—Characterization of a Class of Cationic Peptides able to Facilitate Efficient Protein Transduction in Vitro and in Vivo—Article—Molecular Therapy—Oct. 2000—pp. 339-347—vol. 2—No. 4—The American Society of Gene Therapy—USA.

Milano et al.—A Peptide Inhibitor of c-Jun NM2-terminal Kinase Reduces Myocardial Ischemia-reperfusion Injury and Infarct Size in Vivo—American Journal of Physiology—Heart Circulation Physiology—Apr. 2007—pp. H1828-H1835—vol. 292—www.ajpheart.org—The American Physiological Society—USA.

Mooi et al.—Regulation and Structure of an *Escherichia coli* Gene Coding for an Outer Membrane Protein involved in Export of K88ab Fimbrial Subunits—Nucleic Acids Research—1996—pp. 2443-2457—vol. 14—No. 6—IRL Press Linited—United Kingdom.

Moon et al. Bcl-2 Overexpression Attenuates SP600125-induced Apoptosis in Human Leukemia U937 Cells—Cancer Letters—Feb. 3, 2008—pp. 316-325—vol. 264—ScienceDirect—Elsevier Ireland Ltd—Ireland.

Mooser et al.—Genomic Organization, Fine-Mapping, and Expression of the Human Islet-Brain 1 (IB1)/C-Jun-Amino-Terminal Kinase Interacting Protein-1 (JIP-1) Gene—Genomics—Jan. 15, 1999—pp. 202-208—vol. 55—Academic Press—USA.

Moulin, Nathalie and Widman, Christian—Islet-Brain (IB)/JNK-Interacting Proteins (JIPs): Future Targets for the Treatment of Neurodegenerative Diseases?—Current Neurovascular Research—2004—pp. 111-127—vol. 1—No. 2—Institut de Biologie Cellulaire et de Morphologie (IBCM)—Universitéde Lusanne—Switzerland—Bentham Science Publishers Ltd.—USA.

Nagahara et al.—Transduction of Full-Length TAT Fusion Proteins into Mammalian Cells: TAT-p27Kip1 Induces Cell Migration—Nature Medicine—Dec. 1998—pp. 1449-1452—vol. 4—No. 12—Nature America Inc.—USA.

(56) References Cited

OTHER PUBLICATIONS

Negri at al.—Design of a Novel Peptide Inhibitor of the JNK Signaling Pathway—1217-P—Journal—Diabetes—Abstract Book—61st Scientific Session—Jun. 2001—p. A294—vol. 50—Supplement No. 2—American Diabetes Association—USA.
Neundorf et al.—Detailed Analysis Concerning the Biodistribution and Metabolism of Human Calcitonin-Derived Cell-Penetrating Peptides—Bioconjugate Chemistry—Jul. 24, 2008—pp. 1596-1603—vol. 19—No. 8—American Chemical Society—USA.
Ngo et al.—Computational Complexity, Protein Structure Prediction, and the Levinthal Paradox—The Protein Folding Problem and Tertiary Structure Prediction—Merz et al. (Editors)—1994—pp. 433, 492-495—Birkhauser Boston—USA.
Noguchi et al.—Regulation of c-Myc through Phosphorylation at Ser-62 and Ser-71 by c-Jun N-Terminal Kinase—Journal of Biological Chemistry—Nov. 12, 1999—pp. 32580-32587—vol. 274—No. 46—The American Society for Biochemistry and Molecular Biology, Inc.—USA.
Nori et ai.—Tat-Conjugated Synthetic Macromolecules Facilitate Cytoplasmic Drug Delivery to Human Ovarian Carcinoma Cells—Bioconjugate Chemistry—Nov. 16, 2002—pp. 44-50—vol. 14—No. 1—American Chemical Society—USA.
Bogoyevitch et al., "Taking the cell by stealth or storm? Protein transduction domains (PTDs) as versatile vectors for delivery," DNA Cell Biol., 21(12):879-894 (2002).
InVivoGen, Inc., SP600125: MAP Kinase Inhibitor—Autophagy Inhibitor—JNK inhibitor, Downloaded Jun. 9, 2014.
Kelekar et al., "Bcl-2-family proteins: the role of the BH3 domain in apoptosis," Trends Cell Biol., 8(8):324-330 (1998).
Killick et al, "Clusterin regulates β-amyloid toxicity via Dickkopf-1-driven induction of the wnt-PCP-JNK pathway," Mol Psychiatry., 19(1):88-98 (2014).
Parenteau et al.., "Free uptake of cell-penetrating peptides by fission yeast," FEBS Letters 579: 4873-4878 (2005).
Patel M. et al, "Getting into the brain—approaches to enhance brain drug delivery", CNS Drugs, v23(1):35-58 (2009).
Ahmed et al., "Basal cancer cell survival involves JNK2 suppression of a novel JNK1/c-Jun/Bcl-3 apoptotic network," PLOS ONE 4(10): e7305 (2009).
Asanuma et al., "Protection against malonate-induced ischemic brain injury in rat by a cell-permeable peptidic c-Jun N-terminal kinase inhibitor, (L)-HIV-TAT48-57-PP-JBD20, observed by the apparent diffusion coefficient mapping magnetic resonance imaging method," Neurosci Lett., 359(1-2):57-60 (2004) (only abstract).
Bost et al., "The Jun kinase 2 isoform is preferentially required for epidermal growth factor-induced transformation of human A549 lung carcinoma cells," Molecular and Cellular Biology, 19(3): 1938-1949 (1999).
Chang Lufen et al., JNK1 is required for maintenance of neuronal microtubules and controls phosphorylation of microtubule-associated proteins, Developmental Cell, 4(4): 521-533 (2003).
Hunot Stephan et al., "JNK-mediated induction of cyclooxygenase 2 is required for neurodegeneration in a mouse model of Parkinson's disease," Proceedings of the National Academy of Sciences of the United States of America,101 (2): 665-670 (2004).
Kaneto et al., "Possible novel therapy for diabetes with cell-permeable JNK-inhibitory peptide," Nature Medicine, 10 (10):1128-1132 (2004).
Kuan et al., "A critical role of neural-specific JNK3 for ischemic apoptosis," Proceedings of the National Academy of Sciences of the United States of America, 100(25): 15184-15189 (2003).
Polyakov et al., "Novel Tat-peptide chelates for direct transduction of technetium-99m and rhenium into human cells for imaging and radiotherapy" Bioconjugate Chem., 11: 762-771 (2000).
Saar et al., "Cell-penetrating peptides: a comparative membrane toxicity study," Analytical Biochemistry, 345(1):55-65 (2005).
Sabapathy, "Role of the JNK pathway in human diseases," Progress in Molecular Biology and Translational Science, 106:145-169 (2012).

Salh, "c-Jun N-terminal kinases as potential therapeutic targets," Expert Opin Ther Targets, 11(10):1339-1353 (2007).
Seki et al., "A liver full of JNK: signaling in regulation of cell function and disease pathogenesis, and clinical approaches," Gastroenterology, 143(2):307-320 (2012).
Sumara et al., "Jnking atherosclerosis," Cellular and Molecular Life Sciences, Birkhäuser Verlag, 62(21): 2487-2494 (2005).
Tachibana et al., "JNK1 is required to preserve cardiac function in the early response to pressure overload, Biochemical and Biophysical Research Communications," 343(4): 1060-1066 (2006).
Westwick et al., "Activatin of Jun kinase is an early event in hepatic regeneration," The Journal of the Clinical Investigation, 95(2): 803-810 (1995).
Aarts et al.—Treatment of Ischemia Brain Damage by Perturbing NMDA Receptor—PSD-95 Protein Interactions—Science—Oct. 25, 2002—pp. 846-850—vol. 298—www.sciencemag.org—USA.
Abaza et al.—Effects of Amino Acid Substitutions Outside an Antigenic Site on Protein Binding to Monoclonal Antibodies of Predetermined Specificity Obtained by Peptide Immunization: Demonstration with Region 94-100 (Antigenic Site 3) of Myoglobin—Journal of Protein Chemistry—1992—pp. 433-444—vol. 11—No. 5—USA.
Agrawal, Vishal and Kishan, K.V. Radha—Promiscuous Binding Nature of SH3 Domains to their Target Proteins—Protein and Peptide Letters—2002—pp. 185-193—vol. 9—No. 3—Bentham Science Publishing Ltd.—USA.
Aldrian-Herrada et al.—A Peptide Nucleic Acid (PNA) is More Rapidly Internalized in Cultured Neurons when Coupled to a Retro-Inverso Delivery Peptide. The Antisense Activity Depresses the Target mRNA and Protein in Magnocellular Oxytocin Neurons—Nucleic Acids Research—1998—pp. 4910-4916—vol. 26—No. 21—Oxford University Press—UK.
Assi et al.—The Specific JNK Inhibitor SP600125 Targets Tumour Necrosis Factorα Production and Epithelial Cell Apoptosis in Acute Murine Colitis—Immunology—2006—pp. 112-121—Blackwell Publishing Ltd.—USA.
Barr et al.—Indentification of the Critical Features of a Small Peptide Inhibitor of JNK Activity—Mar. 20, 2002—pp. 10987-10997—vol. 277—No. 13—USA.
Berendsen, Herman J.C.—A Glimpse of the Holy Grail?—Oct. 23, 1998—pp. 642-643—vol. 282—No. 5389—Science—Research Library—USA.
Bessalle et al.—All-D-Magainin: Chirality, Antimicrobial Activity and Proteolytic Resistance—FEBS Letters—Nov. 12, 1990—pp. 151-155—vol. 274—Nos. 1/2—Federation of European Biochemical Societies—Elsevier Science Publishes B.V.—The Netherlands.
Bonny et al.,—Cell-Permeable Peptide Inhibitors of JNK: Novel Blockers of Beta-Cell Death—Diabetes—Jan. 2001—pp. 77-82—vol. 50—No. 1—USA.
Bonny et al.—IB1, A JIP-1-Related Nuclear Protein Present in Insulin-Secreting Cells—Journal of Biological Chemistry—Jan. 23, 1998—pp. 1843-1846—vol. 273—No. 4—USA.
Bonny et al.—Pancreatic-Specific Expression of the Glucose Transporter Type 2 Gene: Identification of cis-Elements and Islet-Specific trans-Acting Factors—MOL ENDO—Molecular Endrocrinology—1995—pp. 1413-1426—vol. 9—No. 10—The Endocrine Society—USA.
Bonny et al.—Targeting the JNK Pathway as a Therapeutic Protective Strategy for Nervous Systems Diseases—2005—pp. 57-67—vol. 16—No. 1—Freund & Pettman—United Kingdom.
Borsello et al.—A Peptide Inhibitor of c-Jun N-Terminal Kinase Protects Against Excitotoxicity and Cerebral Ischemia—Aug. 24, 2003 (Sep. 2003)—pp. 1180-1186—vol. 9—No. 9—Nature Medicine—USA.
Borsello, Tiziana and Bonny, Christophe—Use of Cell-Permeable Peptides to Prevent Neuronal Degeneration—Trends in Molecular Medicine—May 2004—pp. 239-244—vol. 10—No. 5—Elsevier Ltd—www.sciencedirect.com—USA.
Bradley, Christina Marchette and Barrick, Doug—Limits of Cooperativity in a Structurally Modular Protein: Response of the Notch Ankyrin Dpmaon to Analogous Alanine Substitutions in Each Repeat—JMB—Journal of Molecular Biology—Nov. 22, 2002—pp. 373-386—vol. 324—USA.

(56) References Cited

OTHER PUBLICATIONS

Branden et al.—A Peptide Nucleic Acid-Nuclear Localization Signal Fusion that Mediates Nuclear Transport of DNA—Nature Biotechnology—Aug. 1999—pp. 784-787—vol. 17—Nature America Inc.—USA.
Branden, Carl and Tooze, Carl—Introduction to Protein—Second Edition—1999—Garland Publishing, Inc.—p. 382—USA.
Branden, Carl and Tooze, Carl—Introduction to Protein—1991—Garland Publishing, Inc.—p. 247—USA.
Cardozo et al.—Cell-Permeable Peptides Induce Dose- and Length-Dependent Cytotoxic Effects—Biochimica et Biophysica Acta—Jun. 14, 2007—pp. 2222-2234—No. 1768—ScienceDirect—Elsevier B.V.—The Netherlands.
Chaloin et al.—Design of Carrier Peptide-Oligonucleotide Conjugates with Rapid Membrane Translocation and Nuclear Localization Properties—Biochemical and Biophysical Research Communications—Article No. RC978050—1998—pp. 601-608—vol. 243—No. 2—Academic Press—Elsevier B.V.—The Nethlands.
Creighton, Thomas E. (Editor)—Janin, Jaël—Protein—Protein Interactions—Encyclopedia of Molecular Biology—1999—pp. 2027-2033—vol. 1—A Wiley-Interscience Publication—John Wiley & Sons, Inc.—USA.
Derossi et al.—Cell Internalization of the Third Helix of the Antennapedia Homeodomain is Receptor-independent—The Journal of Biological Chemistry—Jul. 26, 1996—pp. 18188-18193—vol. 271—The American Society for Biochemistry and Molecular Biology, Inc.—USA.
Designing Custom Peptides—Sigma Genosys—Technical Bulletin—Dec. 16, 2004—2 pages—<http://www.sigma-genosys.com/peptide_design.asp>—USA.
Dickens et al.—Database—Uniprot—Retrieved from EBI—Database Accession No. Q9WVI9—Abstracts—Feb. 28, 2003—Document No. XP-002366175—USA.
Dickens et al.—A Cytoplasmic Inhibitor of the JNK Signal Transduction Pathway—Science—Aug. 1, 1997—pp. 693-696—vol. 277—No. 5326—Science Magazine—USA.
Dietz, Gunner P.H. and Bahr, Mathias—Review—Delivery of Bioactive Molecules into the Cell: The Trojan Horse Approach—Molecular and Cellular Neuroscience—2004—pp. 85-131—vol. 27—Elsevier Inc.—The Netherlands.
Dominguez-Bendala et al.—TAT-Mediated Neurogenin 3 Protein Transduction Stimulates Pancreatic Endocrine Differentiation In Vitro—Diabetes—Mar. 2005—pp. 720-726—vol. 54—The American Diabetes Association—USA.
Fawell et al.—Tat-Mediated Delivery of Heterologous Proteins into Cells—Cell Biology—Proceedings of the National Academy Sciences—Jan. 8, 1994—pp. 664-668—vol. 91—Biogen Inc.—USA.
Fornoni et al.—The L-Isoform but not D-Isoforms of a JNK Inhibitory Peptide Protects Pancreatic β-cells—Biochemical and Biophysical Research Communications—Jan. 2, 2007—pp. 227-233—vol. 354—ScienceDirect—Elsevier Inc.—USA.
Frankel, Alan D. and Pabo, Carl O.—Cellular Uptake of the Tat Protein from Human Immunodeficiency Virus—Cell—Dec. 23, 1988—pp. 1189-1193—vol. 55—Cell Press—USA.
Futaki et al.—Arginine-rich Peptides—An Abundant Source of Membrane-Permeable Peptides Having Potential as Carriers for Intracellular Protein Delivery—The Journal of Biological Chemistry—Feb. 23, 2001—pp. 5836-5840—vol. 276—No. 8—The American Society of Biochemistry and Molecular Biology, Inc.—USA.
Gammon et al.—Quantitative Analysis of Permeation Peptide Complexes Labeled with Technetium-99m: Chiral and.Sequence-Specific Effects on Net Cell Uptake—Bioconjugate Chemistry—Mar. 4, 2003—pp. 368-376—vol. 14—No. 2—American Chemical Society—USA.
Gotthardt et al.—Interactions of the Low Density Lipoprotein Receptor Gene Family with Cytosolic Adaptor and Scaffold Proteins Suggest Diverse Biological Functions in Cellular Communication and Signal Transduction—The Journal of Biological Chemistry—Aug. 18, 2000—pp. 25616-25624—vol. 275—No. 33—The American Society for Biochemistry and Molecular Biology, Inc.—USA.
Guichard et al.—Antigenic Mimicry of Natural L-Peptides with Retro-Inverso-Peptidomimetics—Proceedings of the National Academy of Sciences—Immunology—Oct. 1994—pp. 9765-9769—vol. 91—The National Academy of Sciences—USA.
Gunaseelan et al.—Synthesis of Poly(ethylene glycol)-Based Saquinavir Prodrug Conjugates and Assessment of Release and Anti-HIV-1 Bioactivity Using a Novel Protease Inhibition Assay—Bioconjugate Chemistry—Oct. 28, 2004—pp. 1322-1333—vol. 15—No. 6—American Chemical Society—USA.
Gura, Trisha—Cancer Models: Systems for Identifying New Drugs Are Often Faulty—Science—Nov. 7, 1997—pp. 1041-1042—No. 278 (5340)—USA.
Hawiger, Jacek—Noninvasive Intracellular Delivery of Functional Peptides and Proteins—Current Opinion in Chemical Biology—1999—pp. 89-94—vol. 3—Elsevier Science Ltd—USA.
Hayashi et al.—Development of Oligoarginine-Drug Conjugates Linked to New Peptidic Self-Cleavable Spacers Toward Effective Intestinal Absorption—Bioorganic and Medicinal Chemistry Letters—Jul. 7, 2007—pp. 5129-5132—vol. 17—ScienceDirect—Elsevier Ltd—USA.
Heemskerk et al.—From Chemical to Drug: Neurodegeneration Drug Screening and the Ethics of Clinical Trials—Commentary—Nature Neuroscience Supplement—Nov. 2002—pp. 1027-1029—vol. 5—Nature Publishing Group—http://www.nature.com/natureneuroscience—USA.
Herve et al.—On the Immunogenic Properties of Retro-Inverso Peptides. Total Retro-Inversion of T-Cell Epitopes Causes a Loss of Binding to MHC II Molecules—Molecular Immunology—1997—pp. 157-163—vol. 34—No. 2—Elsevier Science Ltd.—United Kingdom.
Hillier et al.—*Homo sapiens*—The WashU-Merck EST Project—EMBL Sequence Database—R85141—Aug. 17, 1995—p. 1—XP-002076858—USA.
Ho et al.—Synthetic Protein Transduction Domains: Enhanced Transduction Potential in Vitro and in Vivo—Advances in Brief—Cancer Research—Jan. 15, 2001—pp. 474-477—vol. 61—USA.
Holinger et al.—Bak BH3 Peptides Antagonize Bcl-xL Function and Induce Apoptosis through Cytochrome c-independent Activation of Caspases—The Journal of Biological Chemistry—May 7, 1999—pp. 13298-13304—vol. 274—No. 19—The American Society for Biochemistry and Molecular Biology, Inc.—USA.
Holzberg et al.—Disruption of the c-JUN-JNK Complex by a Cell-permeable Peptide Containing the c-JUN δ Domain Induces Apoptosis and Affects a Distinct Set of Interleukin-1-induced Inflammatory Genes—The Journal of Biological Chemistry—Oct. 10, 2003—pp. 40213-40223—vol. 278—No. 41—The American Society for Biochemistry and Molecular Biology, Inc.—USA.
Houghten, Richard A.—General Method for the Rapid Solid-Phase Synthesis of Large Numbers of Peptides: Specificity of Antigen-Antibody Interaction at the Level of Individual Amino Acid—Proceedings of the National Academy of Sciences—Immunology—Aug. 1985—pp. 5131-5135—vol. 82—The National Academy of Sciences—USA.
Huq et al.—Specific Recognition of HIV-1 TAR RNA by a D-Tat Peptide—Comment—Nature Structural Biology—Nov. 1997—pp. 881-882—vol. 4—No. 11—Nature Publishing Group—http://www.nature.com/nsmb—USA.
Johnson, Gary L. and Nakamura, Kazuhiro—The c-jun Kinase/Stress-Activated Pathway: Regulation, Function and Role in Human Disease—Biochimica et Biophysica Acta—Jan. 4, 2007—pp. 1341-1348—vol. 1773—ScienceDirect—Elsevier B.V.—The Netherlands.
Jung, Günther (Editor)—Chapter 5—The Versatility of Nonsupport-Bound Combinatorial Libraries—Pinilla et al.—Combinatorial Peptide and Nonpeptide Libraries—A Handbook—May 1997—pp. 139-171—Wiley-VCH—USA.
Jung, Günther (Editor)—Chapter 11—Cyclic Peptide Libraries: Recent Developments—Spatola, Arno F. and Romanovskis, Peteris—Combinatorial Peptide and Nonpeptide Libraries—A Handbook—May 1997—pp. 327-347—Wiley-VCH—USA.
Hommes et al., "Inhibition of stress-activated MAP kinases induces clinical improvement in moderate to severe Crohn's disease," Gastroenterology, 122(1):7-14 (2002).
Mitsuyama et al., "Pro-inflammatory signaling by Jun-N-terminal kinase in inflammatory bowel disease," Int J Mol Med., 17(3):449-55 (2006).
Qin et al., "TAT Protein Transduction Domains : New Promise for Protein Therapy," Chinese Journal of Biochemistry and Molecular Biology, 23(7): 519-524 (2007) (Abstract Translated).

| SEQ ID NO: | Sequence | | hJNK1 | | | hJNK2 | | | hJNK3 | | |
|---|---|---|---|---|---|---|---|---|---|---|---|
| | | | IC50 | SEM | n | IC50 | SEM | n | IC50 | SEM | n |
| 193 | NH2 | R P K R P T T L N L F CONH2 | 39,52 | 0,57 | 2 | 183,85 | 50,45 | 2 | 67,68 | 13,92 | 2 |
| 2 | NH2 | r P K R P T T L N L F CONH2 | 65,55 | 26,03 | 3 | 423,53 | 241,45 | 3 | 103,32 | 36,53 | 3 |
| 3 | NH2 | R P k R P T T L N L F CONH2 | 311,63 | 99,86 | 4 | 1213,53 | 437,87 | 4 | 359,47 | 161,02 | 4 |
| 5 | NH2 | R P K R P T T L n L F CONH2 | 347,55 | 174,17 | 4 | 1501,88 | 701,33 | 4 | 387,15 | 179,51 | 4 |
| 6 | NH2 | R P K R P T T L r L F CONH2 | 90,50 | 29,63 | 4 | 358,75 | 105,28 | 4 | 119,50 | 39,82 | 4 |
| 7 | NH2 | R P K R P T T L N L f CONH2 | 69,53 | 21,75 | 4 | 278,18 | 51,43 | 4 | 88,97 | 26,72 | 4 |

Fig. 2

| SEQ ID NO: | | Sequence | | hJNK1 | | | hJNK2 | | | hJNK3 | | |
|---|---|---|---|---|---|---|---|---|---|---|---|---|
| | | | | IC50 | SEM | n | IC50 | SEM | n | IC50 | SEM | n |
| 196 | NH2 | G R K K R R Q R R R P P R P K R P T T L N L F P Q V P R S Q D | CONH2 | 42,20 | 8,17 | 8 | 8,43 | 2,01 | 6 | 5,22 | 0,71 | 6 |
| 197 | CONH2 | G r k k r r q r r r p p r p k r p t t l n l f p q v p r s q d | NH2 | 24358,50 | 10019,91 | 8 | 801,77 | 114,66 | 11 | 1294,24 | 255,51 | 11 |
| 194 | NH2 | G R K K R R Q R R R P P K R P T T L N L F P Q V P R S Q D | CONH2 | 13,99 | 0,06 | 2 | 12,70 | 0,48 | 2 | 2,59 | 0,08 | 2 |
| 195 | NH2 | G R K K R R Q R R R P P T T L N L F P Q V P R S Q D | CONH2 | 10,77 | 1,83 | 2 | 11,26 | 0,56 | 2 | 4,92 | 0,27 | 2 |
| 172 | NH2 | r K K R r Q R R r R P k R P a T L N L f | CONH2 | 722,49 | 124,56 | 7 | 54,66 | 13,04 | 7 | 102,32 | 47,81 | 7 |
| 200 | NH2 | r K K R r Q R R r R P k A A a A A N A f | CONH2 | NA | NA | 6 | 3324,00 | 2469,99 | 6 | 3820,81 | 3190,08 | 6 |
| 46 | NH2 | r K K R r Q R R r | CONH2 | NA | NA | 3 | 5340,33 | 1803,08 | 3 | 8130,86 | 5323,73 | 3 |
| 173 | NH2 | r K K R r Q R R r R P k R P T T L r L f | CONH2 | 88,35 | 4,02 | 2 | 30,03 | 0,16 | 2 | 16,76 | 2,03 | 2 |
| 174 | NH2 | r K K R r Q R R r Q R r R P T T L N L f | CONH2 | 333,73 | 36,46 | 3 | 120,13 | 4,53 | 3 | 63,12 | 6,04 | 3 |
| 175 | NH2 | r K K R r Q R R r Q R r R P T T L N L f | CONH2 | 185,30 | 18,10 | 3 | 82,30 | 9,26 | 3 | 60,60 | 6,01 | 3 |
| 176 | NH2 | r K K R r Q R R r Q R r R P k R P T T L N L w | CONH2 | 131,17 | 12,28 | 3 | 40,33 | 4,60 | 3 | 22,38 | 1,60 | 3 |
| 177 | NH2 | r K K R r Q R R r Q R r R P k R P T D L N L f | CONH2 | 355,10 | 34,02 | 3 | 87,20 | 7,12 | 3 | 45,38 | 6,70 | 3 |
| 178 | NH2 | r K K R r Q R R r Q R r R P T T L L r L w | CONH2 | 329,33 | 12,26 | 3 | 108,60 | 42,64 | 3 | 30,41 | 5,81 | 3 |
| 179 | NH2 | r K K R r Q R R r Q R r R P T T L L r L w | CONH2 | 249,47 | 22,35 | 3 | 122,11 | 20,73 | 3 | 45,66 | 3,79 | 3 |
| 180 | NH2 | r K K R r Q R R r Q R r R P k R P T D L r L w | CONH2 | 265,20 | 34,65 | 3 | 117,65 | 10,58 | 2 | 46,99 | 8,21 | 2 |
| 181 | NH2 | r K K R r Q R R r Q R r R P k R P T D L r L w | CONH2 | 293,70 | 9,79 | 2 | 160,22 | 40,13 | 2 | 47,56 | 5,77 | 2 |
| 182 | NH2 | r K K R r Q R R r Q R r R P a T L N L f | CONH2 | 1677,50 | 34,50 | 2 | 168,40 | 20,80 | 2 | 59,36 | 2,35 | 2 |
| 183 | NH2 | r K K R r Q R R r Q R r R P a T L N L f | CONH2 | 2588,00 | 494,00 | 2 | 427,30 | 25,00 | 2 | 199,20 | 3,90 | 2 |
| 184 | NH2 | r K K R r Q R R r Q R r t K R P s T L N L f | CONH2 | 2426,00 | 129,00 | 2 | 205,95 | 8,25 | 2 | 129,45 | 9,65 | 2 |
| 185 | NH2 | r K K R r Q R R r Q R r R P k R P s T L N L f | CONH2 | 765,65 | 78,15 | 2 | 72,09 | 2,85 | 2 | 35,52 | 6,34 | 2 |
| 186 | NH2 | r K K R r Q R R r Q R r R P k R P q T L N L f | CONH2 | 1021,30 | 100,70 | 2 | 52,59 | 2,73 | 2 | 44,24 | 4,80 | 2 |
| 187 | NH2 | r K K R r Q R R r Q R r R P k R P k T L N L f | CONH2 | 594,45 | 40,45 | 2 | 37,88 | 5,47 | 2 | 25,41 | 8,95 | 2 |
| 188 | NH2 | r K K R r Q R R r Q R r G K R K A L K L f | CONH2 | 1421,00 | 98,00 | 2 | 98,14 | 27,26 | 2 | 36,12 | 2,46 | 2 |
| 189 | NH2 | r K K R r Q R R r Q R r G K R R K A L r L f | CONH2 | 22270,00 | 5090,00 | 2 | 175,60 | 1,30 | 2 | 127,72 | 31,88 | 2 |
| 190 | NH2 | r K K R r Q R R r Q R r R K A L r L f | CONH2 | 8969,50 | 2070,50 | 2 | 148,20 | 9,70 | 2 | 159,35 | 13,45 | 2 |

Fig. 4

SEQUENCE LISTING

```
<160> NUMBER OF SEQ ID NOS: 199

<210> SEQ ID NO 1
<211> LENGTH: 11
<212> TYPE: PRT
<213> ORGANISM: Artificial
<220> FEATURE:
<223> OTHER INFORMATION: Consensus new JNK inhibitors
<220> FEATURE:
<221> NAME/KEY: Variant
<222> LOCATION: (1)..(1)
<223> OTHER INFORMATION: X1 may  be R, P, Q or D-enantiomeric r
<220> FEATURE:
<221> NAME/KEY: Variant
<222> LOCATION: (2)..(2)
<223> OTHER INFORMATION: X2 may  be R, P, G or D-enantiomeric r
<220> FEATURE:
<221> NAME/KEY: Variant
<222> LOCATION: (3)..(3)
<223> OTHER INFORMATION: X3 may  be K, R or D-enantionmeric k or r
<220> FEATURE:
<221> NAME/KEY: Variant
<222> LOCATION: (5)..(5)
<223> OTHER INFORMATION: X4 may  be P or K
<220> FEATURE:
<221> NAME/KEY: Variant
<222> LOCATION: (6)..(6)
<223> OTHER INFORMATION: X5 may  be T, or D-enantiomeric a, s, q, k or
      absent
<220> FEATURE:
<221> NAME/KEY: Variant
<222> LOCATION: (7)..(7)
<223> OTHER INFORMATION: X6 may  be T, D or A
<220> FEATURE:
<221> NAME/KEY: Variant
<222> LOCATION: (9)..(9)
<223> OTHER INFORMATION: X7 may  be N, K or D-enantiomeric n or r
<220> FEATURE:
<221> NAME/KEY: Variant
<222> LOCATION: (11)..(11)
<223> OTHER INFORMATION: X8 may  be F or D-enantiomeric f or w
```

```
<400> SEQUENCE: 1

Xaa Xaa Xaa Arg Xaa Xaa Xaa Leu Xaa Leu Xaa
1               5                   10

<210> SEQ ID NO 2
<211> LENGTH: 11
<212> TYPE: PRT
<213> ORGANISM: Artificial
<220> FEATURE:
<223> OTHER INFORMATION: rPKRPTTLNLF JNK inhibitor
<220> FEATURE:
<221> NAME/KEY: Variant
<222> LOCATION: (1)..(1)
<223> OTHER INFORMATION: Arg is D-enantiomeric Arg

<400> SEQUENCE: 2

Arg Pro Lys Arg Pro Thr Thr Leu Asn Leu Phe
1               5                   10

<210> SEQ ID NO 3
<211> LENGTH: 11
<212> TYPE: PRT
<213> ORGANISM: Artificial
<220> FEATURE:
<223> OTHER INFORMATION: RPkRPTTLNLF JNK inhibitor
<220> FEATURE:
<221> NAME/KEY: Variant
<222> LOCATION: (3)..(3)
<223> OTHER INFORMATION: Lys is D-enantiomeric Lys

<400> SEQUENCE: 3

Arg Pro Lys Arg Pro Thr Thr Leu Asn Leu Phe
1               5                   10

<210> SEQ ID NO 4
<211> LENGTH: 11
<212> TYPE: PRT
<213> ORGANISM: Artificial
<220> FEATURE:
<223> OTHER INFORMATION: RPKRPaTLNLF JNK inhibitor
<220> FEATURE:
<221> NAME/KEY: Variant
<222> LOCATION: (6)..(6)
<223> OTHER INFORMATION: Ala is D-enantiomeric Ala

<400> SEQUENCE: 4

Arg Pro Lys Arg Pro Ala Thr Leu Asn Leu Phe
1               5                   10

<210> SEQ ID NO 5
<211> LENGTH: 11
<212> TYPE: PRT
<213> ORGANISM: Artificial
<220> FEATURE:
<223> OTHER INFORMATION: RPKRPTTLnLF JNK inhibitor
<220> FEATURE:
<221> NAME/KEY: Variant
<222> LOCATION: (9)..(9)
<223> OTHER INFORMATION: Asn is D-enantiomeric Asn

<400> SEQUENCE: 5

Arg Pro Lys Arg Pro Thr Thr Leu Asn Leu Phe
1               5                   10

<210> SEQ ID NO 6
<211> LENGTH: 11
<212> TYPE: PRT
<213> ORGANISM: Artificial
<220> FEATURE:
```

```
<223> OTHER INFORMATION: RPKRPTTLrLF JNK inhibitor
<220> FEATURE:
<221> NAME/KEY: Variant
<222> LOCATION: (9)..(9)
<223> OTHER INFORMATION: Arg is D-enantiomeric Arg

<400> SEQUENCE: 6

Arg Pro Lys Arg Pro Thr Thr Leu Arg Leu Phe
1               5                   10

<210> SEQ ID NO 7
<211> LENGTH: 11
<212> TYPE: PRT
<213> ORGANISM: Artificial
<220> FEATURE:
<223> OTHER INFORMATION: RPKRPTTLNLf JNK inhibitor
<220> FEATURE:
<221> NAME/KEY: Variant
<222> LOCATION: (11)..(11)
<223> OTHER INFORMATION: Phe is D-enantiomeric Phe

<400> SEQUENCE: 7

Arg Pro Lys Arg Pro Thr Thr Leu Asn Leu Phe
1               5                   10

<210> SEQ ID NO 8
<211> LENGTH: 11
<212> TYPE: PRT
<213> ORGANISM: Artificial
<220> FEATURE:
<223> OTHER INFORMATION: RPkRPaTLNLf JNK inhibitor
<220> FEATURE:
<221> NAME/KEY: Variant
<222> LOCATION: (3)..(3)
<223> OTHER INFORMATION: Lys is D-enantiomeric Lys
<220> FEATURE:
<221> NAME/KEY: Variant
<222> LOCATION: (6)..(6)
<223> OTHER INFORMATION: Ala is D-enantiomeric Ala
<220> FEATURE:
<221> NAME/KEY: Variant
<222> LOCATION: (11)..(11)
<223> OTHER INFORMATION: Phe is D-enantiomeric Phe

<400> SEQUENCE: 8

Arg Pro Lys Arg Pro Ala Thr Leu Asn Leu Phe
1               5                   10

<210> SEQ ID NO 9
<211> LENGTH: 11
<212> TYPE: PRT
<213> ORGANISM: Artificial
<220> FEATURE:
<223> OTHER INFORMATION: RPkRPTTLNLf JNK inhibitor
<220> FEATURE:
<221> NAME/KEY: Variant
<222> LOCATION: (3)..(3)
<223> OTHER INFORMATION: Lys is D-enantiomeric Lys
<220> FEATURE:
<221> NAME/KEY: Variant
<222> LOCATION: (11)..(11)
<223> OTHER INFORMATION: Phe is D-enantiomeric Phe

<400> SEQUENCE: 9

Arg Pro Lys Arg Pro Thr Thr Leu Asn Leu Phe
1               5                   10

<210> SEQ ID NO 10
<211> LENGTH: 11
<212> TYPE: PRT
<213> ORGANISM: Artificial
```

```
<220> FEATURE:
<223> OTHER INFORMATION: RPkRPTTLrLf JNK inhibitor
<220> FEATURE:
<221> NAME/KEY: Variant
<222> LOCATION: (3)..(3)
<223> OTHER INFORMATION: Lys is D-enantiomeric Lys
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (11)..(11)
<223> OTHER INFORMATION: Phe is D-enantiomeric Phe

<400> SEQUENCE: 10

Arg Pro Lys Arg Pro Thr Thr Leu Arg Leu Phe
1               5                   10

<210> SEQ ID NO 11
<211> LENGTH: 11
<212> TYPE: PRT
<213> ORGANISM: Artificial
<220> FEATURE:
<223> OTHER INFORMATION: RRrRPTTLNLf JNK inhibitor
<220> FEATURE:
<221> NAME/KEY: Variant
<222> LOCATION: (3)..(3)
<223> OTHER INFORMATION: Arg is D-enantiomeric Arg
<220> FEATURE:
<221> NAME/KEY: Variant
<222> LOCATION: (11)..(11)
<223> OTHER INFORMATION: Phe is D-enantiomeric Phe

<400> SEQUENCE: 11

Arg Arg Arg Arg Pro Thr Thr Leu Asn Leu Phe
1               5                   10

<210> SEQ ID NO 12
<211> LENGTH: 11
<212> TYPE: PRT
<213> ORGANISM: Artificial
<220> FEATURE:
<223> OTHER INFORMATION: QRrRPTTLNLf JNK inhibitor
<220> FEATURE:
<221> NAME/KEY: Variant
<222> LOCATION: (3)..(3)
<223> OTHER INFORMATION: Arg is D-enantiomeric Arg
<220> FEATURE:
<221> NAME/KEY: Variant
<222> LOCATION: (11)..(11)
<223> OTHER INFORMATION: Phe is D-enantiomeric Phe

<400> SEQUENCE: 12

Gln Arg Arg Arg Pro Thr Thr Leu Asn Leu Phe
1               5                   10

<210> SEQ ID NO 13
<211> LENGTH: 11
<212> TYPE: PRT
<213> ORGANISM: Artificial
<220> FEATURE:
<223> OTHER INFORMATION: RPkRPTTLNLw JNK inhibitor
<220> FEATURE:
<221> NAME/KEY: Variant
<222> LOCATION: (3)..(3)
<223> OTHER INFORMATION: Lys is D-enantiomeric Lys
<220> FEATURE:
<221> NAME/KEY: Variant
<222> LOCATION: (11)..(11)
<223> OTHER INFORMATION: Trp is D-enantiomeric Trp

<400> SEQUENCE: 13
```

```
Arg Pro Lys Arg Pro Thr Thr Leu Asn Leu Trp
1               5                   10

<210> SEQ ID NO 14
<211> LENGTH: 11
<212> TYPE: PRT
<213> ORGANISM: Artificial
<220> FEATURE:
<223> OTHER INFORMATION: RPkRPTDLNLf JNK inhibitor
<220> FEATURE:
<221> NAME/KEY: Variant
<222> LOCATION: (3)..(3)
<223> OTHER INFORMATION: Lys is D-enantiomeric Lys
<220> FEATURE:
<221> NAME/KEY: Variant
<222> LOCATION: (11)..(11)
<223> OTHER INFORMATION: Phe is D-enantiomeric Phe

<400> SEQUENCE: 14

Arg Pro Lys Arg Pro Thr Asp Leu Asn Leu Phe
1               5                   10

<210> SEQ ID NO 15
<211> LENGTH: 11
<212> TYPE: PRT
<213> ORGANISM: Artificial
<220> FEATURE:
<223> OTHER INFORMATION: RRrRPTTLrLw JNK inhibitor
<220> FEATURE:
<221> NAME/KEY: Variant
<222> LOCATION: (3)..(3)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (11)..(11)
<223> OTHER INFORMATION: Trp is D-enantiomeric Trp

<400> SEQUENCE: 15

Arg Arg Arg Arg Pro Thr Thr Leu Arg Leu Trp
1               5                   10

<210> SEQ ID NO 16
<211> LENGTH: 11
<212> TYPE: PRT
<213> ORGANISM: Artificial
<220> FEATURE:
<223> OTHER INFORMATION: QRrRPTTLrLw JNK inhibitor
<220> FEATURE:
<221> NAME/KEY: Variant
<222> LOCATION: (3)..(3)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (11)..(11)
<223> OTHER INFORMATION: Trp is D-enantiomeric Trp

<400> SEQUENCE: 16

Gln Arg Arg Arg Pro Thr Thr Leu Arg Leu Trp
1               5                   10

<210> SEQ ID NO 17
<211> LENGTH: 11
<212> TYPE: PRT
```

```
<213> ORGANISM: Artificial
<220> FEATURE:
<223> OTHER INFORMATION: RRrRPTDLrLw JNK inhibitor
<220> FEATURE:
<221> NAME/KEY: Variant
<222> LOCATION: (3)..(3)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (11)..(11)
<223> OTHER INFORMATION: Trp is D-enantiomeric Trp

<400> SEQUENCE: 17

Arg Arg Arg Arg Pro Thr Asp Leu Arg Leu Trp
1               5                   10

<210> SEQ ID NO 18
<211> LENGTH: 11
<212> TYPE: PRT
<213> ORGANISM: Artificial
<220> FEATURE:
<223> OTHER INFORMATION: QRrRPTDLrLw JNK inhibitor
<220> FEATURE:
<221> NAME/KEY: Variant
<222> LOCATION: (3)..(3)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (11)..(11)
<223> OTHER INFORMATION: Trp is D-enantiomeric Trp

<400> SEQUENCE: 18

Gln Arg Arg Arg Pro Thr Asp Leu Arg Leu Trp
1               5                   10

<210> SEQ ID NO 19
<211> LENGTH: 11
<212> TYPE: PRT
<213> ORGANISM: Artificial
<220> FEATURE:
<223> OTHER INFORMATION: RRrRPaTLNLf JNK inhibitor
<220> FEATURE:
<221> NAME/KEY: Variant
<222> LOCATION: (3)..(3)
<223> OTHER INFORMATION: Arg is D-enantiomeric Arg
<220> FEATURE:
<221> NAME/KEY: Variant
<222> LOCATION: (6)..(6)
<223> OTHER INFORMATION: Ala is D-enantiomeric Ala
<220> FEATURE:
<221> NAME/KEY: Variant
<222> LOCATION: (11)..(11)
<223> OTHER INFORMATION: Phe is D-enantiomeric Phe

<400> SEQUENCE: 19

Arg Arg Arg Arg Pro Ala Thr Leu Asn Leu Phe
1               5                   10

<210> SEQ ID NO 20
<211> LENGTH: 11
<212> TYPE: PRT
<213> ORGANISM: Artificial
<220> FEATURE:
<223> OTHER INFORMATION: QRrRPaTLNLf JNK inhibitor
<220> FEATURE:
```

```
<221> NAME/KEY: Variant
<222> LOCATION: (3)..(3)
<223> OTHER INFORMATION: Arg is D-enantiomeric Arg
<220> FEATURE:
<221> NAME/KEY: Variant
<222> LOCATION: (6)..(6)
<223> OTHER INFORMATION: Ala is D-enantiomeric Ala
<220> FEATURE:
<221> NAME/KEY: Variant
<222> LOCATION: (11)..(11)
<223> OTHER INFORMATION: Phe is D-enantiomeric Phe

<400> SEQUENCE: 20

Gln Arg Arg Arg Pro Ala Thr Leu Asn Leu Phe
1               5                   10

<210> SEQ ID NO 21
<211> LENGTH: 11
<212> TYPE: PRT
<213> ORGANISM: Artificial
<220> FEATURE:
<223> OTHER INFORMATION: RrKRPaTLNLf JNK inhibitor
<220> FEATURE:
<221> NAME/KEY: Variant
<222> LOCATION: (2)..(2)
<223> OTHER INFORMATION: Arg is D-enantiomeric Arg
<220> FEATURE:
<221> NAME/KEY: Variant
<222> LOCATION: (6)..(6)
<223> OTHER INFORMATION: Ala is D-enantiomeric Ala
<220> FEATURE:
<221> NAME/KEY: Variant
<222> LOCATION: (11)..(11)
<223> OTHER INFORMATION: Phe is D-enantiomeric Phe

<400> SEQUENCE: 21

Arg Arg Lys Arg Pro Ala Thr Leu Asn Leu Phe
1               5                   10

<210> SEQ ID NO 22
<211> LENGTH: 11
<212> TYPE: PRT
<213> ORGANISM: Artificial
<220> FEATURE:
<223> OTHER INFORMATION: RPkRPsTLNLf JNK inhibitor
<220> FEATURE:
<221> NAME/KEY: Variant
<222> LOCATION: (3)..(3)
<223> OTHER INFORMATION: Lys is D-enantiomeric Lys
<220> FEATURE:
<221> NAME/KEY: Variant
<222> LOCATION: (6)..(6)
<223> OTHER INFORMATION: Ser is D-enantiomeric Ser
<220> FEATURE:
<221> NAME/KEY: Variant
<222> LOCATION: (11)..(11)
<223> OTHER INFORMATION: Phe is D-enantiomeric Phe

<400> SEQUENCE: 22

Arg Pro Lys Arg Pro Ser Thr Leu Asn Leu Phe
1               5                   10

<210> SEQ ID NO 23
<211> LENGTH: 11
<212> TYPE: PRT
<213> ORGANISM: Artificial
<220> FEATURE:
<223> OTHER INFORMATION: RPkRPqTLNLf JNK inhibitor
<220> FEATURE:
<221> NAME/KEY: Variant
<222> LOCATION: (3)..(3)
<223> OTHER INFORMATION: Lys is D-enantiomeric Lys
<220> FEATURE:
```

```
<221> NAME/KEY: Variant
<222> LOCATION: (6)..(6)
<223> OTHER INFORMATION: Gln is D-enantiomeric Gln
<220> FEATURE:
<221> NAME/KEY: Variant
<222> LOCATION: (11)..(11)
<223> OTHER INFORMATION: Phe is D-enantiomeric Phe

<400> SEQUENCE: 23

Arg Pro Lys Arg Pro Gln Thr Leu Asn Leu Phe
1               5                   10

<210> SEQ ID NO 24
<211> LENGTH: 11
<212> TYPE: PRT
<213> ORGANISM: Artificial
<220> FEATURE:
<223> OTHER INFORMATION: RPkRPkTLNLf JNK inhibitor
<220> FEATURE:
<221> NAME/KEY: Variant
<222> LOCATION: (3)..(3)
<223> OTHER INFORMATION: Lys is D-enantiomeric Lys
<220> FEATURE:
<221> NAME/KEY: Variant
<222> LOCATION: (6)..(6)
<223> OTHER INFORMATION: Lys is D-enantiomeric Lys
<220> FEATURE:
<221> NAME/KEY: Variant
<222> LOCATION: (11)..(11)
<223> OTHER INFORMATION: Phe is D-enantiomeric Phe

<400> SEQUENCE: 24

Arg Pro Lys Arg Pro Lys Thr Leu Asn Leu Phe
1               5                   10

<210> SEQ ID NO 25
<211> LENGTH: 10
<212> TYPE: PRT
<213> ORGANISM: Artificial
<220> FEATURE:
<223> OTHER INFORMATION: rGKRKALKLf JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (10)..(10)
<223> OTHER INFORMATION: Phe  is D-enantiomeric Phe

<400> SEQUENCE: 25

Arg Gly Lys Arg Lys Ala Leu Lys Leu Phe
1               5                   10

<210> SEQ ID NO 26
<211> LENGTH: 10
<212> TYPE: PRT
<213> ORGANISM: Artificial
<220> FEATURE:
<223> OTHER INFORMATION: rGKRKALrLf JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (8)..(8)
<223> OTHER INFORMATION: Arg is D-enantiomeric Arg
<220> FEATURE:
<221> NAME/KEY: Variant
<222> LOCATION: (10)..(10)
<223> OTHER INFORMATION: Phe is D-enantiomeric Phe
```

-continued

```
<400> SEQUENCE: 26

Arg Gly Lys Arg Lys Ala Leu Arg Leu Phe
1               5                   10

<210> SEQ ID NO 27
<211> LENGTH: 10
<212> TYPE: PRT
<213> ORGANISM: Artificial
<220> FEATURE:
<223> OTHER INFORMATION: RRrRKALrLf JNK inhibitor
<220> FEATURE:
<221> NAME/KEY: Variant
<222> LOCATION: (3)..(3)
<223> OTHER INFORMATION: Arg is D-enantiomeric Arg
<220> FEATURE:
<221> NAME/KEY: Variant
<222> LOCATION: (8)..(8)
<223> OTHER INFORMATION: Arg is D-enantiomeric Arg
<220> FEATURE:
<221> NAME/KEY: Variant
<222> LOCATION: (10)..(10)
<223> OTHER INFORMATION: Phe is D-enantiomeric Phe

<400> SEQUENCE: 27

Arg Arg Arg Arg Lys Ala Leu Arg Leu Phe
1               5                   10

<210> SEQ ID NO 28
<211> LENGTH: 9
<212> TYPE: PRT
<213> ORGANISM: Artificial Sequence
<220> FEATURE:
<223> OTHER INFORMATION: Description of artificial sequence: generic
      subformula (Ib) DlLLLxDmLLLyDn
<220> FEATURE:
<221> NAME/KEY: VARIANT
<222> LOCATION: (1)..(9)
<223> OTHER INFORMATION: /replace="any amino acid"
<220> FEATURE:
<221> NAME/KEY: VARIANT
<222> LOCATION: (1)..(1)
<223> OTHER INFORMATION: /replace="D-amino acid""
<220> FEATURE:
<221> NAME/KEY: REPEAT
<222> LOCATION: (1)..(1)
<223> OTHER INFORMATION: number of repeats is 1 or 2
<220> FEATURE:
<221> NAME/KEY: REPEAT
<222> LOCATION: (4)..(4)
<223> OTHER INFORMATION: number of repeats is 0, 1 or 2
<220> FEATURE:
<221> NAME/KEY: VARIANT
<222> LOCATION: (5)..(5)
<223> OTHER INFORMATION: /replace="D-amino acid""
<220> FEATURE:
<221> NAME/KEY: REPEAT
<222> LOCATION: (5)..(5)
<223> OTHER INFORMATION: number of repeats is 1 or 2
<220> FEATURE:
<221> NAME/KEY: REPEAT
<222> LOCATION: (8)..(8)
<223> OTHER INFORMATION: number of repeats is 0, 1 or 2
<220> FEATURE:
<221> NAME/KEY: VARIANT
<222> LOCATION: (9)..(9)
<223> OTHER INFORMATION: /replace="D-amino acid""
<220> FEATURE:
<221> NAME/KEY: REPEAT
<222> LOCATION: (9)..(9)
<223> OTHER INFORMATION: number of repeats is 1 or 2

<400> SEQUENCE: 28

Xaa Xaa Xaa Xaa Xaa Xaa Xaa Xaa Xaa
1               5
```

```
<210> SEQ ID NO 29
<211> LENGTH: 9
<212> TYPE: PRT
<213> ORGANISM: Artificial Sequence
<220> FEATURE:
<223> OTHER INFORMATION: Description of artificial sequence: generic
      subformula (Ie) DLLLD(LLLD)a
<220> FEATURE:
<221> NAME/KEY: VARIANT
<222> LOCATION: (1)..(9)
<223> OTHER INFORMATION: /replace="any amino acid"
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: REPEAT
<222> LOCATION: (6)..(9)
<223> OTHER INFORMATION: number of repeats is 0, 1, 2 or 3
<220> FEATURE:
<221> NAME/KEY: VARIANT
<222> LOCATION: (9)..(9)
<223> OTHER INFORMATION: /replace="D-amino acid"

<400> SEQUENCE: 29

Xaa Xaa Xaa Xaa Xaa Xaa Xaa Xaa Xaa
1               5

<210> SEQ ID NO 30
<211> LENGTH: 9
<212> TYPE: PRT
<213> ORGANISM: Artificial Sequence
<220> FEATURE:
<223> OTHER INFORMATION: Description of artificial sequence: generic
      subformula (If) DLLLDLLLD
<220> FEATURE:
<221> NAME/KEY: VARIANT
<222> LOCATION: (1)..(9)
<223> OTHER INFORMATION: /replace="any amino acid"
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 30

Xaa Xaa Xaa Xaa Xaa Xaa Xaa Xaa Xaa
1               5

<210> SEQ ID NO 31
<211> LENGTH: 9
<212> TYPE: PRT
<213> ORGANISM: Artificial
<220> FEATURE:
<223> OTHER INFORMATION: Description of sequence: consensus sequence
      rXXXrXXXr
<220> FEATURE:
<221> NAME/KEY: misc_feature
<222> LOCATION: (1)..(1)
<223> OTHER INFORMATION: Arg is D-enantiomeric Arg
<220> FEATURE:
<221> NAME/KEY: misc_feature
```

```
<222> LOCATION: (2)..(4)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Arg is D-enantiomeric Arg
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Arg is D-enantiomeric Arg

<400> SEQUENCE: 31

Arg Xaa Xaa Xaa Arg Xaa Xaa Xaa Arg
1               5

<210> SEQ ID NO 32
<211> LENGTH: 9
<212> TYPE: PRT
<213> ORGANISM: Artificial
<220> FEATURE:
<223> OTHER INFORMATION: r3 (generic; right half)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (6)..(8)
<223> OTHER INFORMATION: Xaa can be any naturally occurring amino acid
<220> FEATURE:
<221> NAME/KEY: Variant
<222> LOCATION: (9)..(9)
<223> OTHER INFORMATION: Arg is D-enantiomeric Arg

<400> SEQUENCE: 32

Arg Lys Lys Arg Arg Xaa Xaa Xaa Arg
1               5

<210> SEQ ID NO 33
<211> LENGTH: 9
<212> TYPE: PRT
<213> ORGANISM: Artificial
<220> FEATURE:
<223> OTHER INFORMATION: r3 (generic; left half)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (2)..(4)
<223> OTHER INFORMATION: Xaa can be any naturally occurring amino acid
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 33

Arg Xaa Xaa Xaa Arg Gln Arg Arg Arg
1               5
```

```
<210> SEQ ID NO 34
<211> LENGTH: 9
<212> TYPE: PRT
<213> ORGANISM: Artificial
<220> FEATURE:
<223> OTHER INFORMATION: r3 (generic; individual)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (2)..(2)
<223> OTHER INFORMATION: Xaa is K or any other naturally occuring amino
      acid
<220> FEATURE:
<221> NAME/KEY: Variant
<222> LOCATION: (3)..(3)
<223> OTHER INFORMATION: Xaa is K or any other naturally occuring amino
      acid
<220> FEATURE:
<221> NAME/KEY: Variant
<222> LOCATION: (4)..(4)
<223> OTHER INFORMATION: Xaa is R or any other naturally occuring amino
      acid
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (6)..(6)
<223> OTHER INFORMATION: Xaa is Q or any other naturally occuring amino
      acid
<220> FEATURE:
<221> NAME/KEY: Variant
<222> LOCATION: (7)..(7)
<223> OTHER INFORMATION: Xaa is R or any other naturally occuring amino
      acid
<220> FEATURE:
<221> NAME/KEY: Variant
<222> LOCATION: (8)..(8)
<223> OTHER INFORMATION: Xaa is R or any other naturally occuring amino
      acid
<220> FEATURE:
<221> NAME/KEY: Variant
<222> LOCATION: (9)..(9)
<223> OTHER INFORMATION: Arg is D-enantiomeric Arg

<400> SEQUENCE: 34

Arg Xaa Xaa Xaa Arg Xaa Xaa Xaa Arg
1               5

<210> SEQ ID NO 35
<211> LENGTH: 86
<212> TYPE: PRT
<213> ORGANISM: Human immunodeficiency virus type 1
<220> FEATURE:
<221> NAME/KEY: misc_feature
<223> OTHER INFORMATION: Description of sequence:  HIV-1 TAT sequence
      (aa 1-86)

<400> SEQUENCE: 35

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Pro Pro Gln Gly Ser Gln Thr
    50                  55                  60

His Gln Val Ser Leu Ser Lys Gln Pro Thr Ser Gln Ser Arg Gly Asp
```

-continued

```
                65                  70                  75                  80
Pro Thr Gly Pro Lys Glu
                 85

<210> SEQ ID NO 36
<211> LENGTH: 36
<212> TYPE: PRT
<213> ORGANISM: Human immunodeficiency virus type 1
<220> FEATURE:
<221> NAME/KEY: misc_feature
<223> OTHER INFORMATION: Description of sequence: HIV-1 TAT sequence
      (aa 37-72)

<400> SEQUENCE: 36

Cys Phe Ile Thr Lys Ala Leu Gly Ile Ser Tyr Gly Arg Lys Lys Arg
1               5                   10                  15

Arg Gln Arg Arg Arg Pro Pro Gln Gly Ser Gln Thr His Gln Val Ser
            20                  25                  30

Leu Ser Lys Gln
        35

<210> SEQ ID NO 37
<211> LENGTH: 22
<212> TYPE: PRT
<213> ORGANISM: Human immunodeficiency virus type 1
<220> FEATURE:
<221> NAME/KEY: misc_feature
<223> OTHER INFORMATION: Description of sequence: HIV-1 TAT sequence
      (aa 37-58)

<400> SEQUENCE: 37

Cys Phe Ile Thr Lys Ala Leu Gly Ile Ser Tyr Gly Arg Lys Lys Arg
1               5                   10                  15

Arg Gln Arg Arg Arg Pro
            20

<210> SEQ ID NO 38
<211> LENGTH: 24
<212> TYPE: PRT
<213> ORGANISM: Human immunodeficiency virus type 1
<220> FEATURE:
<221> NAME/KEY: misc_feature
<223> OTHER INFORMATION: Description of sequence: HIV-1 TAT sequence
      (aa 38-58) including an additional N-terminal GCC

<400> SEQUENCE: 38

Phe Ile Thr Lys Ala Leu Gly Ile Ser Tyr Gly Arg Lys Lys Arg Arg
1               5                   10                  15

Gln Arg Arg Arg Pro Gly Gly Cys
            20

<210> SEQ ID NO 39
<211> LENGTH: 15
<212> TYPE: PRT
<213> ORGANISM: Human immunodeficiency virus type 1
<220> FEATURE:
<221> NAME/KEY: misc_feature
<223> OTHER INFORMATION: Description of sequence: HIV-1 TAT sequence
      (aa 47-58) including an additional C-terminal GCC

<400> SEQUENCE: 39

Cys Gly Gly Tyr Gly Arg Lys Lys Arg Arg Gln Arg Arg Arg Pro
1               5                   10                  15

<210> SEQ ID NO 40
```

```
<211> LENGTH: 15
<212> TYPE: PRT
<213> ORGANISM: Human immunodeficiency virus type 1
<220> FEATURE:
<221> NAME/KEY: misc_feature
<223> OTHER INFORMATION: Description of sequence: HIV-1 TAT sequence
      (aa 47-58) including an additional N-terminal GCC

<400> SEQUENCE: 40

Tyr Gly Arg Lys Lys Arg Arg Gln Arg Arg Pro Gly Gly Cys
1               5                   10                  15

<210> SEQ ID NO 41
<211> LENGTH: 56
<212> TYPE: PRT
<213> ORGANISM: Human immunodeficiency virus type 1
<220> FEATURE:
<221> NAME/KEY: misc_feature
<223> OTHER INFORMATION: Description of sequence: HIV-1 TAT sequence
      (aa 1-72) including a mutated Cys to Ala residue at position 37

<400> SEQUENCE: 41

Met Glu Pro Val Asp Pro Arg Leu Glu Pro Trp Lys His Pro Gly Ser
1               5                   10                  15

Gln Pro Lys Thr Ala Phe Ile Thr Lys Ala Leu Gly Ile Ser Tyr Gly
            20                  25                  30

Arg Lys Lys Arg Arg Gln Arg Arg Pro Pro Gln Gly Ser Gln Thr
        35                  40                  45

His Gln Val Ser Leu Ser Lys Gln
    50                  55

<210> SEQ ID NO 42
<211> LENGTH: 10
<212> TYPE: PRT
<213> ORGANISM: Artificial
<220> FEATURE:
<223> OTHER INFORMATION: Description of sequence: trafficking sequence
      L-TAT (s1a)

<400> SEQUENCE: 42

Gly Arg Lys Lys Arg Arg Gln Arg Arg Arg
1               5                   10

<210> SEQ ID NO 43
<211> LENGTH: 9
<212> TYPE: PRT
<213> ORGANISM: Artificial Sequence
<220> FEATURE:
<223> OTHER INFORMATION: Description of sequence: trafficking sequence
      L-TAT (s1b)

<400> SEQUENCE: 43

Arg Lys Lys Arg Arg Gln Arg Arg Arg
1               5

<210> SEQ ID NO 44
<211> LENGTH: 11
<212> TYPE: PRT
<213> ORGANISM: Artificial Sequence
<220> FEATURE:
<223> OTHER INFORMATION: Description of sequence: trafficking sequence
      L-TAT (s1c)

<400> SEQUENCE: 44

Tyr Asp Arg Lys Lys Arg Arg Gln Arg Arg Arg
1               5                   10
```

```
<210> SEQ ID NO 45
<211> LENGTH: 9
<212> TYPE: PRT
<213> ORGANISM: Artificial Sequence
<220> FEATURE:
<223> OTHER INFORMATION: Description of artificial sequence: D-TAT
<220> FEATURE:
<221> NAME/KEY: VARIANT
<222> LOCATION: (1)..(9)
<223> OTHER INFORMATION: all amino acids are D-enantiomeric amino acids

<400> SEQUENCE: 45

Arg Arg Arg Gln Arg Arg Lys Lys Arg
1               5

<210> SEQ ID NO 46
<211> LENGTH: 9
<212> TYPE: PRT
<213> ORGANISM: Artificial Sequence
<220> FEATURE:
<223> OTHER INFORMATION: trafficking sequence r3-L-TAT
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 46

Arg Lys Lys Arg Arg Gln Arg Arg Arg
1               5

<210> SEQ ID NO 47
<211> LENGTH: 9
<212> TYPE: PRT
<213> ORGANISM: Artificial Sequence
<220> FEATURE:
<223> OTHER INFORMATION: trafficking sequence r3-L-TATi
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 47

Arg Arg Arg Gln Arg Arg Lys Lys Arg
1               5

<210> SEQ ID NO 48
<211> LENGTH: 9
<212> TYPE: PRT
<213> ORGANISM: Artificial Sequence
<220> FEATURE:
<223> OTHER INFORMATION: Description of sequence:  trafficking sequence
      betaA-r3-L-TAT
<220> FEATURE:
<221> NAME/KEY: Variant
<222> LOCATION: (1)..(1)
<223> OTHER INFORMATION: Arg is D-enantiomeric Arg
```

```
<220> FEATURE:
<221> NAME/KEY: MOD_RES
<222> LOCATION: (1)..(1)
<223> OTHER INFORMATION: b-Alanine modified
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 48

Arg Lys Lys Arg Arg Gln Arg Arg Arg
1               5

<210> SEQ ID NO 49
<211> LENGTH: 9
<212> TYPE: PRT
<213> ORGANISM: Artificial Sequence
<220> FEATURE:
<223> OTHER INFORMATION: Description of sequence:  trafficking sequence
      betaA-r3-L-TAT
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: MOD_RES
<222> LOCATION: (1)..(1)
<223> OTHER INFORMATION: b-Alanine modified
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 49

Arg Arg Arg Gln Arg Arg Lys Lys Arg
1               5

<210> SEQ ID NO 50
<211> LENGTH: 9
<212> TYPE: PRT
<213> ORGANISM: Artificial Sequence
<220> FEATURE:
<223> OTHER INFORMATION: Description of sequence:  trafficking sequence
      FITC-betaA-r3-L-TAT
<220> FEATURE:
<221> NAME/KEY: MOD_RES
<222> LOCATION: (1)..(1)
<223> OTHER INFORMATION: FITC-b-Alanine modified
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 50

Arg Lys Lys Arg Arg Gln Arg Arg Arg
1               5
```

```
<210> SEQ ID NO 51
<211> LENGTH: 9
<212> TYPE: PRT
<213> ORGANISM: Artificial Sequence
<220> FEATURE:
<223> OTHER INFORMATION: Description of sequence: trafficking sequence
      FITC-betaA-r3-L-TAT
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: MOD_RES
<222> LOCATION: (1)..(1)
<223> OTHER INFORMATION: FITC-b-Alanine modified
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 51

Arg Arg Arg Gln Arg Arg Lys Lys Arg
1               5

<210> SEQ ID NO 52
<211> LENGTH: 9
<212> TYPE: PRT
<213> ORGANISM: Artificial Sequence
<220> FEATURE:
<223> OTHER INFORMATION: Description of sequence: trafficking sequence
      TAT(s2-1)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 52

Arg Ala Lys Arg Arg Gln Arg Arg Arg
1               5

<210> SEQ ID NO 53
<211> LENGTH: 9
<212> TYPE: PRT
<213> ORGANISM: Artificial Sequence
<220> FEATURE:
<223> OTHER INFORMATION: Description of sequence: trafficking sequence
      TAT(s2-2)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 53

Arg Lys Ala Arg Arg Gln Arg Arg Arg
```

<210> SEQ ID NO 54
<211> LENGTH: 9
<212> TYPE: PRT
<213> ORGANISM: Artificial Sequence
<220> FEATURE:
<223> OTHER INFORMATION: Description of sequence: trafficking sequence
      TAT(s2-3)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 54

Arg Lys Lys Ala Arg Gln Arg Arg Arg
1               5

<210> SEQ ID NO 55
<211> LENGTH: 9
<212> TYPE: PRT
<213> ORGANISM: Artificial Sequence
<220> FEATURE:
<223> OTHER INFORMATION: Description of sequence: trafficking sequence
      TAT(s2-4)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 55

Arg Lys Lys Arg Arg Ala Arg Arg Arg
1               5

<210> SEQ ID NO 56
<211> LENGTH: 9
<212> TYPE: PRT
<213> ORGANISM: Artificial Sequence
<220> FEATURE:
<223> OTHER INFORMATION: Description of sequence: trafficking sequence
      TAT(s2-5)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 56

Arg Lys Lys Arg Arg Gln Ala Arg Arg
1               5

```
<210> SEQ ID NO 57
<211> LENGTH: 9
<212> TYPE: PRT
<213> ORGANISM: Artificial Sequence
<220> FEATURE:
<223> OTHER INFORMATION: Description of sequence:  trafficking sequence
      TAT(s2-6))
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 57

Arg Lys Lys Arg Arg Gln Arg Ala Arg
1               5

<210> SEQ ID NO 58
<211> LENGTH: 9
<212> TYPE: PRT
<213> ORGANISM: Artificial Sequence
<220> FEATURE:
<223> OTHER INFORMATION: Description of sequence:  trafficking sequence
      TAT(s2-7)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 58

Arg Asp Lys Arg Arg Gln Arg Arg Arg
1               5

<210> SEQ ID NO 59
<211> LENGTH: 9
<212> TYPE: PRT
<213> ORGANISM: Artificial Sequence
<220> FEATURE:
<223> OTHER INFORMATION: trafficking sequence TAT(s2-8)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 59

Arg Lys Asp Arg Arg Gln Arg Arg Arg
1               5
```

```
<210> SEQ ID NO 60
<211> LENGTH: 9
<212> TYPE: PRT
<213> ORGANISM: Artificial Sequence
<220> FEATURE:
<223> OTHER INFORMATION: trafficking sequence TAT(s2-9)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 60

Arg Lys Lys Asp Arg Gln Arg Arg Arg
1               5

<210> SEQ ID NO 61
<211> LENGTH: 9
<212> TYPE: PRT
<213> ORGANISM: Artificial Sequence
<220> FEATURE:
<223> OTHER INFORMATION: trafficking sequence TAT(s2-10)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 61

Arg Lys Lys Arg Arg Asp Arg Arg Arg
1               5

<210> SEQ ID NO 62
<211> LENGTH: 9
<212> TYPE: PRT
<213> ORGANISM: Artificial Sequence
<220> FEATURE:
<223> OTHER INFORMATION: trafficking sequence TAT(s2-11)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 62

Arg Lys Lys Arg Arg Gln Asp Arg Arg
1               5

<210> SEQ ID NO 63
<211> LENGTH: 9
<212> TYPE: PRT
<213> ORGANISM: Artificial Sequence
```

```
<220> FEATURE:
<223> OTHER INFORMATION: trafficking sequence TAT(s2-12)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 63

Arg Lys Lys Arg Arg Gln Arg Asp Arg
1               5

<210> SEQ ID NO 64
<211> LENGTH: 9
<212> TYPE: PRT
<213> ORGANISM: Artificial Sequence
<220> FEATURE:
<223> OTHER INFORMATION: trafficking sequence TAT(s2-13)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 64

Arg Glu Lys Arg Arg Gln Arg Arg Arg
1               5

<210> SEQ ID NO 65
<211> LENGTH: 9
<212> TYPE: PRT
<213> ORGANISM: Artificial Sequence
<220> FEATURE:
<223> OTHER INFORMATION: trafficking sequence TAT(s2-14)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 65

Arg Lys Glu Arg Arg Gln Arg Arg Arg
1               5

<210> SEQ ID NO 66
<211> LENGTH: 9
<212> TYPE: PRT
<213> ORGANISM: Artificial Sequence
<220> FEATURE:
<223> OTHER INFORMATION: trafficking sequence TAT(s2-15)
<220> FEATURE:
<221> NAME/KEY: Variant
```

```
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 66

Arg Lys Lys Glu Arg Gln Arg Arg Arg
1               5

<210> SEQ ID NO 67
<211> LENGTH: 9
<212> TYPE: PRT
<213> ORGANISM: Artificial Sequence
<220> FEATURE:
<223> OTHER INFORMATION: trafficking sequence TAT(s2-16)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 67

Arg Lys Lys Arg Arg Glu Arg Arg Arg
1               5

<210> SEQ ID NO 68
<211> LENGTH: 9
<212> TYPE: PRT
<213> ORGANISM: Artificial Sequence
<220> FEATURE:
<223> OTHER INFORMATION: trafficking sequence TAT(s2-17)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 68

Arg Lys Lys Arg Arg Gln Glu Arg Arg
1               5

<210> SEQ ID NO 69
<211> LENGTH: 9
<212> TYPE: PRT
<213> ORGANISM: Artificial Sequence
<220> FEATURE:
<223> OTHER INFORMATION: trafficking sequence TAT(s2-18)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
```

-continued

```
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 69

Arg Lys Lys Arg Arg Gln Arg Glu Arg
1               5

<210> SEQ ID NO 70
<211> LENGTH: 9
<212> TYPE: PRT
<213> ORGANISM: Artificial Sequence
<220> FEATURE:
<223> OTHER INFORMATION: trafficking sequence TAT(s2-19)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 70

Arg Phe Lys Arg Arg Gln Arg Arg Arg
1               5

<210> SEQ ID NO 71
<211> LENGTH: 9
<212> TYPE: PRT
<213> ORGANISM: Artificial Sequence
<220> FEATURE:
<223> OTHER INFORMATION: trafficking sequence TAT(s2-20)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 71

Arg Lys Phe Arg Arg Gln Arg Arg Arg
1               5

<210> SEQ ID NO 72
<211> LENGTH: 9
<212> TYPE: PRT
<213> ORGANISM: Artificial Sequence
<220> FEATURE:
<223> OTHER INFORMATION: trafficking sequence TAT(s2-21)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
```

```
<222> LOCATION: (9)..(9)
<223> OTHER INFORMATION: Arg is D-enantiomeric Arg

<400> SEQUENCE: 72

Arg Lys Lys Phe Arg Gln Arg Arg Arg
1               5

<210> SEQ ID NO 73
<211> LENGTH: 9
<212> TYPE: PRT
<213> ORGANISM: Artificial Sequence
<220> FEATURE:
<223> OTHER INFORMATION: trafficking sequence TAT(s2-22)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 73

Arg Lys Lys Arg Arg Phe Arg Arg Arg
1               5

<210> SEQ ID NO 74
<211> LENGTH: 9
<212> TYPE: PRT
<213> ORGANISM: Artificial Sequence
<220> FEATURE:
<223> OTHER INFORMATION: trafficking sequence TAT(s2-23)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 74

Arg Lys Lys Arg Arg Gln Phe Arg Arg
1               5

<210> SEQ ID NO 75
<211> LENGTH: 9
<212> TYPE: PRT
<213> ORGANISM: Artificial Sequence
<220> FEATURE:
<223> OTHER INFORMATION: trafficking sequence TAT(s2-24)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 75
```

```
Arg Lys Lys Arg Arg Gln Arg Phe Arg
1               5

<210> SEQ ID NO 76
<211> LENGTH: 9
<212> TYPE: PRT
<213> ORGANISM: Artificial Sequence
<220> FEATURE:
<223> OTHER INFORMATION: trafficking sequence TAT(s2-25)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 76

Arg Arg Lys Arg Arg Gln Arg Arg Arg
1               5

<210> SEQ ID NO 77
<211> LENGTH: 9
<212> TYPE: PRT
<213> ORGANISM: Artificial Sequence
<220> FEATURE:
<223> OTHER INFORMATION: trafficking sequence TAT(s2-26)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 77

Arg Lys Arg Arg Arg Gln Arg Arg Arg
1               5

<210> SEQ ID NO 78
<211> LENGTH: 9
<212> TYPE: PRT
<213> ORGANISM: Artificial Sequence
<220> FEATURE:
<223> OTHER INFORMATION: trafficking sequence TAT(s2-27)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 78

Arg Lys Lys Lys Arg Gln Arg Arg Arg
1               5
```

```
<210> SEQ ID NO 79
<211> LENGTH: 9
<212> TYPE: PRT
<213> ORGANISM: Artificial Sequence
<220> FEATURE:
<223> OTHER INFORMATION: trafficking sequence TAT(s2-28)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 79

Arg Lys Lys Arg Arg Arg Arg Arg Arg
1               5

<210> SEQ ID NO 80
<211> LENGTH: 9
<212> TYPE: PRT
<213> ORGANISM: Artificial Sequence
<220> FEATURE:
<223> OTHER INFORMATION: trafficking sequence TAT(s2-29)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 80

Arg Lys Lys Arg Arg Gln Lys Arg Arg
1               5

<210> SEQ ID NO 81
<211> LENGTH: 9
<212> TYPE: PRT
<213> ORGANISM: Artificial Sequence
<220> FEATURE:
<223> OTHER INFORMATION: trafficking sequence TAT(s2-30)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 81

Arg Lys Lys Arg Arg Gln Arg Lys Arg
1               5

<210> SEQ ID NO 82
<211> LENGTH: 9
<212> TYPE: PRT
```

```
<213> ORGANISM: Artificial Sequence
<220> FEATURE:
<223> OTHER INFORMATION: trafficking sequence TAT(s2-31)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 82

Arg His Lys Arg Arg Gln Arg Arg Arg
1               5

<210> SEQ ID NO 83
<211> LENGTH: 9
<212> TYPE: PRT
<213> ORGANISM: Artificial Sequence
<220> FEATURE:
<223> OTHER INFORMATION: trafficking sequence TAT(s2-32)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 83

Arg Lys His Arg Arg Gln Arg Arg Arg
1               5

<210> SEQ ID NO 84
<211> LENGTH: 9
<212> TYPE: PRT
<213> ORGANISM: Artificial Sequence
<220> FEATURE:
<223> OTHER INFORMATION: trafficking sequence TAT(s2-33)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 84

Arg Lys Lys His Arg Gln Arg Arg Arg
1               5

<210> SEQ ID NO 85
<211> LENGTH: 9
<212> TYPE: PRT
<213> ORGANISM: Artificial Sequence
<220> FEATURE:
<223> OTHER INFORMATION: trafficking sequence TAT(s2-34)
<220> FEATURE:
```

-continued

```
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 85

Arg Lys Lys Arg Arg His Arg Arg Arg
1               5

<210> SEQ ID NO 86
<211> LENGTH: 9
<212> TYPE: PRT
<213> ORGANISM: Artificial Sequence
<220> FEATURE:
<223> OTHER INFORMATION: trafficking sequence TAT(s2-35)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 86

Arg Lys Lys Arg Arg Gln His Arg Arg
1               5

<210> SEQ ID NO 87
<211> LENGTH: 9
<212> TYPE: PRT
<213> ORGANISM: Artificial Sequence
<220> FEATURE:
<223> OTHER INFORMATION: trafficking sequence TAT(s2-36)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 87

Arg Lys Lys Arg Arg Gln Arg His Arg
1               5

<210> SEQ ID NO 88
<211> LENGTH: 9
<212> TYPE: PRT
<213> ORGANISM: Artificial Sequence
<220> FEATURE:
<223> OTHER INFORMATION: trafficking sequence TAT(s2-37)
<220> FEATURE:
<221> NAME/KEY: Variant
<222> LOCATION: (1)..(1)
<223> OTHER INFORMATION: Arg is D-enantiomeric Arg
<220> FEATURE:
```

```
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 88

Arg Ile Lys Arg Arg Gln Arg Arg Arg
1               5

<210> SEQ ID NO 89
<211> LENGTH: 9
<212> TYPE: PRT
<213> ORGANISM: Artificial Sequence
<220> FEATURE:
<223> OTHER INFORMATION: trafficking sequence TAT(s2-38)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 89

Arg Lys Ile Arg Arg Gln Arg Arg Arg
1               5

<210> SEQ ID NO 90
<211> LENGTH: 9
<212> TYPE: PRT
<213> ORGANISM: Artificial Sequence
<220> FEATURE:
<223> OTHER INFORMATION: trafficking sequence TAT(s2-39)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 90

Arg Lys Lys Ile Arg Gln Arg Arg Arg
1               5

<210> SEQ ID NO 91
<211> LENGTH: 9
<212> TYPE: PRT
<213> ORGANISM: Artificial Sequence
<220> FEATURE:
<223> OTHER INFORMATION: trafficking sequence TAT(s2-40)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
```

<221> NAME/KEY: Variant
<222> LOCATION: (9)..(9)
<223> OTHER INFORMATION: Arg is D-enantiomeric Arg

<400> SEQUENCE: 91

Arg Lys Lys Arg Arg Ile Arg Arg Arg
1               5

<210> SEQ ID NO 92
<211> LENGTH: 9
<212> TYPE: PRT
<213> ORGANISM: Artificial Sequence
<220> FEATURE:
<223> OTHER INFORMATION: trafficking sequence TAT(s2-41)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 92

Arg Lys Lys Arg Arg Gln Ile Arg Arg
1               5

<210> SEQ ID NO 93
<211> LENGTH: 9
<212> TYPE: PRT
<213> ORGANISM: Artificial Sequence
<220> FEATURE:
<223> OTHER INFORMATION: trafficking sequence TAT(s2-42)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 93

Arg Lys Lys Arg Arg Gln Arg Ile Arg
1               5

<210> SEQ ID NO 94
<211> LENGTH: 9
<212> TYPE: PRT
<213> ORGANISM: Artificial Sequence
<220> FEATURE:
<223> OTHER INFORMATION: trafficking sequence TAT(s2-43)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

```
<400> SEQUENCE: 94

Arg Leu Lys Arg Arg Gln Arg Arg Arg
1               5

<210> SEQ ID NO 95
<211> LENGTH: 9
<212> TYPE: PRT
<213> ORGANISM: Artificial Sequence
<220> FEATURE:
<223> OTHER INFORMATION: trafficking sequence TAT(s2-44)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 95

Arg Lys Leu Arg Arg Gln Arg Arg Arg
1               5

<210> SEQ ID NO 96
<211> LENGTH: 9
<212> TYPE: PRT
<213> ORGANISM: Artificial Sequence
<220> FEATURE:
<223> OTHER INFORMATION: trafficking sequence TAT(s2-45)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 96

Arg Lys Lys Leu Arg Gln Arg Arg Arg
1               5

<210> SEQ ID NO 97
<211> LENGTH: 9
<212> TYPE: PRT
<213> ORGANISM: Artificial Sequence
<220> FEATURE:
<223> OTHER INFORMATION: trafficking sequence TAT(s2-46)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 97

Arg Lys Lys Arg Arg Leu Arg Arg Arg
1               5
```

<210> SEQ ID NO 98
<211> LENGTH: 9
<212> TYPE: PRT
<213> ORGANISM: Artificial Sequence
<220> FEATURE:
<223> OTHER INFORMATION: trafficking sequence TAT(s2-47)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 98

Arg Lys Lys Arg Arg Gln Leu Arg Arg
1               5

<210> SEQ ID NO 99
<211> LENGTH: 9
<212> TYPE: PRT
<213> ORGANISM: Artificial Sequence
<220> FEATURE:
<223> OTHER INFORMATION: trafficking sequence TAT(s2-48)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 99

Arg Lys Lys Arg Arg Gln Arg Leu Arg
1               5

<210> SEQ ID NO 100
<211> LENGTH: 9
<212> TYPE: PRT
<213> ORGANISM: Artificial Sequence
<220> FEATURE:
<223> OTHER INFORMATION: trafficking sequence TAT(s2-49)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 100

Arg Met Lys Arg Arg Gln Arg Arg Arg
1               5

<210> SEQ ID NO 101
<211> LENGTH: 9

```
<212> TYPE: PRT
<213> ORGANISM: Artificial Sequence
<220> FEATURE:
<223> OTHER INFORMATION: trafficking sequence TAT(s2-50)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 101

Arg Lys Met Arg Arg Gln Arg Arg Arg
1               5

<210> SEQ ID NO 102
<211> LENGTH: 9
<212> TYPE: PRT
<213> ORGANISM: Artificial Sequence
<220> FEATURE:
<223> OTHER INFORMATION: trafficking sequence TAT(s2-51)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 102

Arg Lys Lys Met Arg Gln Arg Arg Arg
1               5

<210> SEQ ID NO 103
<211> LENGTH: 9
<212> TYPE: PRT
<213> ORGANISM: Artificial Sequence
<220> FEATURE:
<223> OTHER INFORMATION: trafficking sequence TAT(s2-52)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 103

Arg Lys Lys Arg Arg Met Arg Arg Arg
1               5

<210> SEQ ID NO 104
<211> LENGTH: 9
<212> TYPE: PRT
<213> ORGANISM: Artificial Sequence
<220> FEATURE:
<223> OTHER INFORMATION: trafficking sequence TAT(s2-53)
```

```
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 104

Arg Lys Lys Arg Arg Gln Met Arg Arg
1               5

<210> SEQ ID NO 105
<211> LENGTH: 9
<212> TYPE: PRT
<213> ORGANISM: Artificial Sequence
<220> FEATURE:
<223> OTHER INFORMATION: trafficking sequence TAT(s2-54)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 105

Arg Lys Lys Arg Arg Gln Arg Met Arg
1               5

<210> SEQ ID NO 106
<211> LENGTH: 9
<212> TYPE: PRT
<213> ORGANISM: Artificial Sequence
<220> FEATURE:
<223> OTHER INFORMATION: trafficking sequence TAT(s2-55)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 106

Arg Asn Lys Arg Arg Gln Arg Arg Arg
1               5

<210> SEQ ID NO 107
<211> LENGTH: 9
<212> TYPE: PRT
<213> ORGANISM: Artificial Sequence
<220> FEATURE:
<223> OTHER INFORMATION: trafficking sequence TAT(s2-56)
<220> FEATURE:
<221> NAME/KEY: Variant
<222> LOCATION: (1)..(1)
<223> OTHER INFORMATION: Arg is D-enantiomeric Arg
```

-continued

```
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 107

Arg Lys Asn Arg Arg Gln Arg Arg Arg
1               5

<210> SEQ ID NO 108
<211> LENGTH: 9
<212> TYPE: PRT
<213> ORGANISM: Artificial Sequence
<220> FEATURE:
<223> OTHER INFORMATION: trafficking sequence TAT(s2-57)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 108

Arg Lys Lys Asn Arg Gln Arg Arg Arg
1               5

<210> SEQ ID NO 109
<211> LENGTH: 9
<212> TYPE: PRT
<213> ORGANISM: Artificial Sequence
<220> FEATURE:
<223> OTHER INFORMATION: trafficking sequence TAT(s2-58)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 109

Arg Lys Lys Arg Arg Asn Arg Arg Arg
1               5

<210> SEQ ID NO 110
<211> LENGTH: 9
<212> TYPE: PRT
<213> ORGANISM: Artificial Sequence
<220> FEATURE:
<223> OTHER INFORMATION: trafficking sequence TAT(s2-59)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
```

```
<220> FEATURE:
<221> NAME/KEY: Variant
<222> LOCATION: (9)..(9)
<223> OTHER INFORMATION: Arg is D-enantiomeric Arg

<400> SEQUENCE: 110

Arg Lys Lys Arg Arg Gln Asn Arg Arg
1               5

<210> SEQ ID NO 111
<211> LENGTH: 9
<212> TYPE: PRT
<213> ORGANISM: Artificial Sequence
<220> FEATURE:
<223> OTHER INFORMATION: trafficking sequence TAT(s2-60)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 111

Arg Lys Lys Arg Arg Gln Arg Asn Arg
1               5

<210> SEQ ID NO 112
<211> LENGTH: 9
<212> TYPE: PRT
<213> ORGANISM: Artificial Sequence
<220> FEATURE:
<223> OTHER INFORMATION: trafficking sequence TAT(s2-61)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 112

Arg Gln Lys Arg Arg Gln Arg Arg Arg
1               5

<210> SEQ ID NO 113
<211> LENGTH: 9
<212> TYPE: PRT
<213> ORGANISM: Artificial Sequence
<220> FEATURE:
<223> OTHER INFORMATION: trafficking sequence TAT(s2-62)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
```

-continued

```
<400> SEQUENCE: 113

Arg Lys Gln Arg Arg Gln Arg Arg Arg
1               5

<210> SEQ ID NO 114
<211> LENGTH: 9
<212> TYPE: PRT
<213> ORGANISM: Artificial Sequence
<220> FEATURE:
<223> OTHER INFORMATION: trafficking sequence TAT(s2-63)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 114

Arg Lys Lys Gln Arg Gln Arg Arg Arg
1               5

<210> SEQ ID NO 115
<211> LENGTH: 9
<212> TYPE: PRT
<213> ORGANISM: Artificial Sequence
<220> FEATURE:
<223> OTHER INFORMATION: trafficking sequence TAT(s2-64)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 115

Arg Lys Lys Arg Arg Lys Arg Arg Arg
1               5

<210> SEQ ID NO 116
<211> LENGTH: 9
<212> TYPE: PRT
<213> ORGANISM: Artificial Sequence
<220> FEATURE:
<223> OTHER INFORMATION: trafficking sequence TAT(s2-65)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 116

Arg Lys Lys Arg Arg Gln Gln Arg Arg
```

```
<210> SEQ ID NO 117
<211> LENGTH: 9
<212> TYPE: PRT
<213> ORGANISM: Artificial Sequence
<220> FEATURE:
<223> OTHER INFORMATION: trafficking sequence TAT(s2-66)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 117

Arg Lys Lys Arg Arg Gln Arg Gln Arg
1               5

<210> SEQ ID NO 118
<211> LENGTH: 9
<212> TYPE: PRT
<213> ORGANISM: Artificial Sequence
<220> FEATURE:
<223> OTHER INFORMATION: trafficking sequence TAT(s2-67)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 118

Arg Ser Lys Arg Arg Gln Arg Arg Arg
1               5

<210> SEQ ID NO 119
<211> LENGTH: 9
<212> TYPE: PRT
<213> ORGANISM: Artificial Sequence
<220> FEATURE:
<223> OTHER INFORMATION: trafficking sequence TAT(s2-68)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 119

Arg Lys Ser Arg Arg Gln Arg Arg Arg
1               5

<210> SEQ ID NO 120
```

```
<211> LENGTH: 9
<212> TYPE: PRT
<213> ORGANISM: Artificial Sequence
<220> FEATURE:
<223> OTHER INFORMATION: trafficking sequence TAT(s2-69)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 120

Arg Lys Lys Ser Arg Gln Arg Arg Arg
1               5

<210> SEQ ID NO 121
<211> LENGTH: 9
<212> TYPE: PRT
<213> ORGANISM: Artificial Sequence
<220> FEATURE:
<223> OTHER INFORMATION: trafficking sequence TAT(s2-70)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 121

Arg Lys Lys Arg Arg Ser Arg Arg Arg
1               5

<210> SEQ ID NO 122
<211> LENGTH: 9
<212> TYPE: PRT
<213> ORGANISM: Artificial Sequence
<220> FEATURE:
<223> OTHER INFORMATION: trafficking sequence TAT(s2-71)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 122

Arg Lys Lys Arg Arg Gln Ser Arg Arg
1               5

<210> SEQ ID NO 123
<211> LENGTH: 9
<212> TYPE: PRT
<213> ORGANISM: Artificial Sequence
<220> FEATURE:
```

```
<223> OTHER INFORMATION: trafficking sequence TAT(s2-72)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 123

Arg Lys Lys Arg Arg Gln Arg Ser Arg
1               5

<210> SEQ ID NO 124
<211> LENGTH: 9
<212> TYPE: PRT
<213> ORGANISM: Artificial Sequence
<220> FEATURE:
<223> OTHER INFORMATION: trafficking sequence TAT(s2-73)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 124

Arg Thr Lys Arg Arg Gln Arg Arg Arg
1               5

<210> SEQ ID NO 125
<211> LENGTH: 9
<212> TYPE: PRT
<213> ORGANISM: Artificial Sequence
<220> FEATURE:
<223> OTHER INFORMATION: trafficking sequence TAT(s2-74)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 125

Arg Lys Thr Arg Arg Gln Arg Arg Arg
1               5

<210> SEQ ID NO 126
<211> LENGTH: 9
<212> TYPE: PRT
<213> ORGANISM: Artificial Sequence
<220> FEATURE:
<223> OTHER INFORMATION: trafficking sequence TAT(s2-75)
<220> FEATURE:
<221> NAME/KEY: Variant
<222> LOCATION: (1)..(1)
```

```
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 126

Arg Lys Lys Thr Arg Gln Arg Arg Arg
1               5

<210> SEQ ID NO 127
<211> LENGTH: 9
<212> TYPE: PRT
<213> ORGANISM: Artificial Sequence
<220> FEATURE:
<223> OTHER INFORMATION: trafficking sequence TAT(s2-76)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 127

Arg Lys Lys Arg Arg Thr Arg Arg Arg
1               5

<210> SEQ ID NO 128
<211> LENGTH: 9
<212> TYPE: PRT
<213> ORGANISM: Artificial Sequence
<220> FEATURE:
<223> OTHER INFORMATION: trafficking sequence TAT(s2-77)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 128

Arg Lys Lys Arg Arg Gln Thr Arg Arg
1               5

<210> SEQ ID NO 129
<211> LENGTH: 9
<212> TYPE: PRT
<213> ORGANISM: Artificial Sequence
<220> FEATURE:
<223> OTHER INFORMATION: trafficking sequence TAT(s2-78)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
```

```
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 129

Arg Lys Lys Arg Arg Gln Arg Thr Arg
1               5

<210> SEQ ID NO 130
<211> LENGTH: 9
<212> TYPE: PRT
<213> ORGANISM: Artificial Sequence
<220> FEATURE:
<223> OTHER INFORMATION: trafficking sequence TAT(s2-79)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 130

Arg Val Lys Arg Arg Gln Arg Arg Arg
1               5

<210> SEQ ID NO 131
<211> LENGTH: 9
<212> TYPE: PRT
<213> ORGANISM: Artificial Sequence
<220> FEATURE:
<223> OTHER INFORMATION: trafficking sequence TAT(s2-80)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 131

Arg Lys Val Arg Arg Gln Arg Arg Arg
1               5

<210> SEQ ID NO 132
<211> LENGTH: 9
<212> TYPE: PRT
<213> ORGANISM: Artificial Sequence
<220> FEATURE:
<223> OTHER INFORMATION: trafficking sequence TAT(s2-81)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
```

```
<223> OTHER INFORMATION: Arg is D-enantiomeric Arg

<400> SEQUENCE: 132

Arg Lys Lys Val Arg Gln Arg Arg Arg
1               5

<210> SEQ ID NO 133
<211> LENGTH: 9
<212> TYPE: PRT
<213> ORGANISM: Artificial Sequence
<220> FEATURE:
<223> OTHER INFORMATION: trafficking sequence TAT(s2-82)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 133

Arg Lys Lys Arg Arg Val Arg Arg Arg
1               5

<210> SEQ ID NO 134
<211> LENGTH: 9
<212> TYPE: PRT
<213> ORGANISM: Artificial Sequence
<220> FEATURE:
<223> OTHER INFORMATION: trafficking sequence TAT(s2-83)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 134

Arg Lys Lys Arg Arg Gln Val Arg Arg
1               5

<210> SEQ ID NO 135
<211> LENGTH: 9
<212> TYPE: PRT
<213> ORGANISM: Artificial Sequence
<220> FEATURE:
<223> OTHER INFORMATION: trafficking sequence TAT(s2-84)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 135
```

```
Arg Lys Lys Arg Arg Gln Arg Val Arg
1               5
```

<210> SEQ ID NO 136
<211> LENGTH: 9
<212> TYPE: PRT
<213> ORGANISM: Artificial Sequence
<220> FEATURE:
<223> OTHER INFORMATION: trafficking sequence TAT(s2-85)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 136

```
Arg Trp Lys Arg Arg Gln Arg Arg Arg
1               5
```

<210> SEQ ID NO 137
<211> LENGTH: 9
<212> TYPE: PRT
<213> ORGANISM: Artificial Sequence
<220> FEATURE:
<223> OTHER INFORMATION: trafficking sequence TAT(s2-86)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 137

```
Arg Lys Trp Arg Arg Gln Arg Arg Arg
1               5
```

<210> SEQ ID NO 138
<211> LENGTH: 9
<212> TYPE: PRT
<213> ORGANISM: Artificial Sequence
<220> FEATURE:
<223> OTHER INFORMATION: trafficking sequence TAT(s2-87)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 138

```
Arg Lys Lys Trp Arg Gln Arg Arg Arg
1               5
```

```
<210> SEQ ID NO 139
<211> LENGTH: 9
<212> TYPE: PRT
<213> ORGANISM: Artificial Sequence
<220> FEATURE:
<223> OTHER INFORMATION: trafficking sequence TAT(s2-88)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 139

Arg Lys Lys Arg Arg Trp Arg Arg Arg
1               5

<210> SEQ ID NO 140
<211> LENGTH: 9
<212> TYPE: PRT
<213> ORGANISM: Artificial Sequence
<220> FEATURE:
<223> OTHER INFORMATION: trafficking sequence TAT(s2-89)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 140

Arg Lys Lys Arg Arg Gln Trp Arg Arg
1               5

<210> SEQ ID NO 141
<211> LENGTH: 9
<212> TYPE: PRT
<213> ORGANISM: Artificial Sequence
<220> FEATURE:
<223> OTHER INFORMATION: trafficking sequence TAT(s2-90)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 141

Arg Lys Lys Arg Arg Gln Arg Trp Arg
1               5

<210> SEQ ID NO 142
<211> LENGTH: 9
<212> TYPE: PRT
<213> ORGANISM: Artificial Sequence
```

```
<220> FEATURE:
<223> OTHER INFORMATION: trafficking sequence TAT(s2-91)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 142

Arg Tyr Lys Arg Arg Gln Arg Arg Arg
1               5

<210> SEQ ID NO 143
<211> LENGTH: 9
<212> TYPE: PRT
<213> ORGANISM: Artificial Sequence
<220> FEATURE:
<223> OTHER INFORMATION: trafficking sequence TAT(s2-92)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 143

Arg Lys Tyr Arg Arg Gln Arg Arg Arg
1               5

<210> SEQ ID NO 144
<211> LENGTH: 9
<212> TYPE: PRT
<213> ORGANISM: Artificial Sequence
<220> FEATURE:
<223> OTHER INFORMATION: trafficking sequence TAT(s2-93)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 144

Arg Lys Lys Tyr Arg Gln Arg Arg Arg
1               5

<210> SEQ ID NO 145
<211> LENGTH: 9
<212> TYPE: PRT
<213> ORGANISM: Artificial Sequence
<220> FEATURE:
<223> OTHER INFORMATION: trafficking sequence TAT(s2-94)
<220> FEATURE:
<221> NAME/KEY: Variant
```

```
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 145

Arg Lys Lys Arg Arg Tyr Arg Arg Arg
 1               5

<210> SEQ ID NO 146
<211> LENGTH: 9
<212> TYPE: PRT
<213> ORGANISM: Artificial Sequence
<220> FEATURE:
<223> OTHER INFORMATION: trafficking sequence TAT(s2-95)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 146

Arg Lys Lys Arg Arg Gln Tyr Arg Arg
 1               5

<210> SEQ ID NO 147
<211> LENGTH: 9
<212> TYPE: PRT
<213> ORGANISM: Artificial Sequence
<220> FEATURE:
<223> OTHER INFORMATION: Trafficking sequence TAT(s2-96)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 147

Arg Lys Lys Arg Arg Gln Arg Tyr Arg
 1               5

<210> SEQ ID NO 148
<211> LENGTH: 8
<212> TYPE: PRT
<213> ORGANISM: Artificial
<220> FEATURE:
<223> OTHER INFORMATION: Trafficking sequence TAT(s2-97)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
```

```
<222> LOCATION: (5)..(5)
<223> OTHER INFORMATION: Arg is D-enantiomeric Arg
<220> FEATURE:
<221> NAME/KEY: Variant
<222> LOCATION: (8)..(8)
<223> OTHER INFORMATION: Arg is D-enantiomeric Arg

<400> SEQUENCE: 148

Arg Lys Lys Arg Arg Gln Arg Arg
1               5

<210> SEQ ID NO 149
<211> LENGTH: 9
<212> TYPE: PRT
<213> ORGANISM: Artificial
<220> FEATURE:
<223> OTHER INFORMATION: Trafficking sequence TAT(s2-98)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (8)..(8)
<223> OTHER INFORMATION: Arg is D-enantiomeric Arg

<400> SEQUENCE: 149

Arg Lys Lys Arg Arg Gln Arg Arg Lys
1               5

<210> SEQ ID NO 150
<211> LENGTH: 9
<212> TYPE: PRT
<213> ORGANISM: Artificial
<220> FEATURE:
<223> OTHER INFORMATION: Trafficking sequence TAT(s2-99)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (8)..(8)
<223> OTHER INFORMATION: Arg is D-enantiomeric Arg

<400> SEQUENCE: 150

Arg Lys Lys Arg Arg Gln Arg Arg Arg
1               5

<210> SEQ ID NO 151
<211> LENGTH: 9
<212> TYPE: PRT
<213> ORGANISM: Artificial Sequence
<220> FEATURE:
<223> OTHER INFORMATION: trafficking sequence r3R6
<220> FEATURE:
<221> NAME/KEY: VARIANT
<222> LOCATION: (1)..(1)
<223> OTHER INFORMATION: /replace="D-enatiomeric amino acid arginine"
<220> FEATURE:
<221> NAME/KEY: VARIANT
<222> LOCATION: (5)..(5)
<223> OTHER INFORMATION: /replace="D-enatiomeric amino acid arginine"
<220> FEATURE:
<221> NAME/KEY: VARIANT
```

```
<222> LOCATION: (9)..(9)
<223> OTHER INFORMATION: /replace="D-enatiomeric amino acid arginine"

<400> SEQUENCE: 151

Arg Arg Arg Arg Arg Arg Arg Arg Arg
1               5

<210> SEQ ID NO 152
<211> LENGTH: 9
<212> TYPE: PRT
<213> ORGANISM: Artificial Sequence
<220> FEATURE:
<223> OTHER INFORMATION: trafficking sequence L-R9

<400> SEQUENCE: 152

Arg Arg Arg Arg Arg Arg Arg Arg Arg
1               5

<210> SEQ ID NO 153
<211> LENGTH: 8
<212> TYPE: PRT
<213> ORGANISM: Artificial Sequence
<220> FEATURE:
<223> OTHER INFORMATION: trafficking sequence L-R8

<400> SEQUENCE: 153

Arg Arg Arg Arg Arg Arg Arg Arg
1               5

<210> SEQ ID NO 154
<211> LENGTH: 7
<212> TYPE: PRT
<213> ORGANISM: Artificial Sequence
<220> FEATURE:
<223> OTHER INFORMATION: trafficking sequence L-R7

<400> SEQUENCE: 154

Arg Arg Arg Arg Arg Arg Arg
1               5

<210> SEQ ID NO 155
<211> LENGTH: 6
<212> TYPE: PRT
<213> ORGANISM: Artificial Sequence
<220> FEATURE:
<223> OTHER INFORMATION: trafficking sequence L-R6

<400> SEQUENCE: 155

Arg Arg Arg Arg Arg Arg
1               5

<210> SEQ ID NO 156
<211> LENGTH: 5
<212> TYPE: PRT
<213> ORGANISM: Artificial Sequence
<220> FEATURE:
<223> OTHER INFORMATION: trafficking sequence L-R5

<400> SEQUENCE: 156

Arg Arg Arg Arg Arg
1               5

<210> SEQ ID NO 157
<211> LENGTH: 9
<212> TYPE: PRT
<213> ORGANISM: Artificial
<220> FEATURE:
```

```
<223> OTHER INFORMATION: all D transporter construct (all amino acid
      residues are D-amino acids)
<220> FEATURE:
<221> NAME/KEY: Variant
<222> LOCATION: (1)..(9)
<223> OTHER INFORMATION: Arg is D-enantiomeric Arg

<400> SEQUENCE: 157

Arg Arg Arg Arg Arg Arg Arg Arg Arg
1               5

<210> SEQ ID NO 158
<211> LENGTH: 9
<212> TYPE: PRT
<213> ORGANISM: Artificial
<220> FEATURE:
<223> OTHER INFORMATION: Description of sequence: D/L transporter
      construct (D and L amino acid residues alternate, beginning wit
      D amino acids)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (3)..(3)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (7)..(7)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 158

Arg Arg Arg Arg Arg Arg Arg Arg Arg
1               5

<210> SEQ ID NO 159
<211> LENGTH: 9
<212> TYPE: PRT
<213> ORGANISM: Artificial
<220> FEATURE:
<223> OTHER INFORMATION: Description of sequence: DD/LL transporter
      construct
<220> FEATURE:
<221> NAME/KEY: Variant
<222> LOCATION: (1)..(2)
<223> OTHER INFORMATION: Arg is D-enantiomeric Arg
<220> FEATURE:
<221> NAME/KEY: Variant
<222> LOCATION: (5)..(6)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 159

Arg Arg Arg Arg Arg Arg Arg Arg Arg
1               5

<210> SEQ ID NO 160
<211> LENGTH: 11
<212> TYPE: PRT
<213> ORGANISM: Artificial Sequence
<220> FEATURE:
```

```
<223> OTHER INFORMATION: trafficking sequence PTD-4

<400> SEQUENCE: 160

Tyr Ala Arg Ala Ala Ala Arg Gln Ala Arg Ala
1               5                   10

<210> SEQ ID NO 161
<211> LENGTH: 11
<212> TYPE: PRT
<213> ORGANISM: Artificial Sequence
<220> FEATURE:
<223> OTHER INFORMATION: trafficking sequence PTD-4

<400> SEQUENCE: 161

Trp Ala Arg Ala Ala Ala Arg Gln Ala Arg Ala
1               5                   10

<210> SEQ ID NO 162
<211> LENGTH: 11
<212> TYPE: PRT
<213> ORGANISM: Artificial Sequence
<220> FEATURE:
<223> OTHER INFORMATION: trafficking sequence PTD-4

<400> SEQUENCE: 162

Trp Ala Arg Ala Gln Arg Ala Ala Ala Arg Ala
1               5                   10

<210> SEQ ID NO 163
<211> LENGTH: 16
<212> TYPE: PRT
<213> ORGANISM: Artificial Sequence
<220> FEATURE:
<223> OTHER INFORMATION: trafficking sequence L-P1 (Penetratin)

<400> SEQUENCE: 163

Arg Gln Val Lys Val Trp Phe Gln Asn Arg Arg Met Lys Trp Lys Lys
1               5                   10                  15

<210> SEQ ID NO 164
<211> LENGTH: 16
<212> TYPE: PRT
<213> ORGANISM: Artificial Sequence
<220> FEATURE:
<223> OTHER INFORMATION: trafficking sequence D-P1 (Penetratin)

<400> SEQUENCE: 164

Lys Lys Trp Lys Met Arg Arg Asn Gln Phe Trp Val Lys Val Gln Arg
1               5                   10                  15

<210> SEQ ID NO 165
<211> LENGTH: 17
<212> TYPE: PRT
<213> ORGANISM: Artificial Sequence
<220> FEATURE:
<223> OTHER INFORMATION: trafficking sequence JNK1, bestfit

<400> SEQUENCE: 165

Trp Lys Arg Ala Ala Ala Arg Lys Ala Arg Ala Met Ser Leu Asn Leu
1               5                   10                  15

Phe

<210> SEQ ID NO 166
<211> LENGTH: 17
<212> TYPE: PRT
<213> ORGANISM: Artificial Sequence
```

-continued

```
<220> FEATURE:
<223> OTHER INFORMATION: trafficking sequence JNK1, bestfit (variant 1)

<400> SEQUENCE: 166

Trp Lys Arg Ala Ala Ala Arg Ala Ala Arg Ala Met Ser Leu Asn Leu
1               5                   10                  15
Phe

<210> SEQ ID NO 167
<211> LENGTH: 9
<212> TYPE: PRT
<213> ORGANISM: Artificial Sequence
<220> FEATURE:
<223> OTHER INFORMATION: trafficking sequence MDCK transcytose sequence

<400> SEQUENCE: 167

Arg Tyr Arg Gly Asp Leu Gly Arg Arg
1               5

<210> SEQ ID NO 168
<211> LENGTH: 4
<212> TYPE: PRT
<213> ORGANISM: Artificial Sequence
<220> FEATURE:
<223> OTHER INFORMATION: trafficking sequence YKGL

<400> SEQUENCE: 168

Tyr Lys Gly Leu
1

<210> SEQ ID NO 169
<211> LENGTH: 4
<212> TYPE: PRT
<213> ORGANISM: Artificial
<220> FEATURE:
<223> OTHER INFORMATION: trafficking sequence RRTK

<400> SEQUENCE: 169

Arg Arg Thr Lys
1

<210> SEQ ID NO 170
<211> LENGTH: 4
<212> TYPE: PRT
<213> ORGANISM: Artificial
<220> FEATURE:
<223> OTHER INFORMATION: trafficking sequence RRPK

<400> SEQUENCE: 170

Arg Arg Pro Lys
1

<210> SEQ ID NO 171
<211> LENGTH: 20
<212> TYPE: PRT
<213> ORGANISM: Artificial
<220> FEATURE:
<223> OTHER INFORMATION: rKKRrQRRrRPkRPTTLNLf JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
```

```
<222> LOCATION: (9)..(9)
<223> OTHER INFORMATION: Arg is D-enantiomeric Arg
<220> FEATURE:
<221> NAME/KEY: Variant
<222> LOCATION: (12)..(12)
<223> OTHER INFORMATION: Lys is D-enantiomeric Lys
<220> FEATURE:
<221> NAME/KEY: Variant
<222> LOCATION: (20)..(20)
<223> OTHER INFORMATION: Phe is D-enantiomeric Phe

<400> SEQUENCE: 171

Arg Lys Lys Arg Arg Gln Arg Arg Arg Pro Lys Arg Pro Thr Thr
1               5                   10                  15

Leu Asn Leu Phe
            20

<210> SEQ ID NO 172
<211> LENGTH: 20
<212> TYPE: PRT
<213> ORGANISM: Artificial
<220> FEATURE:
<223> OTHER INFORMATION: rKKRrQRRrRPkRPaTLNLf  JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (12)..(12)
<223> OTHER INFORMATION: Lys is D-enantiomeric Lys
<220> FEATURE:
<221> NAME/KEY: Variant
<222> LOCATION: (15)..(15)
<223> OTHER INFORMATION: Ala is D-enantiomeric Ala
<220> FEATURE:
<221> NAME/KEY: Variant
<222> LOCATION: (20)..(20)
<223> OTHER INFORMATION: Phe is D-enantiomeric Phe

<400> SEQUENCE: 172

Arg Lys Lys Arg Arg Gln Arg Arg Arg Pro Lys Arg Pro Ala Thr
1               5                   10                  15

Leu Asn Leu Phe
            20

<210> SEQ ID NO 173
<211> LENGTH: 20
<212> TYPE: PRT
<213> ORGANISM: Artificial
<220> FEATURE:
<223> OTHER INFORMATION: rKKRrQRRrRPkRPTTLrLf JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
```

```
<221> NAME/KEY: Variant
<222> LOCATION: (12)..(12)
<223> OTHER INFORMATION: Lys is D-enantiomeric Lys
<220> FEATURE:
<221> NAME/KEY: Variant
<222> LOCATION: (18)..(18)
<223> OTHER INFORMATION: Arg is D-enantiomeric Arg
<220> FEATURE:
<221> NAME/KEY: Variant
<222> LOCATION: (20)..(20)
<223> OTHER INFORMATION: Phe is D-enantiomeric Phe

<400> SEQUENCE: 173

Arg Lys Lys Arg Arg Gln Arg Arg Arg Pro Lys Arg Pro Thr Thr
1               5                   10                  15

Leu Arg Leu Phe
            20

<210> SEQ ID NO 174
<211> LENGTH: 17
<212> TYPE: PRT
<213> ORGANISM: Artificial
<220> FEATURE:
<223> OTHER INFORMATION: rKKRrQRRrRPTTLNLf JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (17)..(17)
<223> OTHER INFORMATION: Phe is D-enantiomeric Phe

<400> SEQUENCE: 174

Arg Lys Lys Arg Arg Gln Arg Arg Arg Pro Thr Thr Leu Asn Leu
1               5                   10                  15

Phe

<210> SEQ ID NO 175
<211> LENGTH: 16
<212> TYPE: PRT
<213> ORGANISM: Artificial
<220> FEATURE:
<223> OTHER INFORMATION: rKKRrQRrRPTTLNLf JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (8)..(8)
<223> OTHER INFORMATION: Arg is D-enantiomeric Arg
<220> FEATURE:
<221> NAME/KEY: Variant
<222> LOCATION: (16)..(16)
<223> OTHER INFORMATION: Phe is D-enantiomeric Phe

<400> SEQUENCE: 175

Arg Lys Lys Arg Arg Gln Arg Arg Pro Thr Thr Leu Asn Leu Phe
1               5                   10                  15
```

<210> SEQ ID NO 176
<211> LENGTH: 20
<212> TYPE: PRT
<213> ORGANISM: Artificial
<220> FEATURE:
<223> OTHER INFORMATION: rKKRrQRRrRPkRPTTLNLw JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (12)..(12)
<223> OTHER INFORMATION: Lys is D-enantiomeric Lys
<220> FEATURE:
<221> NAME/KEY: Variant
<222> LOCATION: (20)..(20)
<223> OTHER INFORMATION: Trp is D-enantiomeric Trp

<400> SEQUENCE: 176

Arg Lys Lys Arg Arg Gln Arg Arg Arg Pro Lys Arg Pro Thr Thr
1               5                   10                  15

Leu Asn Leu Trp
            20

<210> SEQ ID NO 177
<211> LENGTH: 20
<212> TYPE: PRT
<213> ORGANISM: Artificial
<220> FEATURE:
<223> OTHER INFORMATION: rKKRrQRRrRPkRPTDLNLf JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (12)..(12)
<223> OTHER INFORMATION: Lys is D-enantiomeric Lys
<220> FEATURE:
<221> NAME/KEY: Variant
<222> LOCATION: (20)..(20)
<223> OTHER INFORMATION: Phe is D-enantiomeric Phe

<400> SEQUENCE: 177

Arg Lys Lys Arg Arg Gln Arg Arg Arg Pro Lys Arg Pro Thr Asp
1               5                   10                  15

Leu Asn Leu Phe
            20

<210> SEQ ID NO 178
<211> LENGTH: 17
<212> TYPE: PRT
<213> ORGANISM: Artificial
<220> FEATURE:

<223> OTHER INFORMATION: rKKRrQRRrRPTTLrLw JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (15)..(15)
<223> OTHER INFORMATION: Arg is D-enantiomeric Arg
<220> FEATURE:
<221> NAME/KEY: Variant
<222> LOCATION: (17)..(17)
<223> OTHER INFORMATION: Trp is D-enantiomeric Trp

<400> SEQUENCE: 178

Arg Lys Lys Arg Arg Gln Arg Arg Arg Pro Thr Thr Leu Arg Leu
1               5                   10                  15
Trp

<210> SEQ ID NO 179
<211> LENGTH: 16
<212> TYPE: PRT
<213> ORGANISM: Artificial
<220> FEATURE:
<223> OTHER INFORMATION: rKKRrQRrRPTTLrLw JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (8)..(8)
<223> OTHER INFORMATION: Arg is D-enantiomeric Arg
<220> FEATURE:
<221> NAME/KEY: Variant
<222> LOCATION: (14)..(14)
<223> OTHER INFORMATION: Arg is D-enantiomeric Arg
<220> FEATURE:
<221> NAME/KEY: Variant
<222> LOCATION: (16)..(16)
<223> OTHER INFORMATION: Trp is D-enantiomeric Trp

<400> SEQUENCE: 179

Arg Lys Lys Arg Arg Gln Arg Arg Pro Thr Thr Leu Arg Leu Trp
1               5                   10                  15

<210> SEQ ID NO 180
<211> LENGTH: 17
<212> TYPE: PRT
<213> ORGANISM: Artificial
<220> FEATURE:
<223> OTHER INFORMATION: rKKRrQRRrRPTDLrLw JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant

```
<222> LOCATION: (9)..(9)
<223> OTHER INFORMATION: Arg is D-enantiomeric Arg
<220> FEATURE:
<221> NAME/KEY: Variant
<222> LOCATION: (15)..(15)
<223> OTHER INFORMATION: Arg is D-enantiomeric Arg
<220> FEATURE:
<221> NAME/KEY: Variant
<222> LOCATION: (17)..(17)
<223> OTHER INFORMATION: Trp is D-enantiomeric Trp

<400> SEQUENCE: 180

Arg Lys Lys Arg Arg Gln Arg Arg Arg Pro Thr Asp Leu Arg Leu
1               5                   10                  15

Trp

<210> SEQ ID NO 181
<211> LENGTH: 16
<212> TYPE: PRT
<213> ORGANISM: Artificial
<220> FEATURE:
<223> OTHER INFORMATION: rKKRrQRrRPTDLrLw JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (8)..(8)
<223> OTHER INFORMATION: Arg is D-enantiomeric Arg
<220> FEATURE:
<221> NAME/KEY: Variant
<222> LOCATION: (14)..(14)
<223> OTHER INFORMATION: Arg is D-enantiomeric Arg
<220> FEATURE:
<221> NAME/KEY: Variant
<222> LOCATION: (16)..(16)
<223> OTHER INFORMATION: Trp is D-enantiomeric Trp

<400> SEQUENCE: 181

Arg Lys Lys Arg Arg Gln Arg Arg Arg Pro Thr Asp Leu Arg Leu Trp
1               5                   10                  15

<210> SEQ ID NO 182
<211> LENGTH: 17
<212> TYPE: PRT
<213> ORGANISM: Artificial
<220> FEATURE:
<223> OTHER INFORMATION: rKKRrQRRrRPaTLNLf JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (12)..(12)
<223> OTHER INFORMATION: Ala is D-enantiomeric Ala
<220> FEATURE:
<221> NAME/KEY: Variant
<222> LOCATION: (17)..(17)
<223> OTHER INFORMATION: Phe is D-enantiomeric Phe
```

-continued

```
<400> SEQUENCE: 182

Arg Lys Lys Arg Arg Gln Arg Arg Arg Pro Ala Thr Leu Asn Leu
1               5                   10                  15

Phe

<210> SEQ ID NO 183
<211> LENGTH: 16
<212> TYPE: PRT
<213> ORGANISM: Artificial
<220> FEATURE:
<223> OTHER INFORMATION: rKKRrQRrRPaTLNLf JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (8)..(8)
<223> OTHER INFORMATION: Arg is D-enantiomeric Arg
<220> FEATURE:
<221> NAME/KEY: Variant
<222> LOCATION: (11)..(11)
<223> OTHER INFORMATION: Ala is D-enantiomeric Ala
<220> FEATURE:
<221> NAME/KEY: Variant
<222> LOCATION: (16)..(16)
<223> OTHER INFORMATION: Phe is D-enantiomeric Phe

<400> SEQUENCE: 183

Arg Lys Lys Arg Arg Gln Arg Arg Pro Ala Thr Leu Asn Leu Phe
1               5                   10                  15

<210> SEQ ID NO 184
<211> LENGTH: 17
<212> TYPE: PRT
<213> ORGANISM: Artificial
<220> FEATURE:
<223> OTHER INFORMATION: rKKRrQRrRPaTLNLf JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (8)..(8)
<223> OTHER INFORMATION: Arg is D-enantiomeric Arg
<220> FEATURE:
<221> NAME/KEY: Variant
<222> LOCATION: (12)..(12)
<223> OTHER INFORMATION: Ala is D-enantiomeric Ala
<220> FEATURE:
<221> NAME/KEY: Variant
<222> LOCATION: (17)..(17)
<223> OTHER INFORMATION: Phe is D-enantiomeric Phe

<400> SEQUENCE: 184

Arg Lys Lys Arg Arg Gln Arg Arg Lys Arg Pro Ala Thr Leu Asn Leu
1               5                   10                  15

Phe

<210> SEQ ID NO 185
<211> LENGTH: 20
<212> TYPE: PRT
```

-continued

```
<213> ORGANISM: Artificial
<220> FEATURE:
<223> OTHER INFORMATION: rKKRrQRRrRPkRPsTLNLf JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (12)..(12)
<223> OTHER INFORMATION: Lys is D-enantiomeric Lys
<220> FEATURE:
<221> NAME/KEY: Variant
<222> LOCATION: (15)..(15)
<223> OTHER INFORMATION: Ser is D-enantiomeric Ser
<220> FEATURE:
<221> NAME/KEY: Variant
<222> LOCATION: (20)..(20)
<223> OTHER INFORMATION: Phe is D-enantiomeric Phe

<400> SEQUENCE: 185

Arg Lys Lys Arg Arg Gln Arg Arg Arg Pro Lys Arg Pro Ser Thr
1               5                   10                  15

Leu Asn Leu Phe
            20

<210> SEQ ID NO 186
<211> LENGTH: 20
<212> TYPE: PRT
<213> ORGANISM: Artificial
<220> FEATURE:
<223> OTHER INFORMATION: rKKRrQRRrRPkRPqTLNLf JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (12)..(12)
<223> OTHER INFORMATION: Lys is D-enantiomeric Lys
<220> FEATURE:
<221> NAME/KEY: Variant
<222> LOCATION: (15)..(15)
<223> OTHER INFORMATION: Gln is D-enantiomeric Gln
<220> FEATURE:
<221> NAME/KEY: Variant
<222> LOCATION: (20)..(20)
<223> OTHER INFORMATION: Phe is D-enantiomeric Phe

<400> SEQUENCE: 186

Arg Lys Lys Arg Arg Gln Arg Arg Arg Pro Lys Arg Pro Gln Thr
1               5                   10                  15

Leu Asn Leu Phe
            20

<210> SEQ ID NO 187
<211> LENGTH: 20
```

```
<212> TYPE: PRT
<213> ORGANISM: Artificial
<220> FEATURE:
<223> OTHER INFORMATION: rKKRrQRRrRPkRPkTLNLf JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (12)..(12)
<223> OTHER INFORMATION: Lys is D-enantiomeric Lys
<220> FEATURE:
<221> NAME/KEY: Variant
<222> LOCATION: (15)..(15)
<223> OTHER INFORMATION: Lys is D-enantiomeric Lys
<220> FEATURE:
<221> NAME/KEY: Variant
<222> LOCATION: (20)..(20)
<223> OTHER INFORMATION: Phe is D-enantiomeric Phe

<400> SEQUENCE: 187

Arg Lys Lys Arg Arg Gln Arg Arg Arg Pro Lys Arg Pro Lys Thr
1               5                   10                  15

Leu Asn Leu Phe
            20

<210> SEQ ID NO 188
<211> LENGTH: 18
<212> TYPE: PRT
<213> ORGANISM: Artificial
<220> FEATURE:
<223> OTHER INFORMATION: rKKRrQRRrGKRKALKLf JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (18)..(18)
<223> OTHER INFORMATION: Phe is D-enantiomeric Phe

<400> SEQUENCE: 188

Arg Lys Lys Arg Arg Gln Arg Arg Arg Gly Lys Arg Lys Ala Leu Lys
1               5                   10                  15

Leu Phe

<210> SEQ ID NO 189
<211> LENGTH: 18
<212> TYPE: PRT
<213> ORGANISM: Artificial
<220> FEATURE:
<223> OTHER INFORMATION: rKKRrQRRrGKRKALrLf JNK inhibitor
<220> FEATURE:
<221> NAME/KEY: Variant
<222> LOCATION: (1)..(1)
<223> OTHER INFORMATION: Arg is D-enantiomeric Arg
```

```
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (16)..(16)
<223> OTHER INFORMATION: Arg is D-enantiomeric Arg
<220> FEATURE:
<221> NAME/KEY: Variant
<222> LOCATION: (18)..(18)
<223> OTHER INFORMATION: Phe is D-enantiomeric Phe

<400> SEQUENCE: 189

Arg Lys Lys Arg Arg Gln Arg Arg Gly Lys Arg Lys Ala Leu Arg
1               5                   10                  15

Leu Phe

<210> SEQ ID NO 190
<211> LENGTH: 16
<212> TYPE: PRT
<213> ORGANISM: Artificial
<220> FEATURE:
<223> OTHER INFORMATION: rKKRrQRRrRKALrLf  JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (14)..(14)
<223> OTHER INFORMATION: Arg is D-enantiomeric Arg
<220> FEATURE:
<221> NAME/KEY: Variant
<222> LOCATION: (16)..(16)
<223> OTHER INFORMATION: Phe is D-enantiomeric Phe

<400> SEQUENCE: 190

Arg Lys Lys Arg Arg Gln Arg Arg Arg Lys Ala Leu Arg Leu Phe
1               5                   10                  15

<210> SEQ ID NO 191
<211> LENGTH: 8
<212> TYPE: PRT
<213> ORGANISM: Artificial
<220> FEATURE:
<223> OTHER INFORMATION: RPTTLNLF JNK inhibitor

<400> SEQUENCE: 191

Arg Pro Thr Thr Leu Asn Leu Phe
1               5

<210> SEQ ID NO 192
<211> LENGTH: 9
<212> TYPE: PRT
<213> ORGANISM: Artificial
<220> FEATURE:
<223> OTHER INFORMATION: KRPTTLNLF JNK inhibitor

<400> SEQUENCE: 192
```

```
Lys Arg Pro Thr Thr Leu Asn Leu Phe
1               5
```

<210> SEQ ID NO 193
<211> LENGTH: 11
<212> TYPE: PRT
<213> ORGANISM: Artificial
<220> FEATURE:
<223> OTHER INFORMATION: L-IB1(s24)

<400> SEQUENCE: 193

```
Arg Pro Lys Arg Pro Thr Thr Leu Asn Leu Phe
1               5                   10
```

<210> SEQ ID NO 194
<211> LENGTH: 29
<212> TYPE: PRT
<213> ORGANISM: Artificial
<220> FEATURE:
<223> OTHER INFORMATION: GRKKRRQRRRPPKRPTTLNLFPQVPRSQD JNK inhibitor

<400> SEQUENCE: 194

```
Gly Arg Lys Lys Arg Arg Gln Arg Arg Arg Pro Pro Lys Arg Pro Thr
1               5                   10                  15

Thr Leu Asn Leu Phe Pro Gln Val Pro Arg Ser Gln Asp
            20                  25
```

<210> SEQ ID NO 195
<211> LENGTH: 25
<212> TYPE: PRT
<213> ORGANISM: Artificial
<220> FEATURE:
<223> OTHER INFORMATION: GRKKRRQRRRPTTLNLFPQVPRSQD JNK inhibitor

<400> SEQUENCE: 195

```
Gly Arg Lys Lys Arg Arg Gln Arg Arg Arg Pro Thr Thr Leu Asn Leu
1               5                   10                  15

Phe Pro Gln Val Pro Arg Ser Gln Asp
            20                  25
```

<210> SEQ ID NO 196
<211> LENGTH: 31
<212> TYPE: PRT
<213> ORGANISM: Artificial
<220> FEATURE:
<223> OTHER INFORMATION: L-TAT-IB1

<400> SEQUENCE: 196

```
Gly Arg Lys Lys Arg Arg Gln Arg Arg Arg Pro Pro Arg Pro Lys Arg
1               5                   10                  15

Pro Thr Thr Leu Asn Leu Phe Pro Gln Val Pro Arg Ser Gln Asp
            20                  25                  30
```

<210> SEQ ID NO 197
<211> LENGTH: 31
<212> TYPE: PRT
<213> ORGANISM: Artificial
<220> FEATURE:
<223> OTHER INFORMATION: D-TAT-IB1
<220> FEATURE:
<221> NAME/KEY: Variant
<222> LOCATION: (1)..(31)
<223> OTHER INFORMATION: All amino acids are D-enantiomeric amino acids

<400> SEQUENCE: 197

-continued

```
Asp Gln Ser Arg Pro Val Gln Pro Phe Leu Asn Leu Thr Thr Pro Arg
1               5                   10                  15

Lys Pro Arg Pro Pro Arg Arg Gln Arg Arg Lys Lys Arg Gly
            20                  25              30

<210> SEQ ID NO 198
<211> LENGTH: 39
<212> TYPE: PRT
<213> ORGANISM: Artificial
<220> FEATURE:
<223> OTHER INFORMATION: cJun (29-67)

<400> SEQUENCE: 198

Ser Asn Pro Lys Ile Leu Lys Gln Ser Met Thr Leu Asn Leu Ala Asp
1               5                   10                  15

Pro Val Gly Ser Leu Lys Pro His Leu Arg Ala Lys Asn Ser Asp Leu
            20                  25                  30

Leu Thr Ser Pro Asp Val Gly
        35

<210> SEQ ID NO 199
<211> LENGTH: 20
<212> TYPE: PRT
<213> ORGANISM: Artificial
<220> FEATURE:
<223> OTHER INFORMATION: RKKRRQRRRRPKRPATLNLF antibody negative control

<400> SEQUENCE: 199

Arg Lys Lys Arg Arg Gln Arg Arg Arg Pro Lys Arg Pro Ala Thr
1               5                   10                  15

Leu Asn Leu Phe
            20
```

JNK INHIBITOR MOLECULES

SEQUENCE LISTING SUBMISSION VIA EFS-WEB

A computer readable text file, entitled "067802-5029_SequenceListing.txt," created on or about 19 Dec. 2012, with a file size of about 87 kb contains the sequence listing for this application and is hereby incorporated by reference in its entirety.

The present invention relates to the field of enzyme inhibition, in particular to (poly-)peptide inhibitors of c-Jun amino terminal kinase (JNK). The present invention furthermore relates to methods for raising antibodies against such (poly-)peptide inhibitors as well as to the respective antibodies and cells producing the same.

The c-Jun amino terminal kinase (JNK) is a member of the stress-activated group of mitogen-activated protein (MAP) kinases. These kinases have been implicated in the control of cell growth and differentiation, and, more generally, in the response of cells to environmental stimuli. The JNK signal transduction pathway is activated in response to environmental stress and by the engagement of several classes of cell surface receptors. These receptors can include cytokine receptors, serpentine receptors and receptor tyrosine kinases. In mammalian cells, JNK has been implicated in biological processes such as oncogenic transformation and mediating adaptive responses to environmental stress. JNK has also been associated with modulating immune responses, including maturation and differentiation of immune cells, as well as effecting programmed cell death in cells identified for destruction by the immune system. The mitogen-activated protein kinase (MAPK) p38alpha was shown to negatively regulate the cell proliferation by antagonizing the JNK-c-Jun-pathway. The mitogen-activated protein kinase (MAPK) p38alpha therefore appears to be active in suppression of normal and cancer cell proliferation (see e.g. Hui et al., Nature Genetics, Vol 39, No. 6, June 2007). It was also shown, that c-Jun N-terminal Kinase (JNK) is involved in neuropathic pain produced by spinal nerve ligation (SNL), wherein SNL induced a slow and persistent activation of JNK, in particular JNK1, whereas p38 mitogen-activated protein kinase activation was found in spinal microglia after SNL, which had fallen to near basal level by 21 days (Zhuang et al., The Journal of Neuroscience, Mar. 29, 2006, 26(13):3551-3560)).

Inhibitors of the JNK signaling pathway as already known in the prior art, particularly include e.g. upstream kinase inhibitors (for example, CEP-1347), small chemical inhibitors of JNK (SP600125 and AS601245), which directly affect kinase activity e.g. by competing with the ATP-binding site of the protein kinase, and peptide inhibitors of the interaction between JNK and its substrates (see e.g. Kuan et al., Current Drug Targets—CNS & Neurological Disorders, February 2005, vol. 4, no. 1, pp. 63-67; WO 2007/031280; all incorporated herewith by reference). WO 2007/031280 discloses small cell permeable fusion peptides, comprising a so-called TAT transporter sequence derived from the basic trafficking sequence of the HIV-TAT protein and an amino acid inhibitory sequence of IB1.

WO 2007/031280 discloses in particular two specific sequences, L-TAT-IB1 (GRKKRRQRRRPPRPKRPTTLN-LFPQVPRSQD, herein SEQ ID NO: 196) and D-TAT-IB1 (dqsrpvqpflnlttprkprpprrrqrrkkrg; herein SEQ ID NO: 197), the latter being the retro-inverso sequence of L-TAT-IB1. Due to the HIV TAT derived transporter sequence, these fusion peptides are more efficiently transported into the target cells, where they remain effective until proteolytic degradation.

Since ATP independent peptide inhibitors of JNK are usually more specific inhibitors, they are frequently the first choice if it comes to inhibiting JNK. However, even the peptide inhibitors disclosed in WO 2007/031280 are not optimal. For example, compound L-TAT-IB1 (herein SEQ ID NO: 196) which consists of L amino acids only, is quickly proteolytically degraded. In order to overcome this problem the inventors of WO 2007/031280 also suggested D-TAT-IB1 (herein SEQ ID NO: 197), which comprises D amino acids. To be more precise, D-TAT-IB1 exhibits the retro-inverso sequence of L-TAT-IB1. Incorporation of D-amino acids is made difficult by the fact that the change in stereochemistry may lead to a loss of function. The retro-inverso approach may be employed to reduce said risk because the use of i) only D-amino acids ii) but in the inverse peptide sequence may more likely yield an acceptable conformational analogue to the original peptide than incorporating one or more D-amino acids into the original sequence. In the case of WO 2007/031280 this approach resulted nevertheless in a significant decrease in inhibitory capacity in comparison to L-TAT-IB1 (see FIG. 4). Additionally, the retro-inverso peptide is extremely stable towards proteolytic digestion with the consequence that controlled digestions, for example in time sensitive experiments, are hardly possible.

Therefore, there is still a need in the art for peptide inhibitors of JNK which are more stable than for example L-TAT-IB1 (herein SEQ ID NO: 196). On the other hand there is a need for peptide inhibitors of JNK which are more active while less stable than for example D-TAT-IB1 (herein SEQ ID NO: 197).

Thus, the problem to be solved by the present invention was to provide further (peptide) inhibitors of JNK which are preferably less sensitive to proteolytic degradation than L-TAT-IB1 as disclosed in WO 2007/031280, but are preferably at the same time more sensitive to proteolytic degradation and/or more active than D-TAT-IB1 as disclosed in WO 2007/031280.

The object of the present invention is solved by the inventor by means of the subject-matter set out in the appended claims.

In the following a brief description of the appended figures will be given. The figures are intended to illustrate the present invention in more detail. However, they are not intended to limit the subject matter of the invention in any way.

FIG. 1: Illustration of the inhibitory efficacy of several JNK inhibitors according to the present invention, which was investigated by in vitro AlphaScreen assay (Amplified Luminescence Proximity Homogeneous-Screen Assay).

FIG. 1A: Inhibition of JNK1 by SEQ ID NOs: 193, 2, 3, 5, 6, and 7.

Figure 1B:
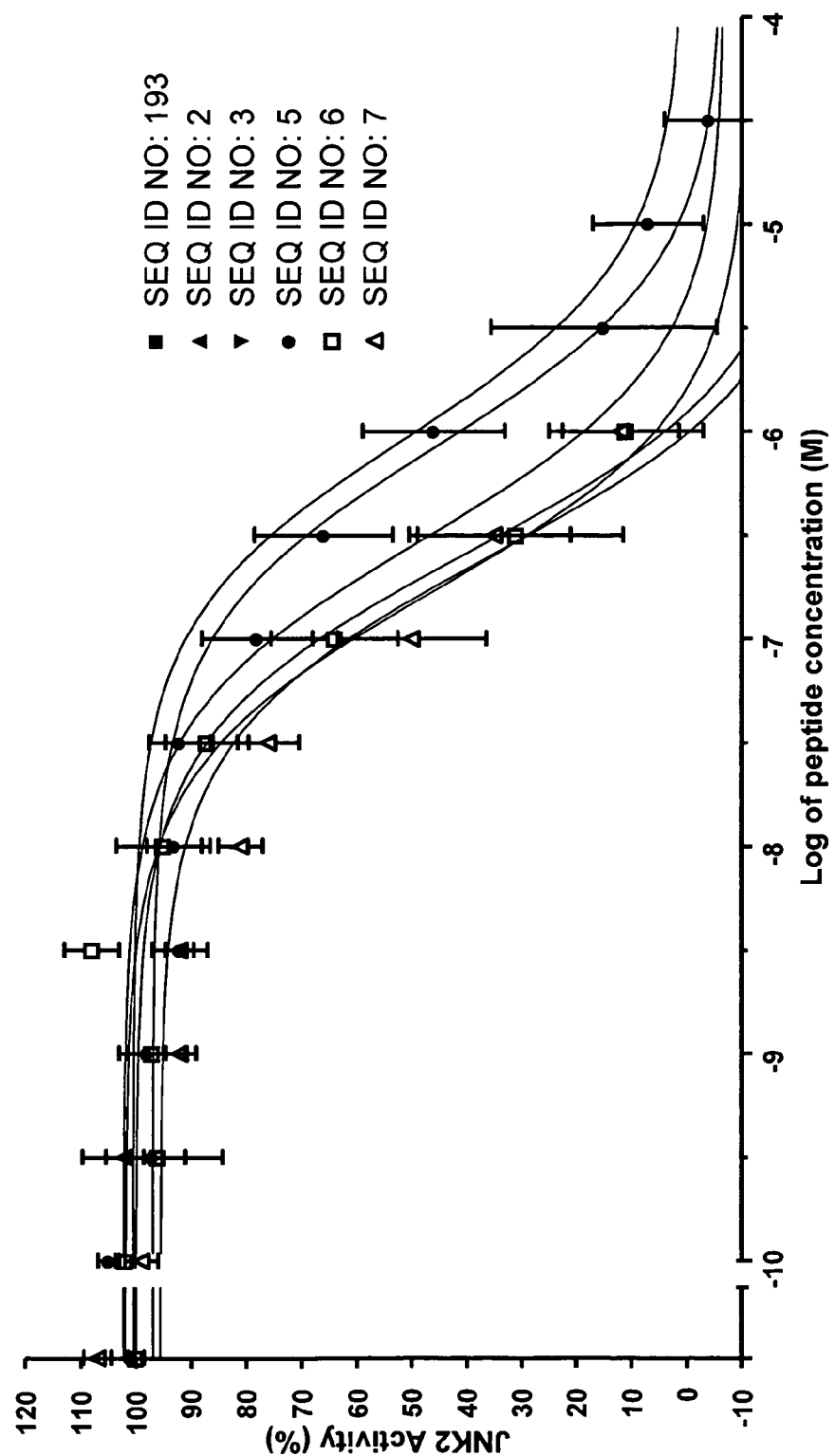

FIG. 1B: Inhibition of JNK2 by SEQ ID NOs: 193, 2, 3, 5, 6, and 7.

Figure 1C:
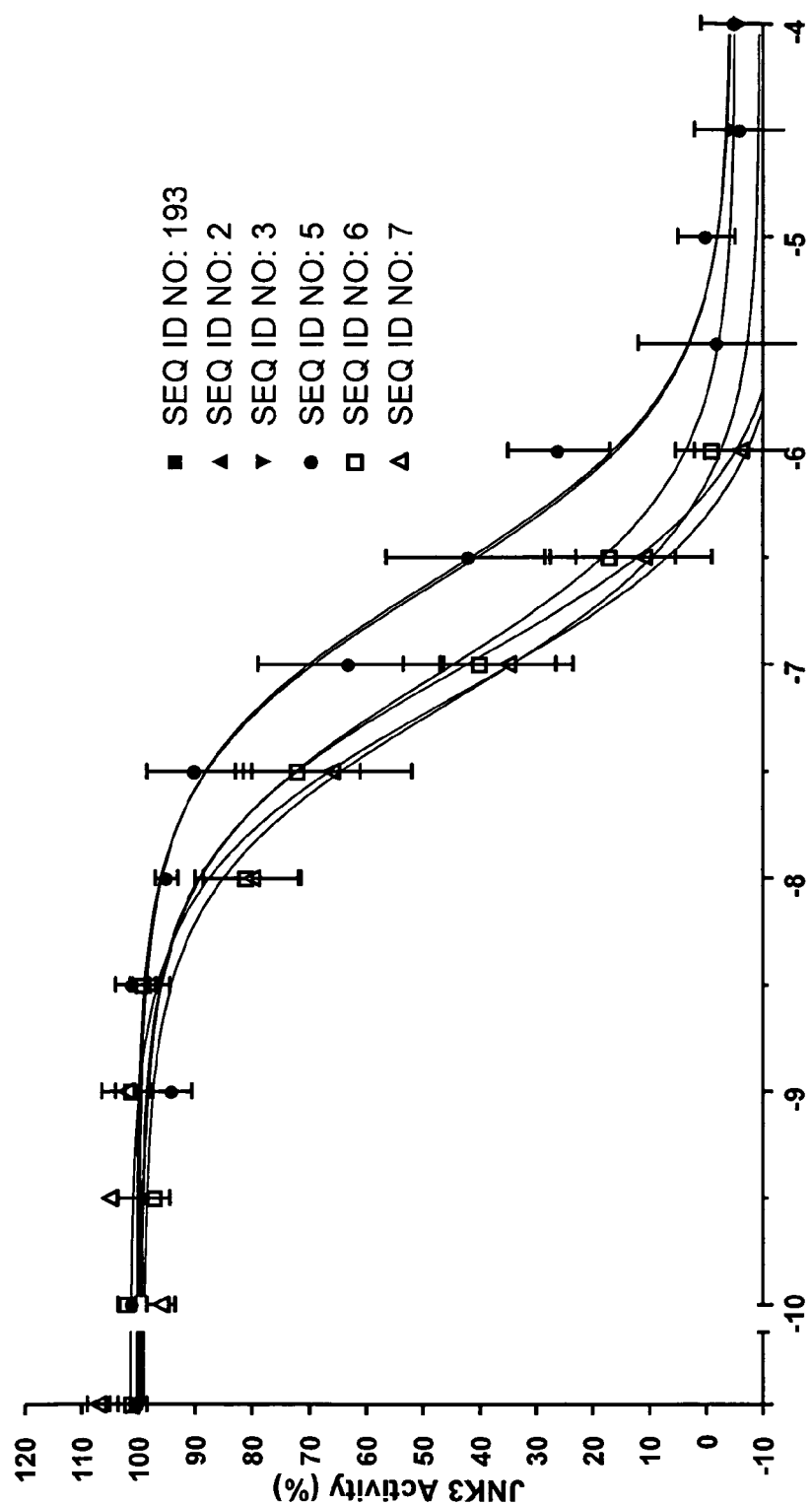

FIG. 1C: Inhibition of JNK3 by SEQ ID NOs: 193, 2, 3, 5, 6, and 7.

FIG. 2: Table illustrating the inhibitory efficacy of several JNK inhibitors (SEQ ID NOs: 193, 2, 3, 5, 6, and 7) according to the present invention. Given are the IC50 values in the nM range, the respective standard error of the mean and the number of experiments performed (n).

FIG. 3: Illustration of the inhibitory efficacy of several JNK inhibitors according to the present invention, which are fusion proteins of a JNK inhibitory (poly-)peptide sequence and a transporter sequence. The inhibitory efficacy was determined by means of in vitro AlphaScreen assay (Amplified Luminescence Proximity Homogeneous-Screen Assay).

Figure 3A:
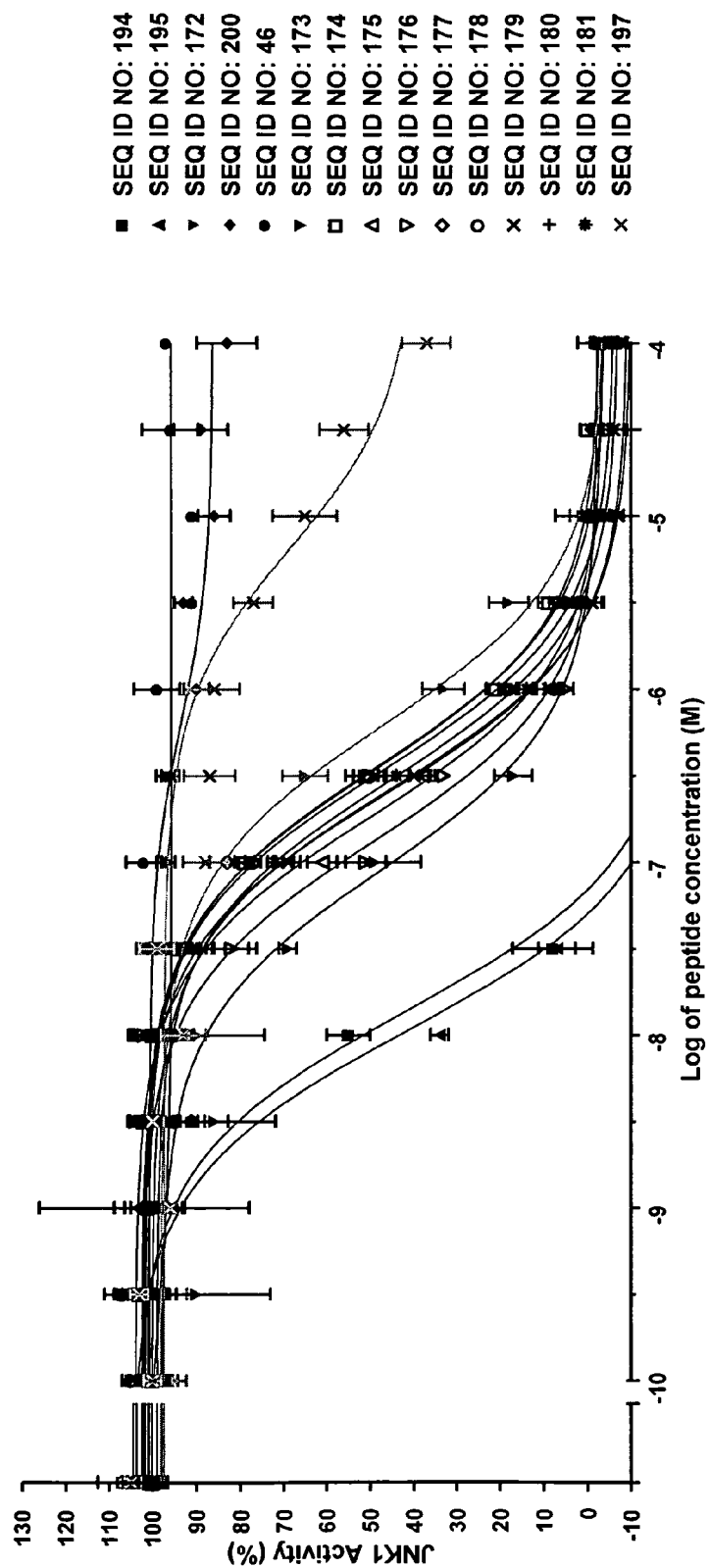

FIG. 3A: Inhibition of JNK1 by SEQ ID NOs: 194, 195, 172, 200, 46, 173, 174, 175, 176, 177, 178, 179, 180, 181 and 197.

Figure 3B:
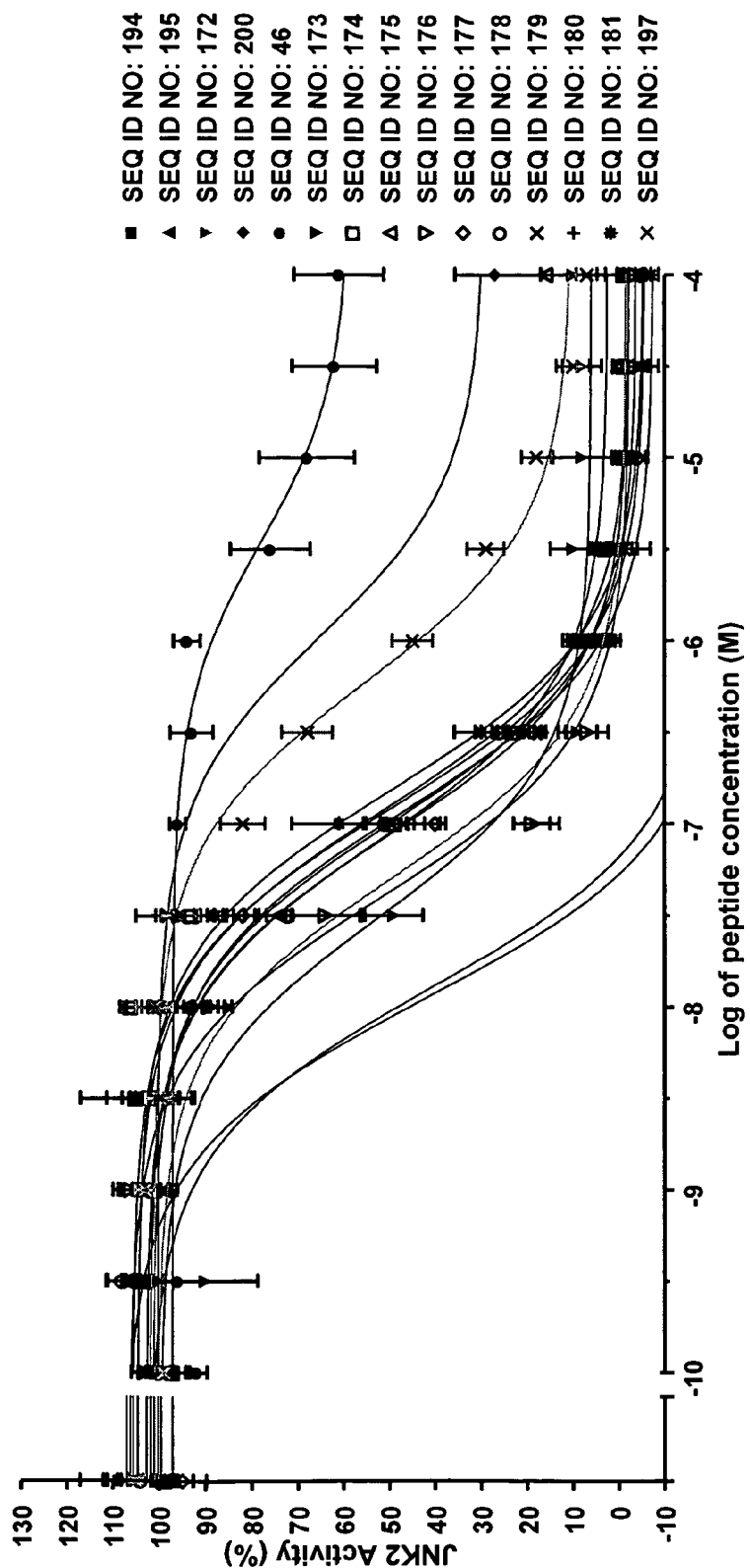

FIG. 3B: Inhibition of JNK2 by SEQ ID NOs: 194, 195, 172, 200, 46, 173, 174, 175, 176, 177, 178, 179, 180, 181 and 197.

Figure 3C:
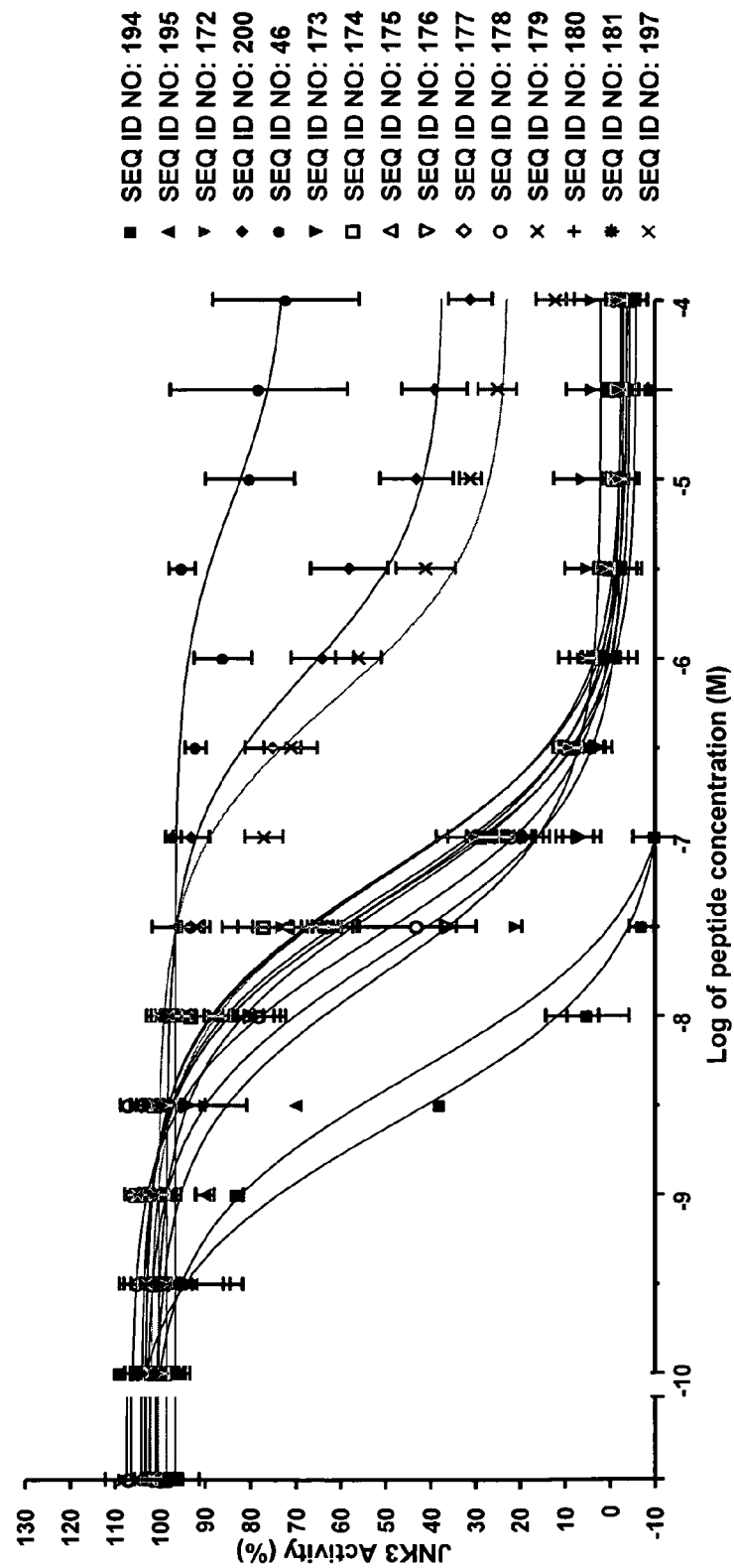

FIG. 3C: Inhibition of JNK3 by SEQ ID NOs: 194, 195, 172, 200, 46, 173, 174, 175, 176, 177, 178, 179, 180, 181 and 197.

Figure 3D:
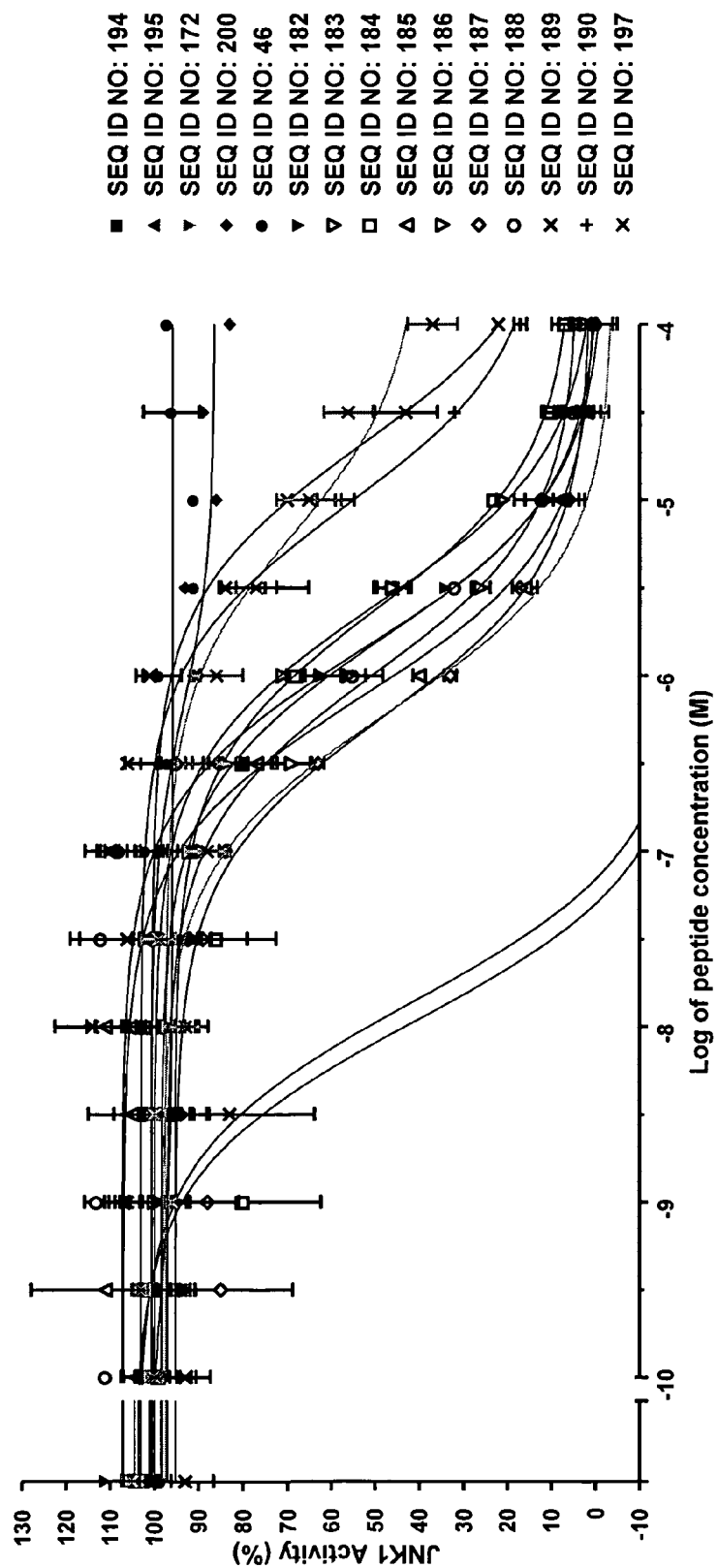

FIG. 3D: Inhibition of JNK1 by SEQ ID NOs: 194, 195, 172, 200, 46, 182, 183, 184, 185, 186, 187, 188, 189, 190 and 197.

Figure 3E:
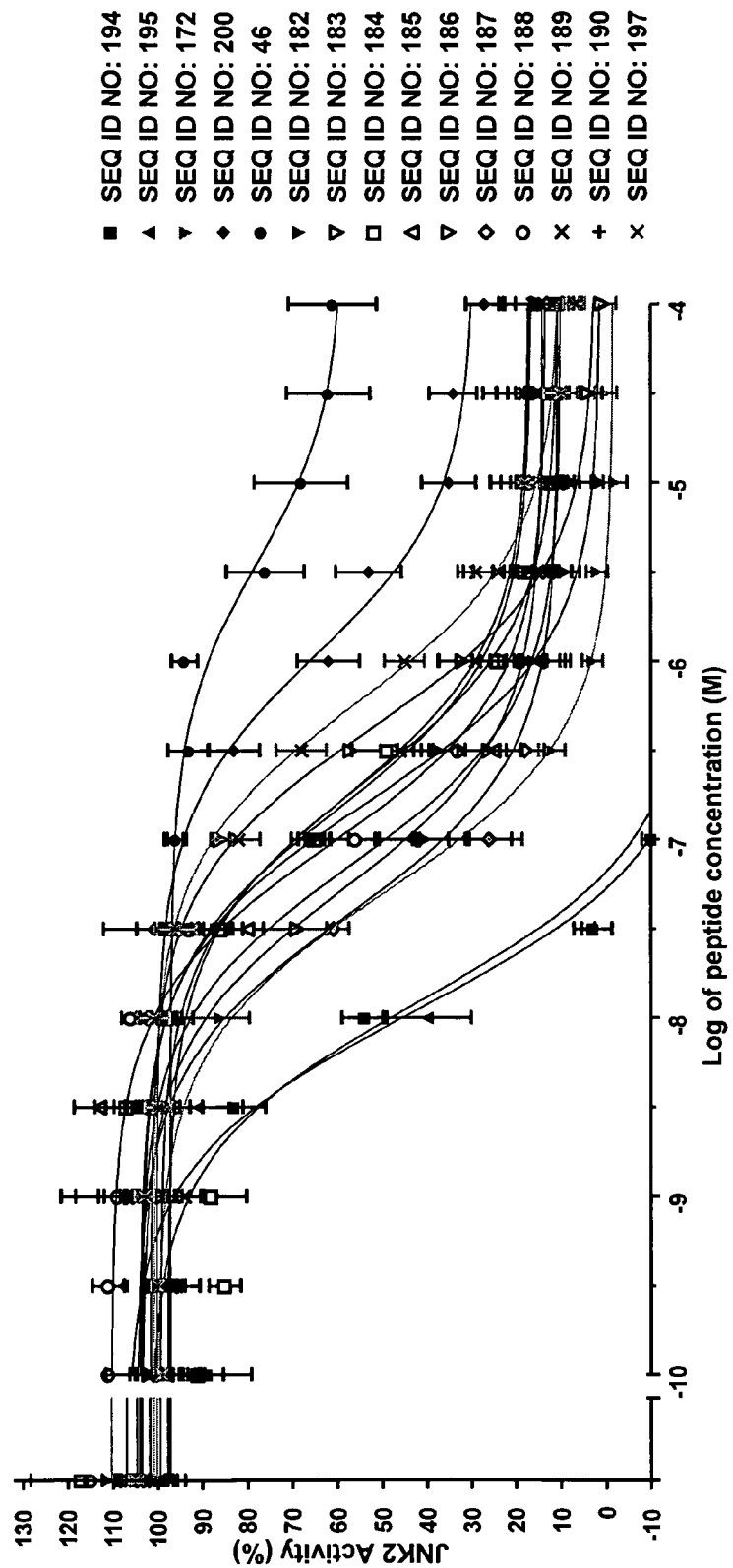

FIG. 3E: Inhibition of JNK2 by SEQ ID NOs: 194, 195, 172, 200, 46, 182, 183, 184, 185, 186, 187, 188, 189, 190 and 197.

Figure 3F:
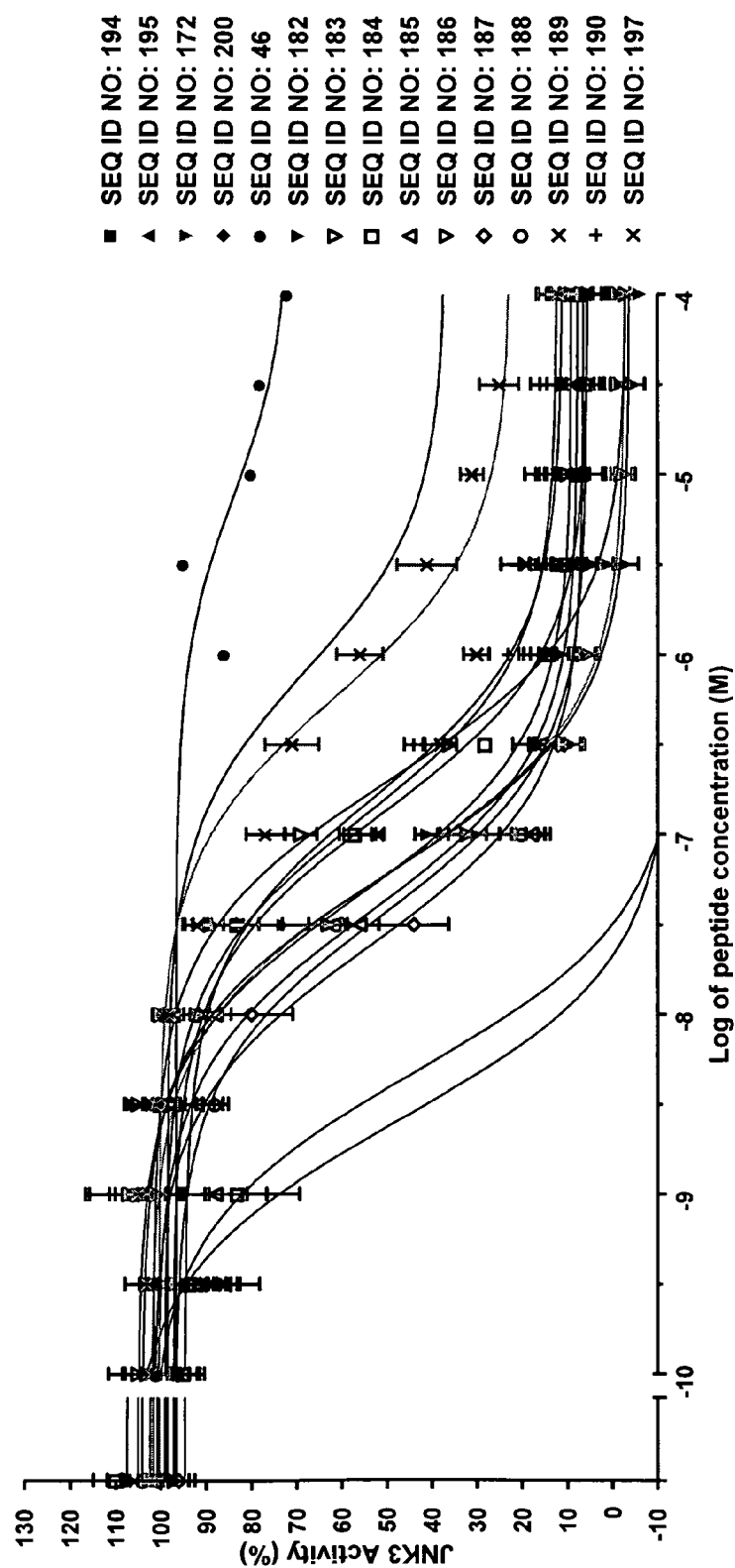

FIG. 3F: Inhibition of JNK3 by SEQ ID NOs: 194, 195, 172, 200, 46, 182, 183, 184, 185, 186, 187, 188, 189, 190 and 197.

FIG. 4: Table illustrating the inhibitory efficacy of several JNK inhibitors according to the present invention, which are fusion proteins of a JNK inhibitory (poly-)peptide sequence and a transporter sequence. Given are the IC50 values in the nM range, the respective standard error of the mean (SEM) and the number of experiments performed (n).

Figure 5:
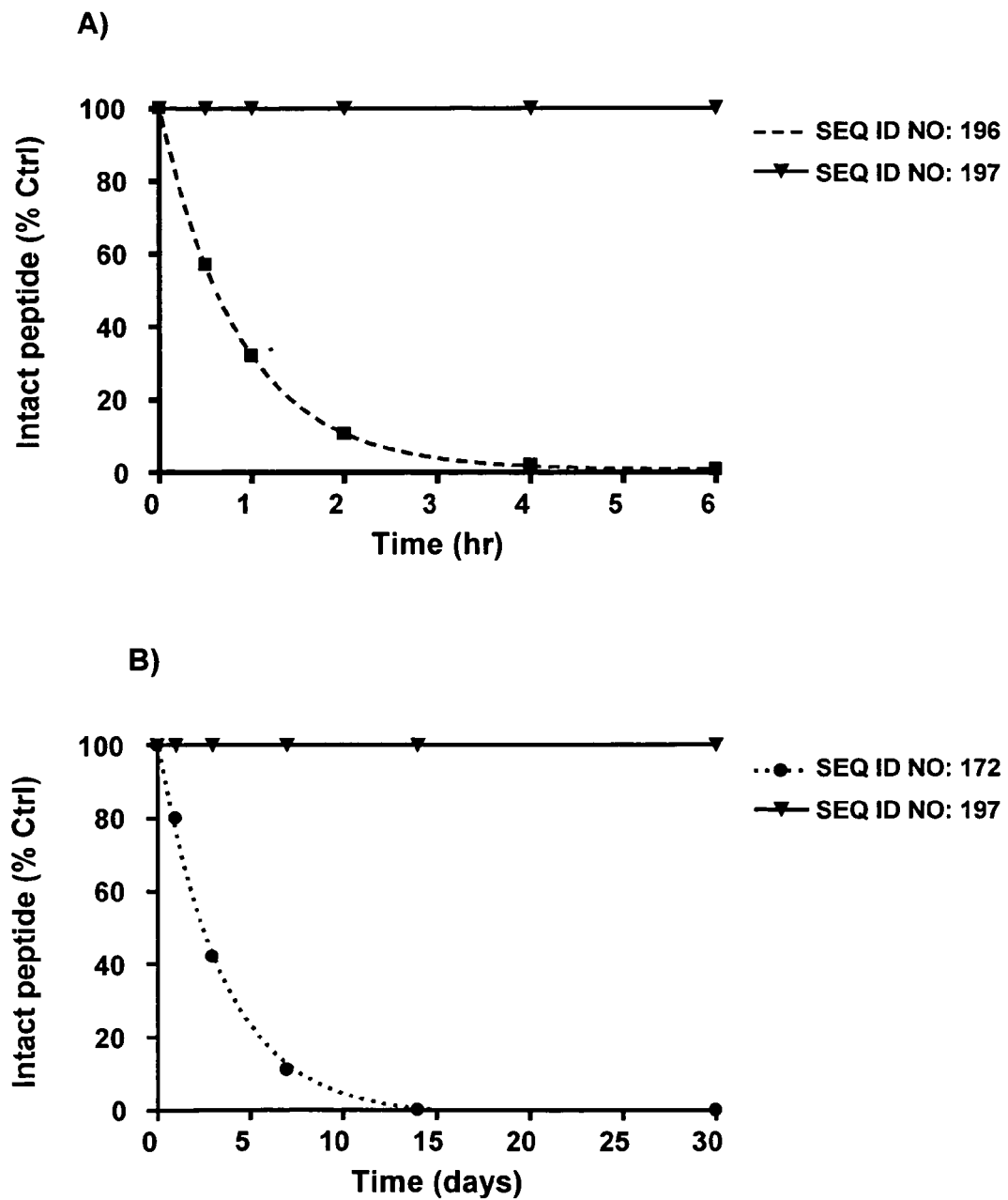

FIG. 5: Stability of JNK inhibitors with SEQ ID NOs: 172, 196 and 197 in 50% human serum. The JNK inhibitor with SEQ ID NO: 196 was totally degraded into amino acids residues within 6 hours (A). The JNK inhibitor with SEQ ID NO: 172 was completely degraded only after 14 days (B). The JNK inhibitor with SEQ ID NO: 197 was stable at least up to 30 days (B).

Figure 6A:
Figure 6B:
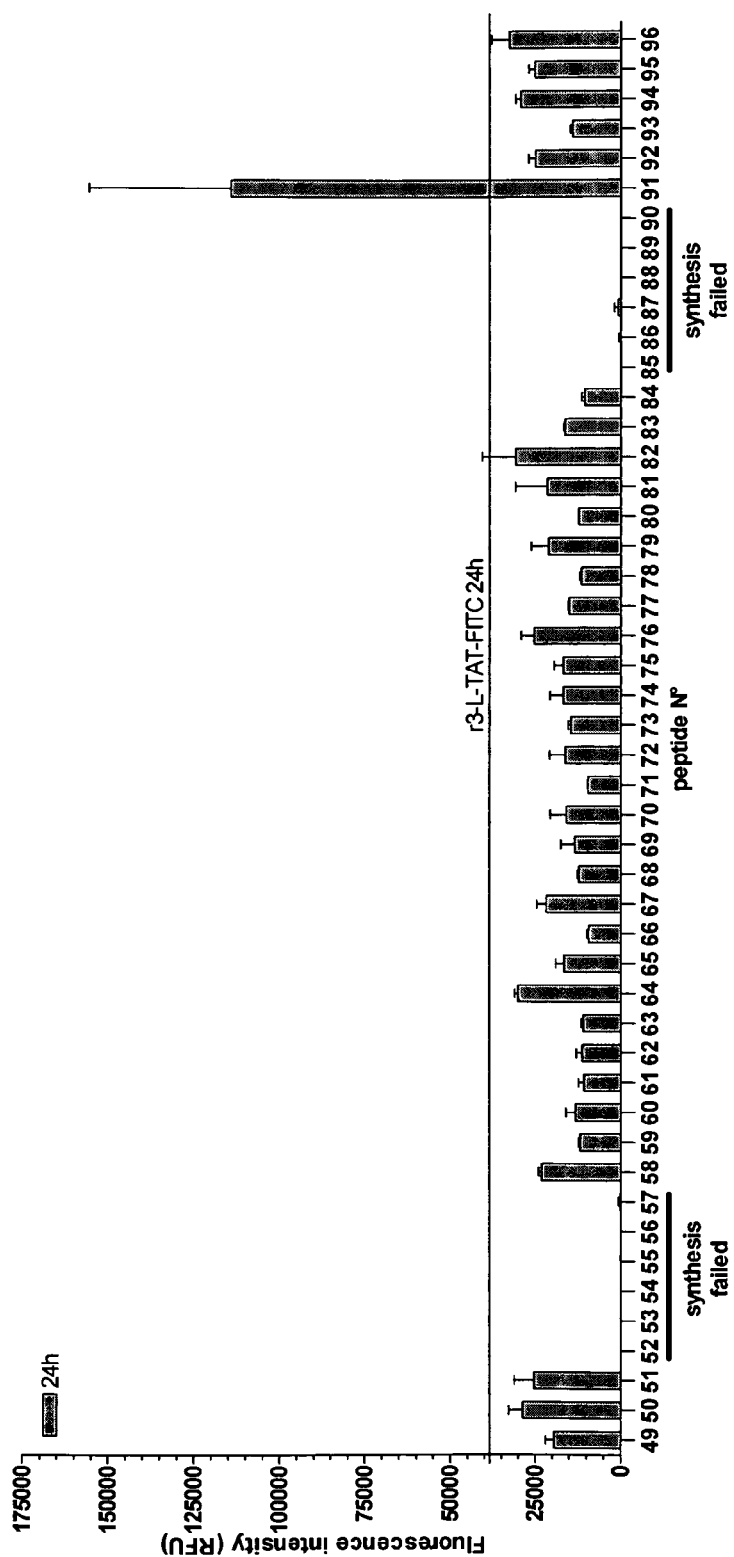

FIG. 6: shows internalizations experiments using TAT derived transporter constructs with D-amino acid/L-amino acid pattern as denoted in SEQ ID NO: 30. The transporter sequences analyzed correspond to SEQ ID NOs: 52-94 plus SEQ ID NOs: 45, 47, 46, 43 and 99 (FIG. 6a) and SEQ ID NOs: 100-147 (FIG. 6b). As can be seen, all transporters with the consensus sequence rXXXrXXXr (SEQ ID NO: 31) showed a higher internalization capability than the L-TAT transporter (SEQ ID NO: 43). Hela cells were incubated 24 hours in 96 well plate with 10 mM of the respective transporters. The cells were then washed twice with an acidic buffer (0.2M Glycin, 0.15M NaCl, pH 3.0) and twice with PBS. Cells were broken by the addition of RIPA lysis buffer. The relative amount of internalized peptide was then determined by reading the fluorescence intensity (Fusion Alpha plate reader; PerkinElmer) of each extract followed by background subtraction.

Figure 7:
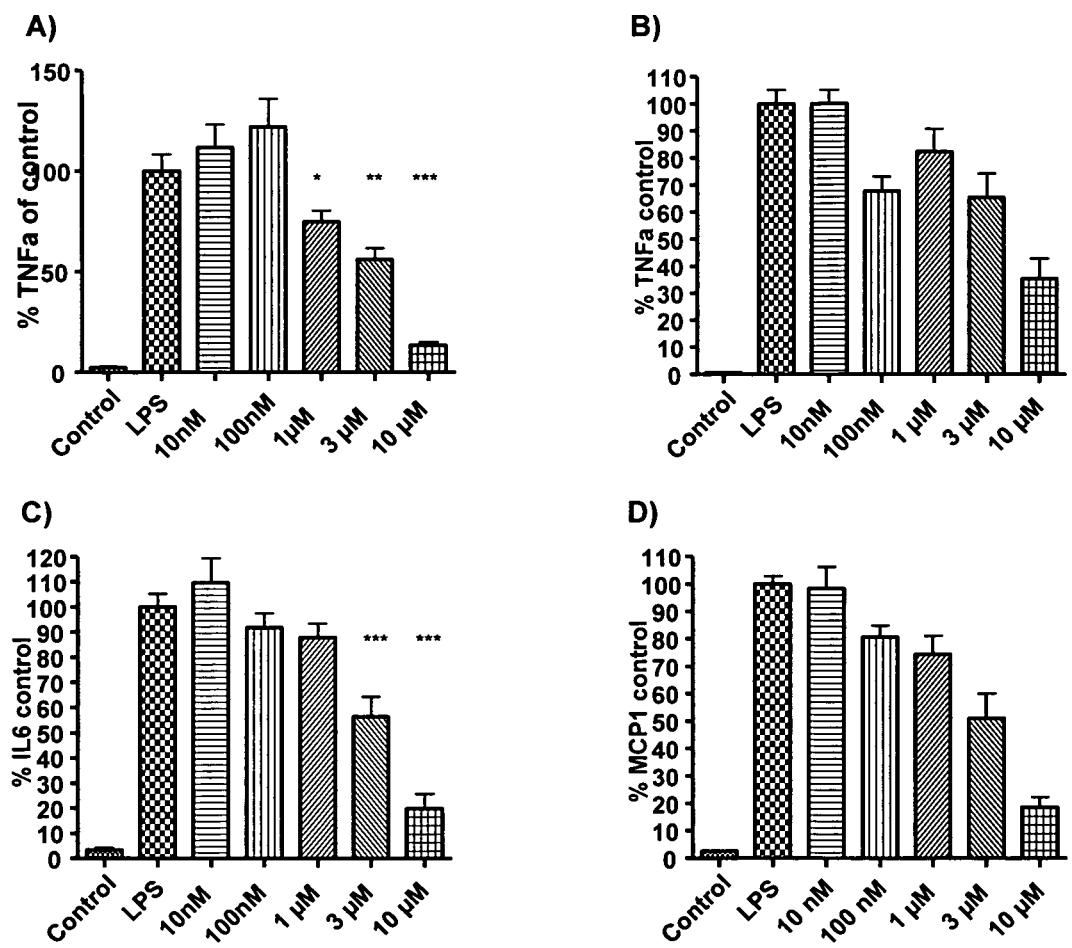

FIG. 7 The JNK inhibitor with the sequence of SEQ ID NO: 172 blocks LPS-induced cytokine and chemokine release in THP1-PMA-differentiated macrophages. FIG. 7A: TNF release (THP1pma 6 h 3 ng/ml LPS); FIG. 7B: TNFa release (THP1 pma 6 h 10 ng/ml LPS); FIG. 7C: IL 6 release (THP1pma 6 h 10 ng/ml LPS); FIG. 7D: MCP1 release (THP1 pma 6 h 3 ng/ml LPS).

Figure 8:
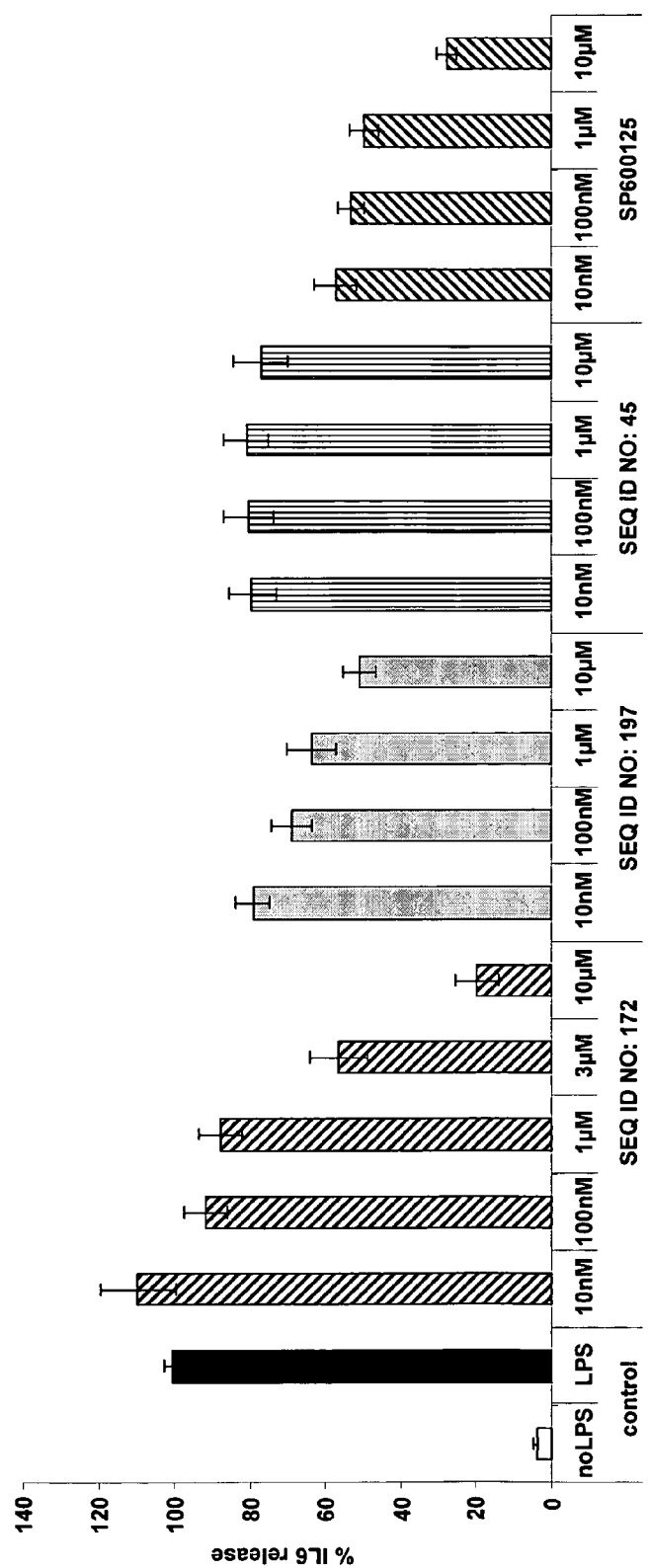

FIG. 8 The JNK inhibitor of SEQ ID NO: 172 blocks LPS-induced IL6 release in THP1 differentiated macrophages with higher potency than D-TAT-IB1 (SEQ ID NO: 197), dTAT (SEQ ID NO: 45) and SP 600125. LPS was added for 6 h (10 ng/ml).

Figure 9:
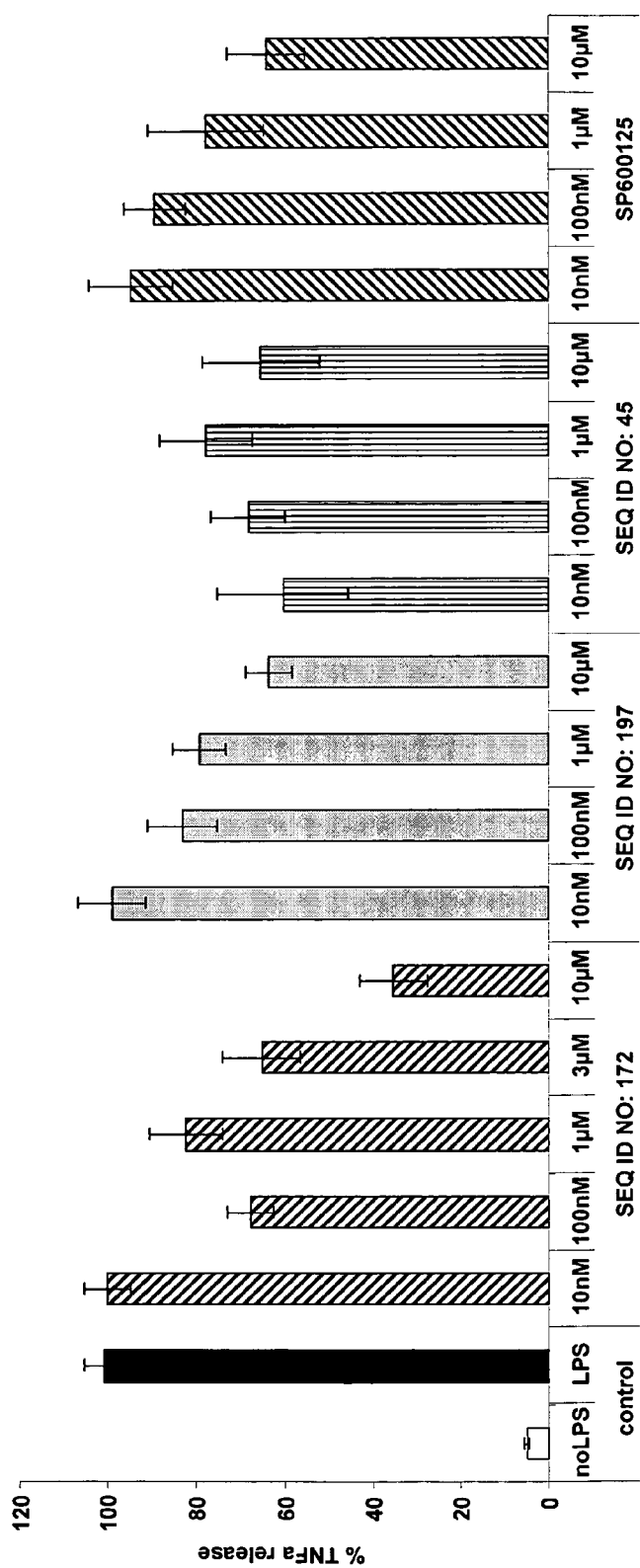

FIG. 9 The JNK inhibitor of SEQ ID NO: 172 blocks LPS-induced TNFα release in THP1 differentiated macrophages with higher potency than D-TAT-IB1 (SEQ ID NO: 197), dTAT (SEQ ID NO: 45) and SP 600125. LPS was added for 6 h (10 ng/ml).

Figure 10:
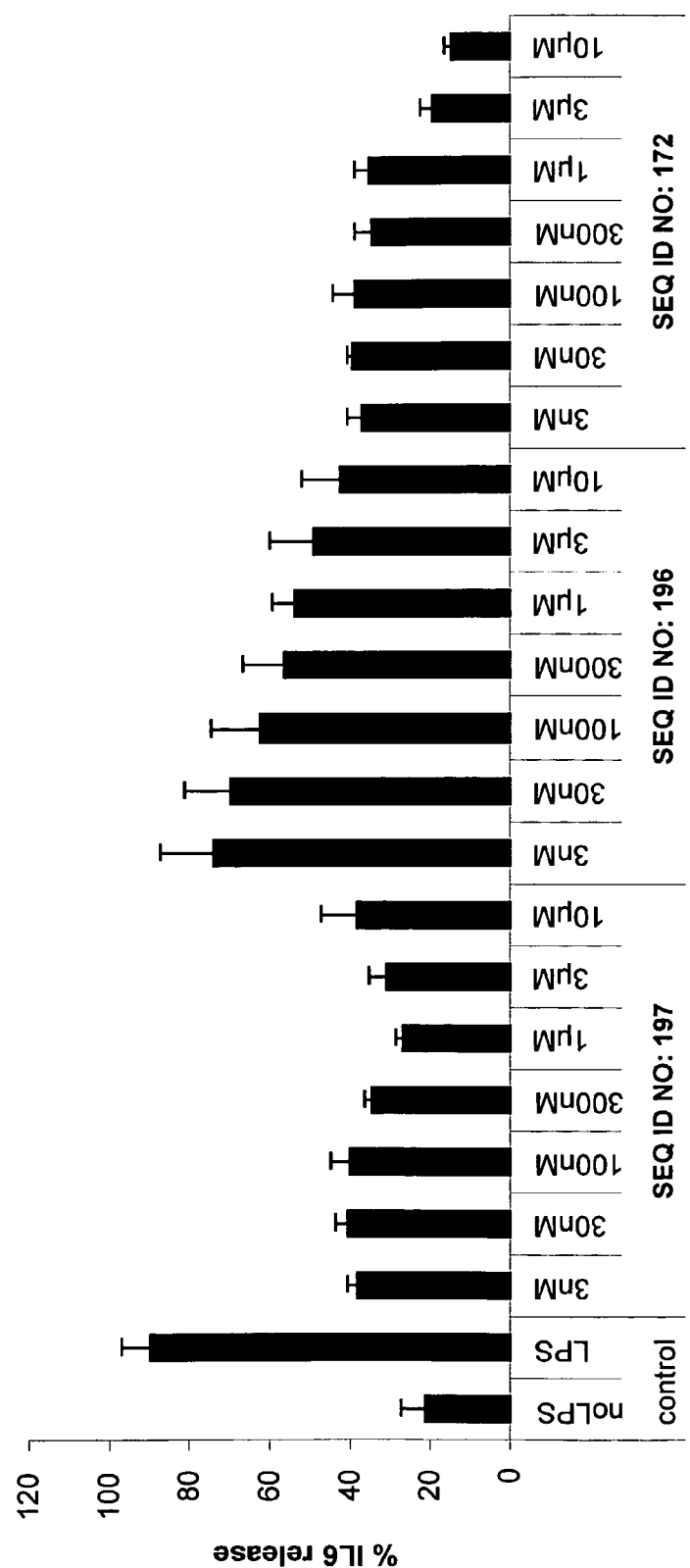

FIG. 10 The JNK inhibitor of SEQ ID NO: 172 blocks LPS-induced IL-6 release in PMA differentiated macrophages with higher potency than D-TAT-IB1 (SEQ ID NO: 197) and L-TAT-IB1 (SEQ ID NO: 196). LPS was added for 6 h.

Figure 11:
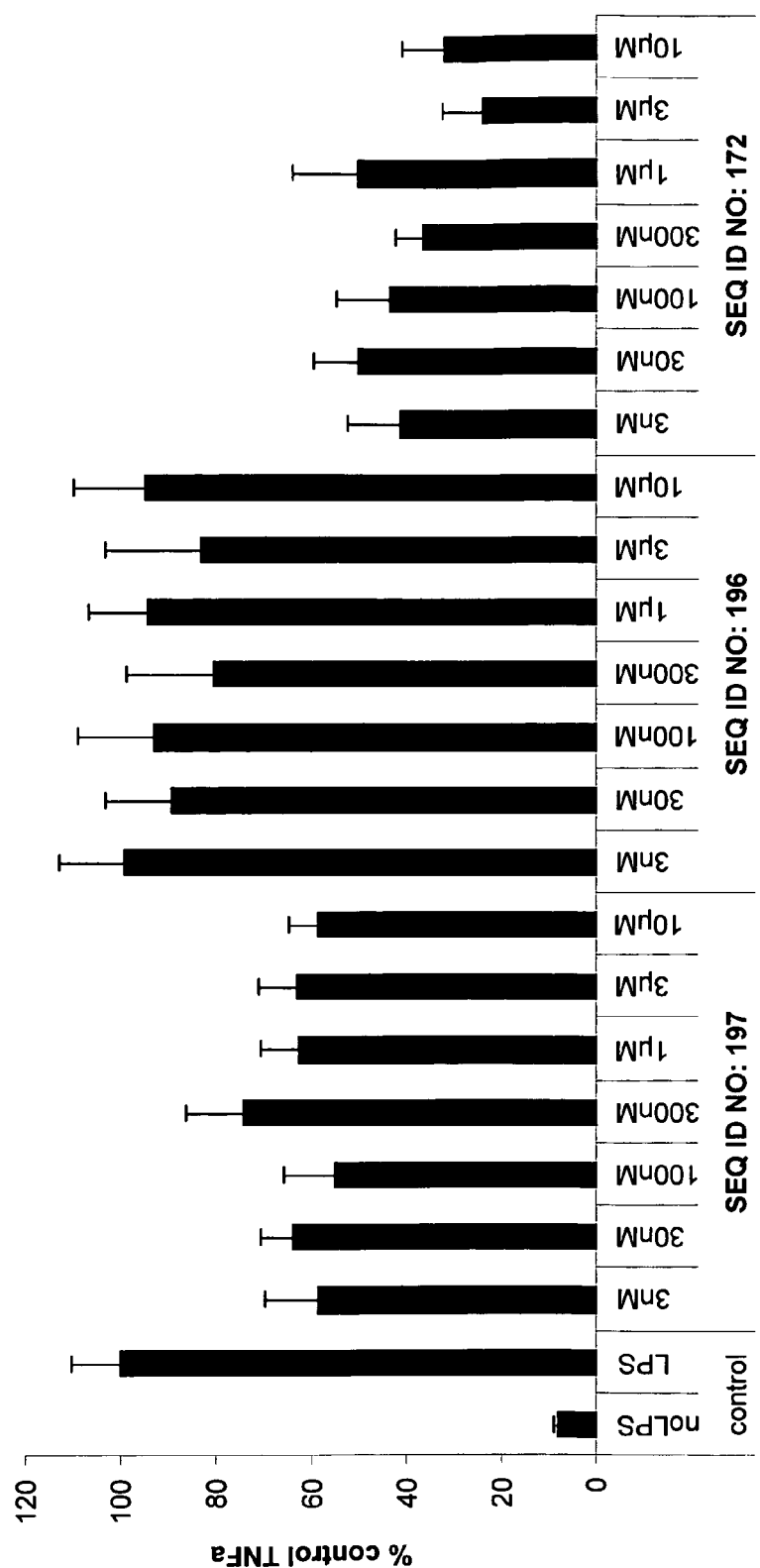

FIG. 11 The JNK inhibitor of SEQ ID NO: 172 blocks LPS-induced TNFα release in PMA differentiated macrophages with higher potency than D-TAT-IB1 (SEQ ID NO: 197) and L-TAT-IB1 (SEQ ID NO: 196).

Figure 12:
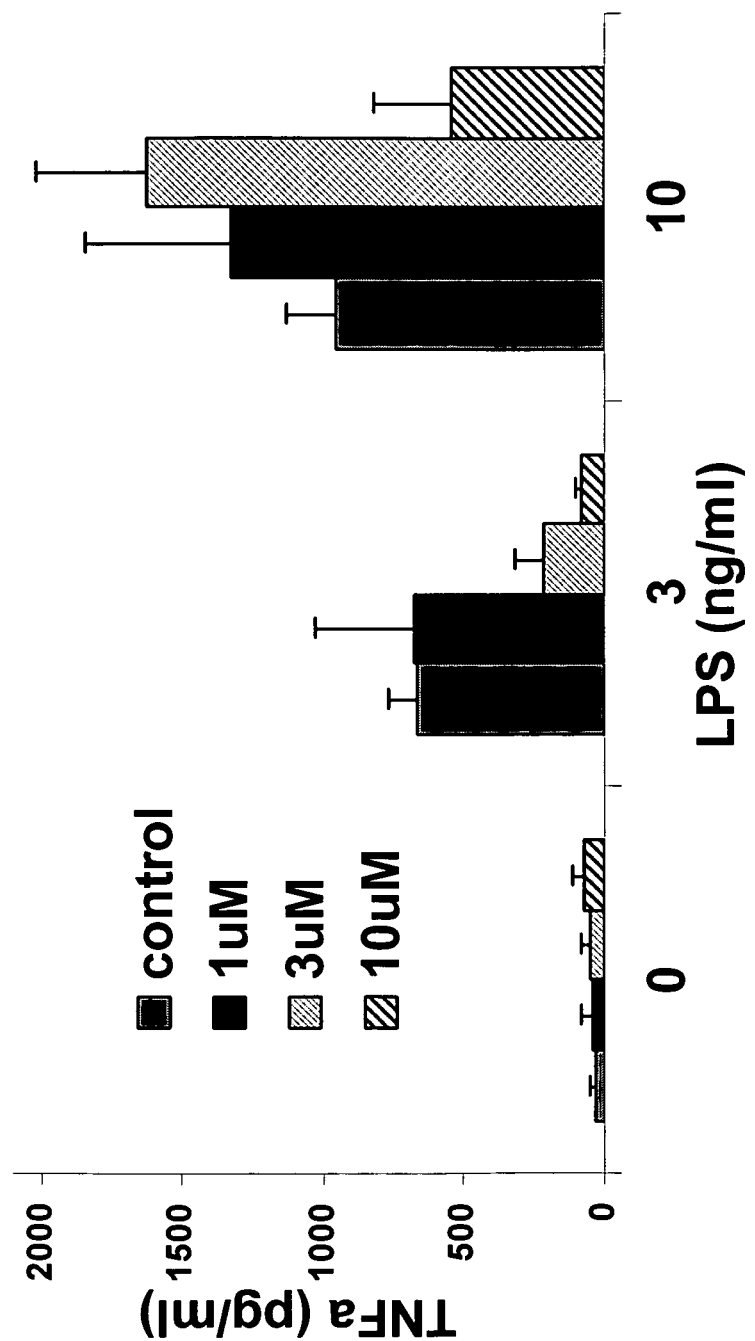

FIG. 12 The JNK inhibitor of SEQ ID NO: 172 blocks LPS-induced TNFα release in Primary Rat Whole Blood Cells at 3 ng/ml. Given are the results for the control, 1 µM of SEQ ID NO: 172, 3 µM of SEQ ID NO: 172, and 10 µM of SEQ ID NO: 172 at different levels of LPS (ng/ml).

Figure 13:
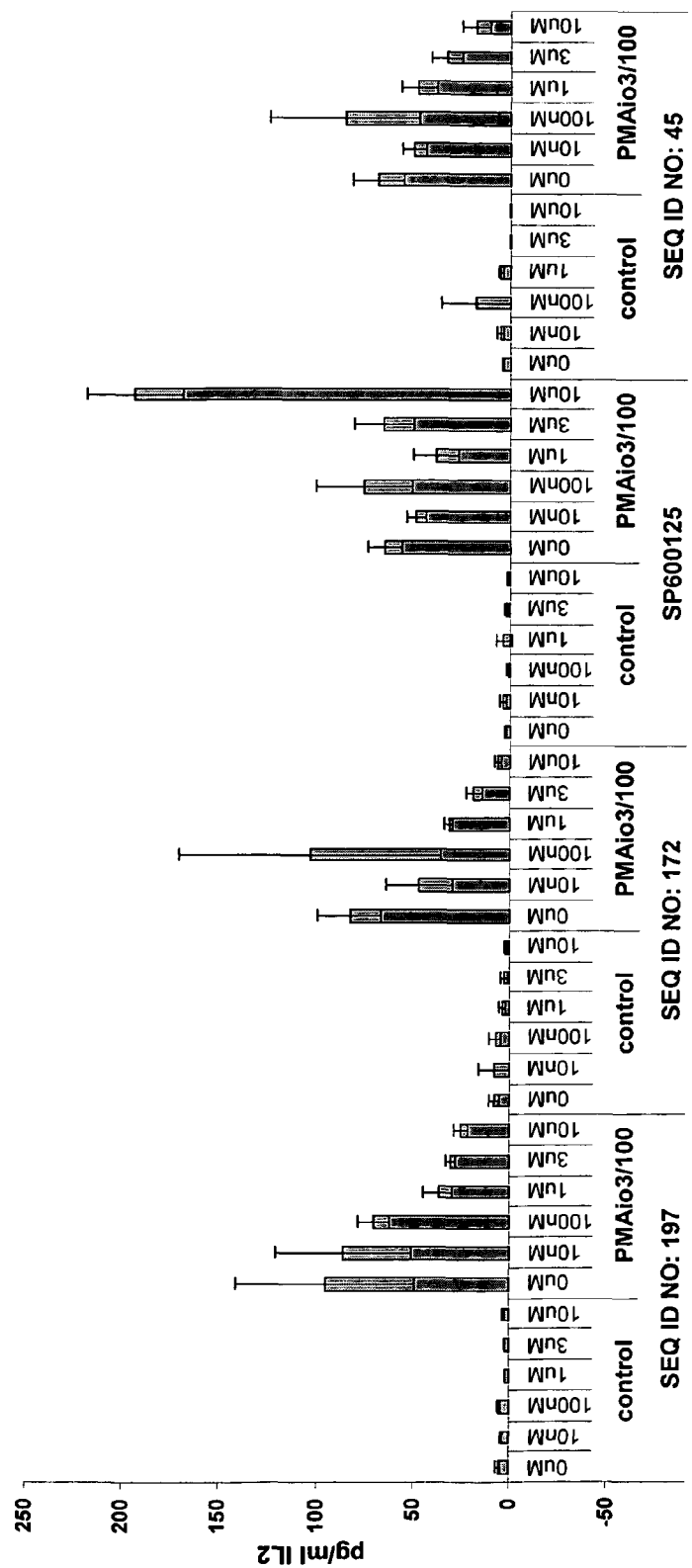

FIG. 13 The JNK inhibitor of SEQ ID NO: 172 blocks IL2 secretion by primary human T-cells in response to PMA/Ionomycin.

Figure 14:
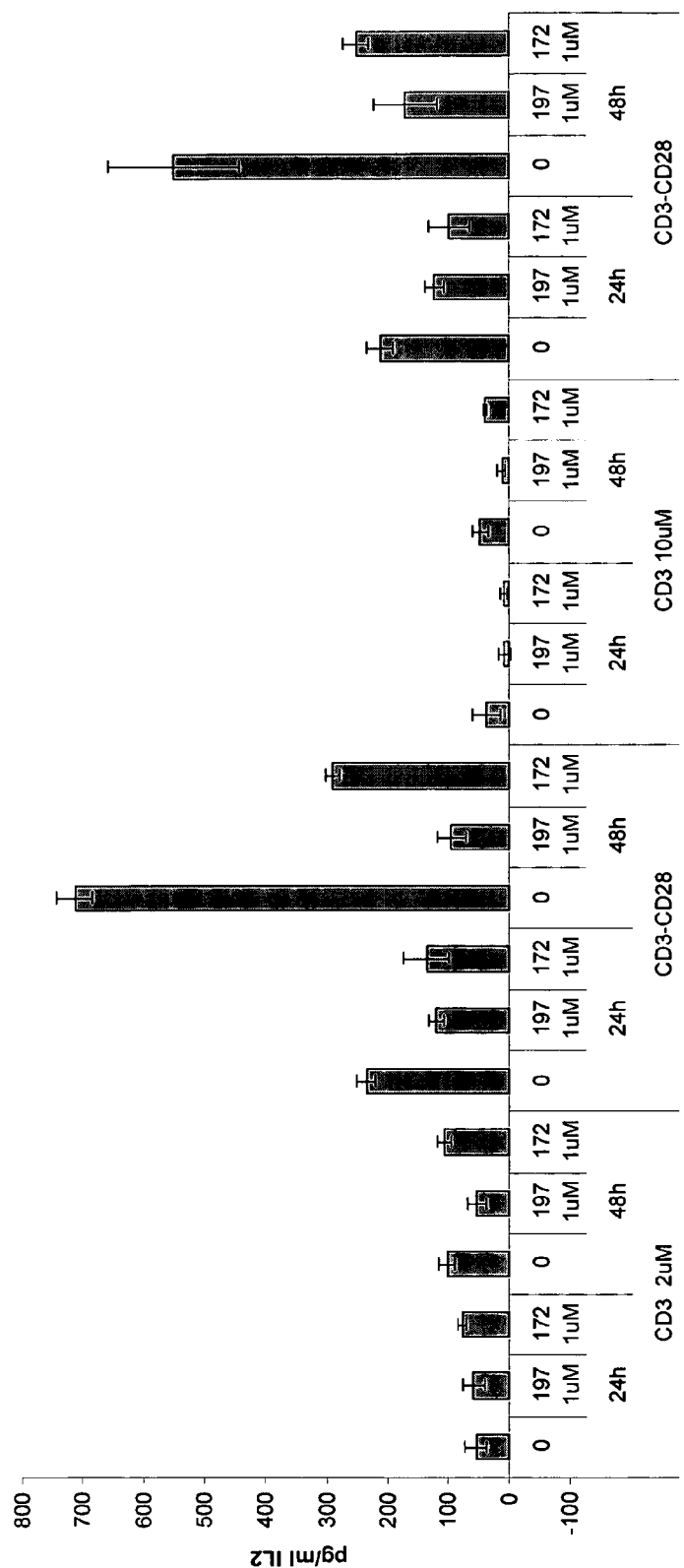

FIG. 14 The JNK inhibitor of SEQ ID NO: 172 blocks IL2 secretion by primary human T-cells in response to CD3/CD28 stimulation. The JNK inhibitors used are Indicated by their SEQ ID NO: 172 and 197.

Figure 15:
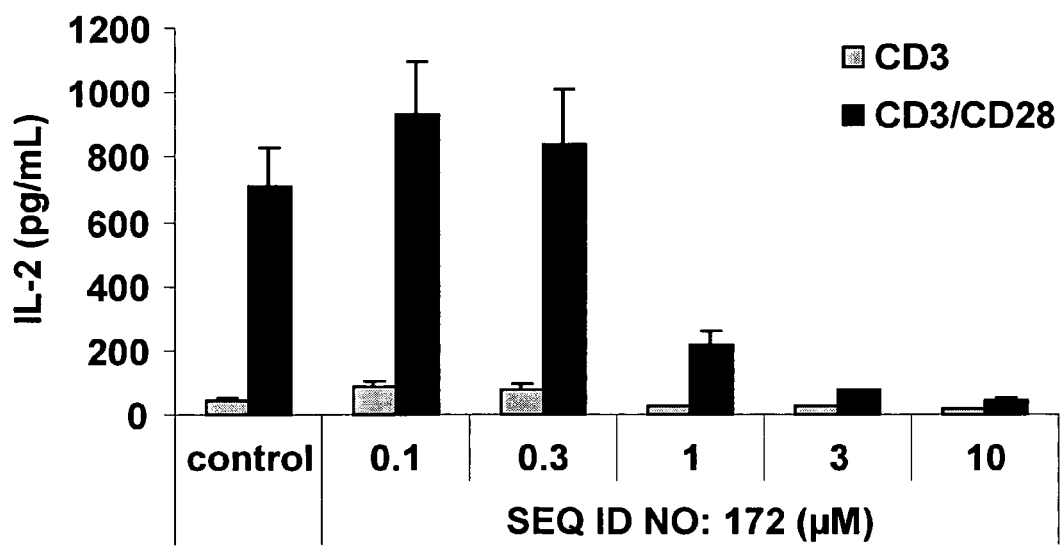

FIG. 15 Dose-dependent inhibition by JNK inhibitor with SEQ ID NO: 172 of CD3/CD28-induced IL-2 release in primary rat lymph-nodes purified T cells. Control rat were sacrificed and lymph-nodes were harvested. T cells further were purified (using magnetic negative selection) and plated into 96-well plates at 200,000 cells/well. Cells were treated with anti-rat CD3 and anti-rat CD28 antibodies (2 µg/mL). JNK inhibitor with SEQ ID NO: 172 was added to the cultures 1 h before CD3/CD28 treatment and IL-2 release was assessed in supernatant 24 h after treatment.

Figure 16:
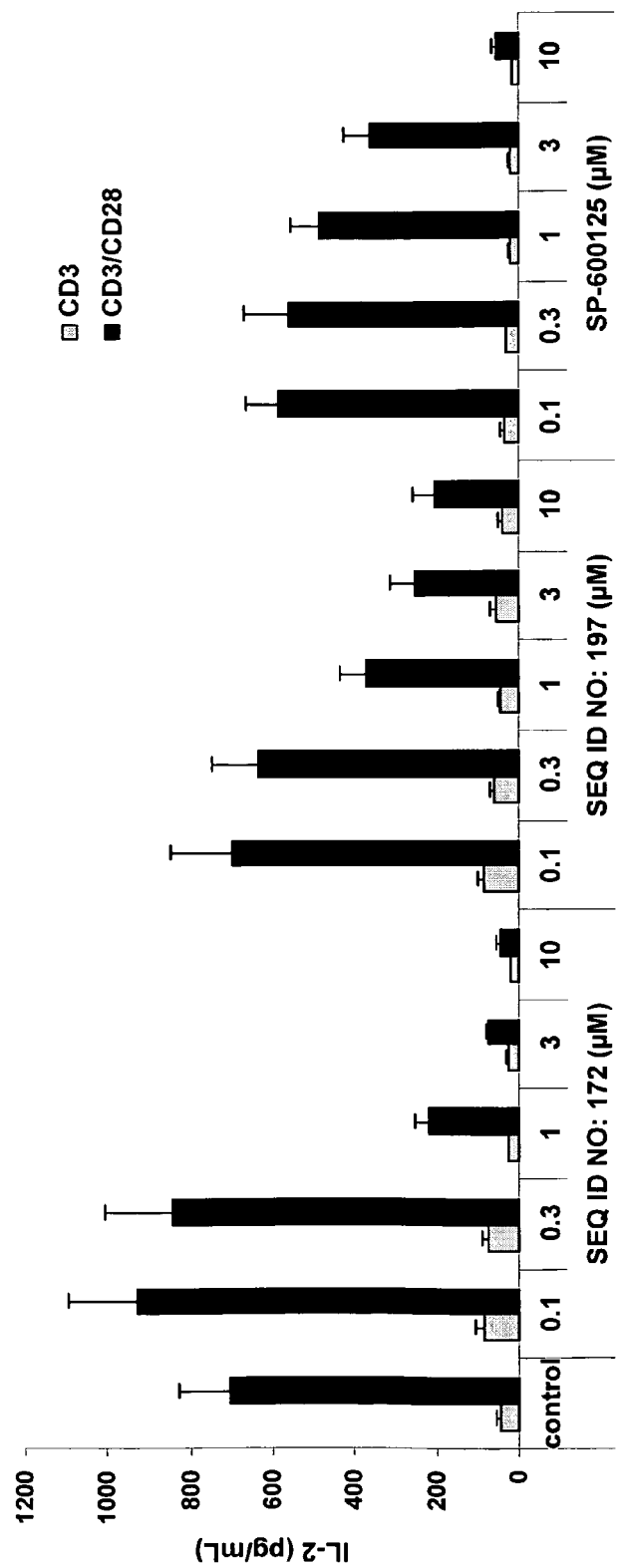

FIG. 16 Dose-dependent inhibition of CD3/CD28-induced IL-2 release in primary rat lymph-nodes purified T cells: Comparison of several JNK inhibitors, namely SEQ ID NOs: 172, 197 and SP600125.

Figure 17:
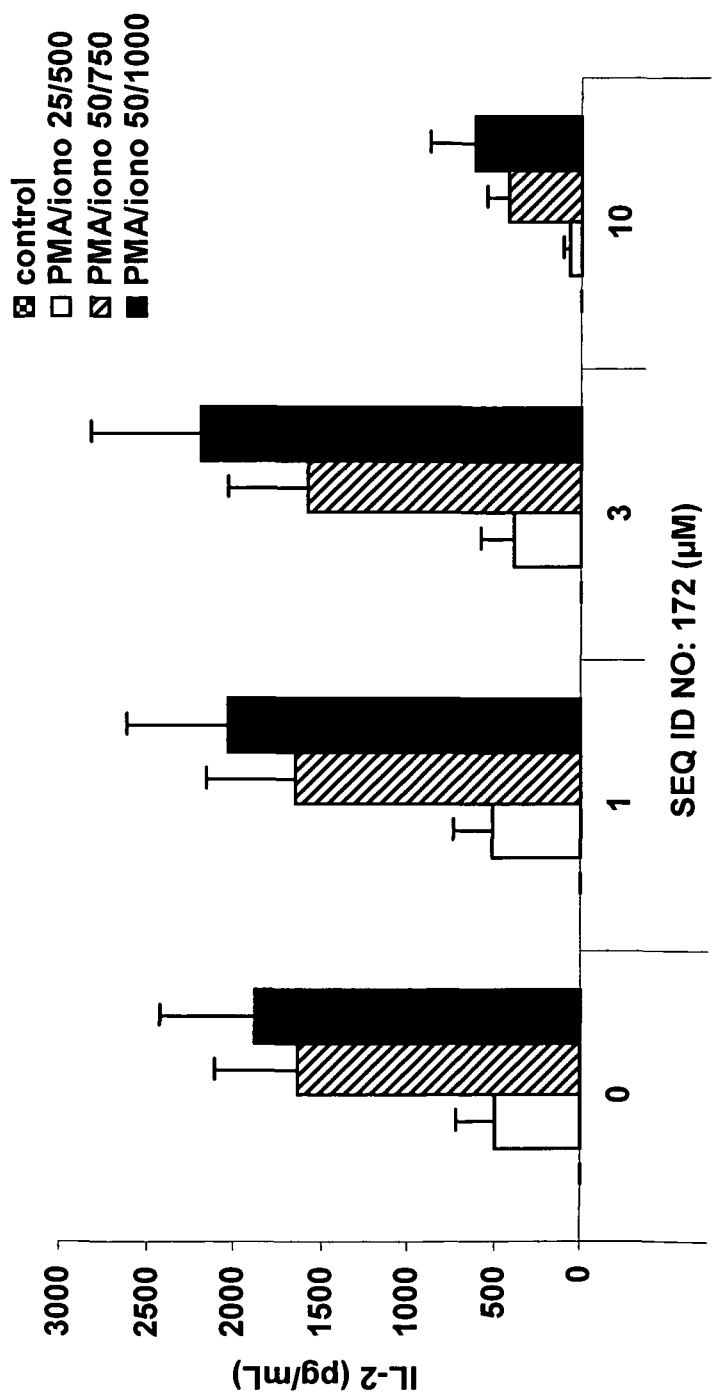

FIG. 17 Dose dependent inhibition of IL-2 release in rat whole blood stimulated with PMA+ionomycin. JNK inhibitor with SEQ ID NO: 172 was added at three different concentrations, namely 1, 3 and 10 µM 1 h before stimulation with PMA+ionomycin. Three doses of activators were added (25/500 ng/mL, 50/750 ng/mL and 50/1000 ng/mL) for 4 h. IL-2 release was assessed in supernatant. JNK inhibitor with SEQ ID NO: 172 at 10 µM did efficiently reduce PMA-iono-induced IL-2 release at the three tested activator concentrations.

Figure 18:
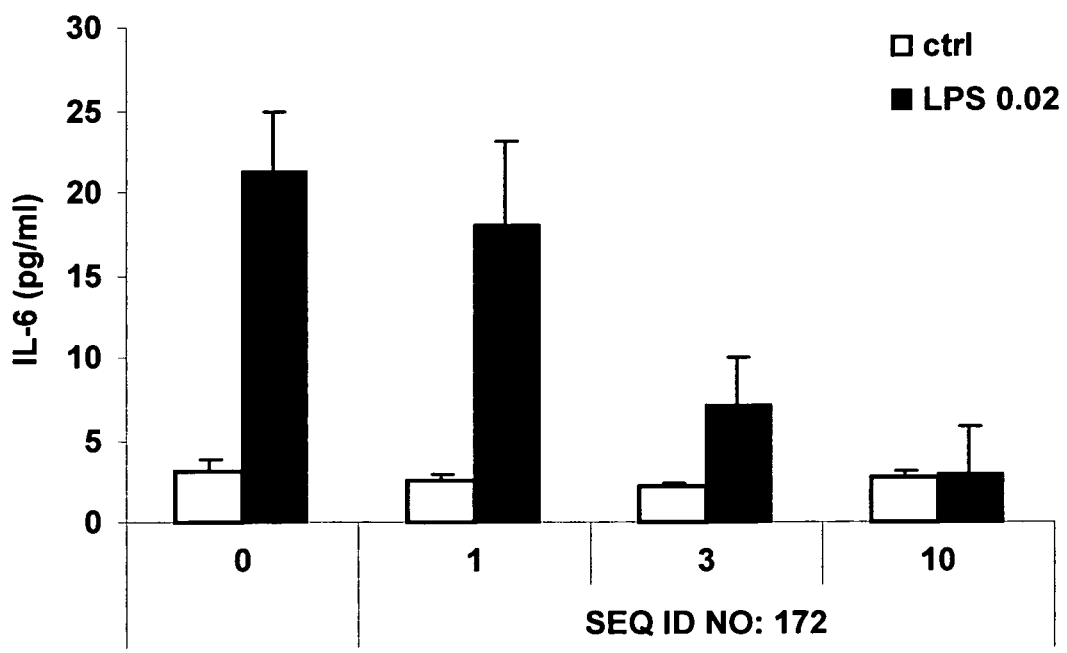

FIG. 18 JNK inhibition and IL-6 release in human whole blood. The JNK inhibitor with SEQ ID NO: 172 was added at three different concentrations, namely 1, 3 and 10 µM 1 h before whole blood stimulation with LPS (0.02 ng/mL) for 4 hours. The JNK inhibitor with SEQ ID NO: 172 did reduce the LPS-induced IL-6 release in a dose-dependent manner.

Figure 19:
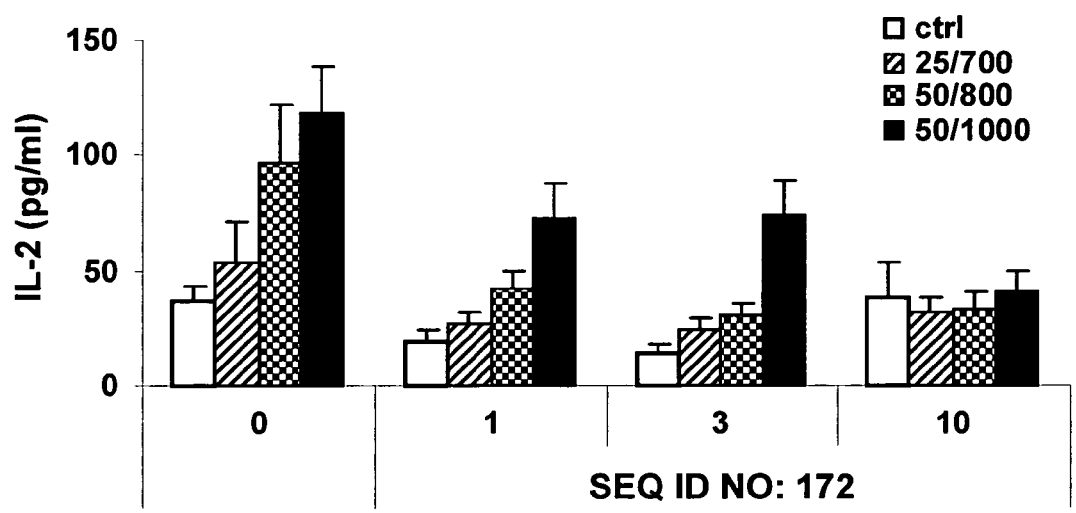

FIG. 19 JNK inhibition and IL-2 release in human whole blood. The JNK inhibitor with SEQ ID NO: 172 was added at three different concentrations, namely 1, 3 and 10 µM 1 h before whole blood stimulation with PMA+ionomycin (25/700 ng/mL, 50/800 ng/ml and 50/1000 ng/mL) for 4 hours. The JNK inhibitor with SEQ ID NO: 172 did reduce the PMA+ionomycin-induced IL-2 release in a dose-dependent manner.

Figure 20:
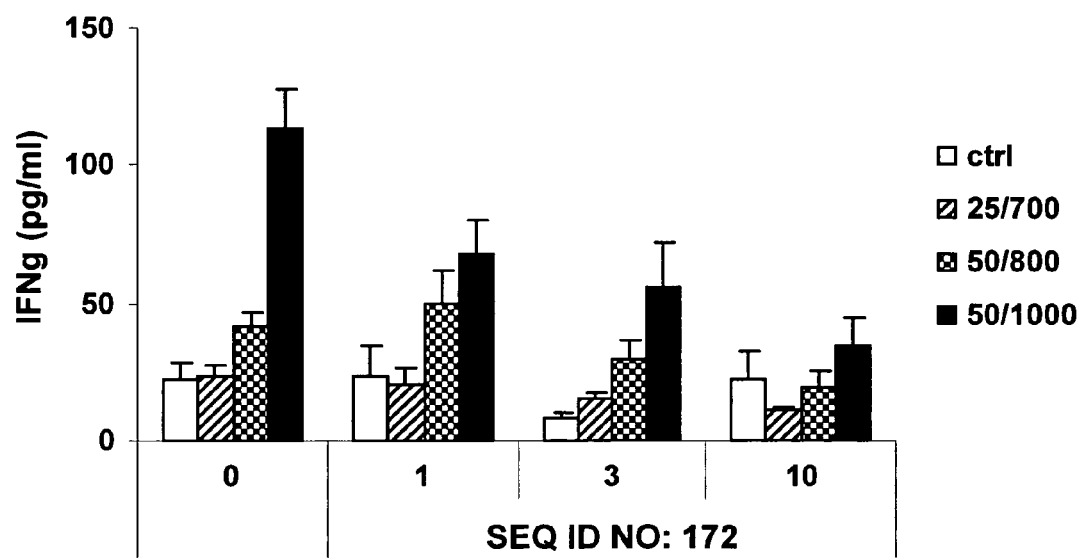

FIG. 20 JNK inhibition and IFN-γ release in human whole blood. The JNK inhibitor with SEQ ID NO: 172 was added at three different concentrations, namely 1, 3 and 10 µM 1 h before whole blood stimulation with PMA+ionomycin (25/700 ng/mL, 50/800 ng/ml and 50/1000 ng/mL) for 4 hours. The JNK inhibitor with SEQ ID NO: 172 did reduce the PMA+ionomycin-induced IFN-γ release in a dose-dependent manner.

Figure 21:
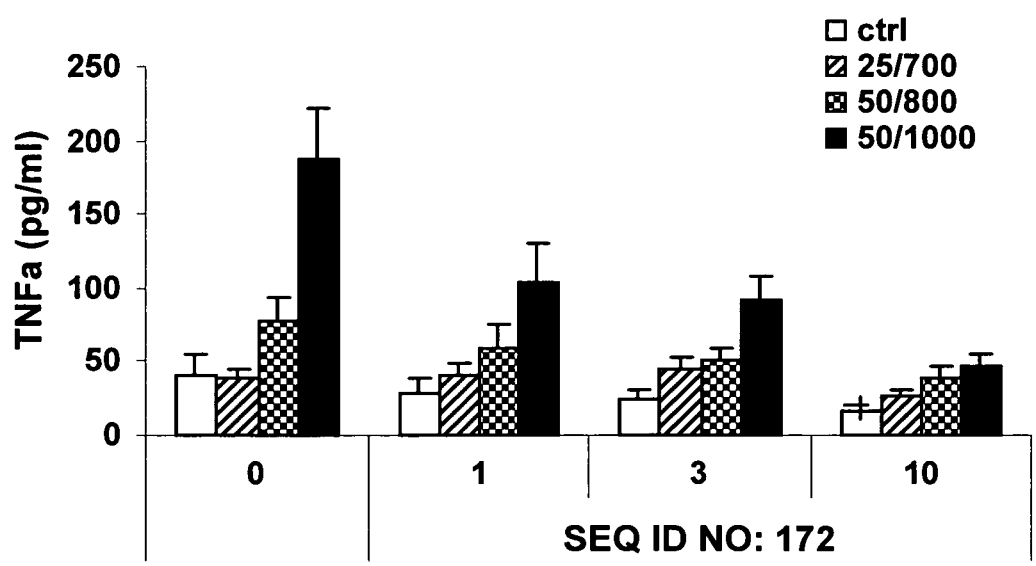

FIG. 21 JNK inhibition and TNF-α release in human whole blood. The JNK inhibitor with SEQ ID NO: 172 was added at three different concentrations, namely 1, 3 and 10 µM 1 h before whole blood stimulation with PMA+ionomycin (25/700 ng/mL, 50/800 ng/ml and 50/1000 ng/mL) for 4 hours. The JNK inhibitor with SEQ ID NO: 172 did reduce the PMA+ionomycin-induced TNF-α release in a dose-dependent manner.

Figure 22:
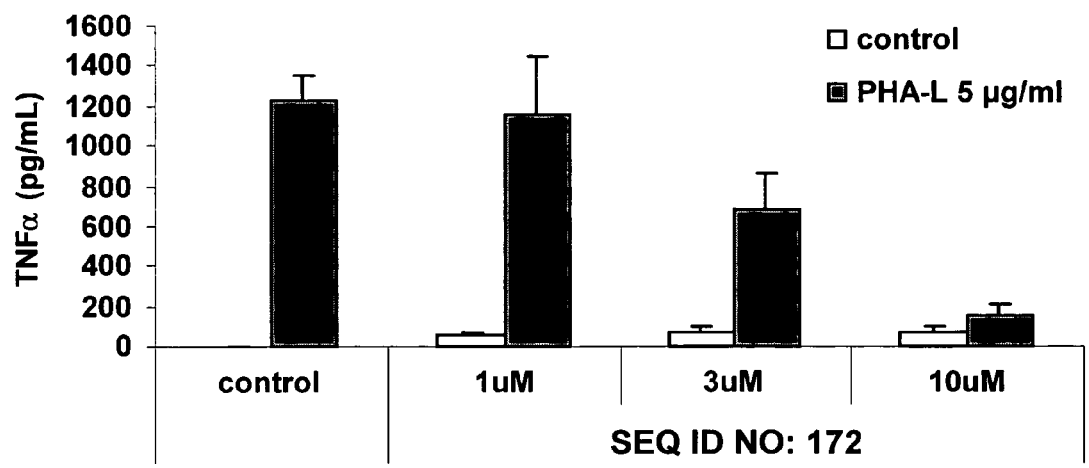

FIG. 22 JNK inhibition and TNF-α release in human whole blood. The JNK inhibitor with SEQ ID NO: 172 was added at three different concentrations, namely 1, 3 and 10 µM 1 h before whole blood stimulation with PHA-L (5 µg/mL) for 3 days. The JNK inhibitor with SEQ ID NO: 172 did reduce the PHA-L-induced TNF-α release in a dose-dependent manner.

Figure 23:
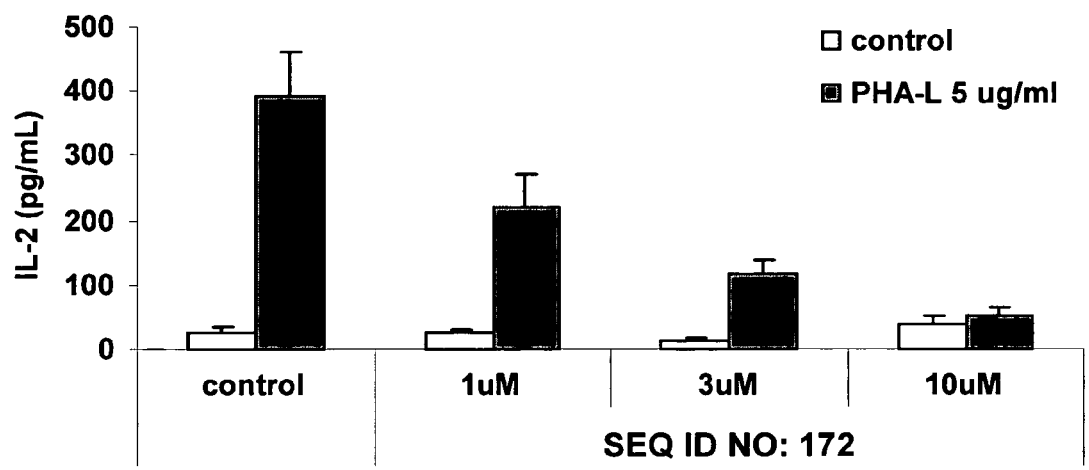

FIG. 23 JNK inhibition and IL-2 release in human whole blood. The JNK inhibitor with SEQ ID NO: 172 was added at three different concentrations, namely 1, 3 and 10 µM 1 h before whole blood stimulation with PHA-L (5 µg/mL) for 3 days. The JNK inhibitor with SEQ ID NO: 172 did reduce the PHA-L-induced IL-2 release in a dose-dependent manner.

Figure 24:
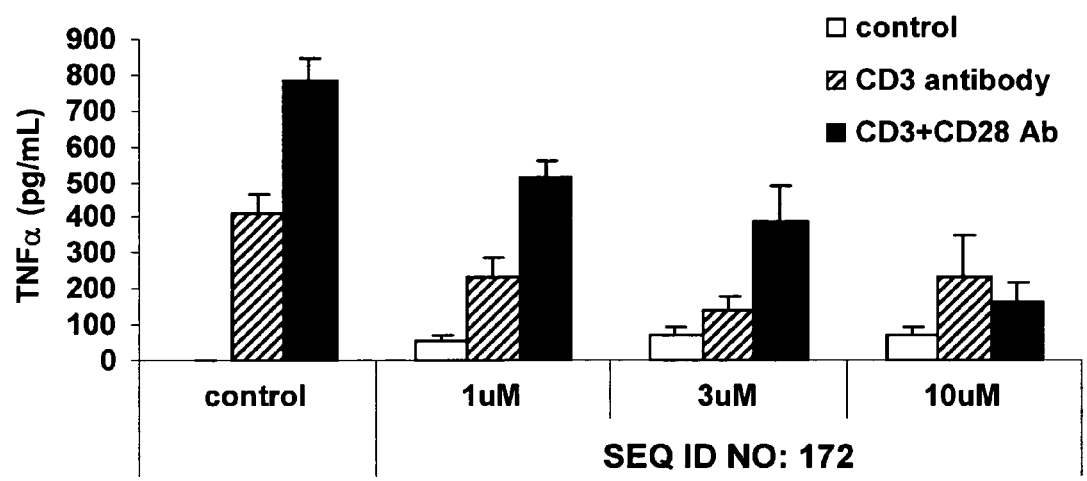

FIG. 24 JNK inhibition and TNF-α release in human whole blood. The JNK inhibitor with SEQ ID NO: 172 was added at three different concentrations, namely 1, 3 and 10 µM 1 h before whole blood stimulation with CD3+/–CD28 antibodies (2 µg/mL) for 3 days. The JNK inhibitor with SEQ ID NO: 172 did reduce the CD3/CD28-induced TNF-α release in a dose-dependent manner.

JNK INHIBITORS

In a first aspect the present invention relates to a JNK inhibitor, which comprises an inhibitory (poly-)peptide sequence according to the following general formula:

$$X_1-X_2-X_3-R-X_4-X_5-X_6-L-X_7-L-X_8, \quad \text{(SEQ ID NO: 1)}$$

wherein X1 is an amino acid selected from amino acids R, P, Q and r,
wherein X2 is an amino acid selected from amino acids R, P, G and r,
wherein X3 is an amino acid selected from amino acids K, R, k and r,
wherein X4 is an amino acid selected from amino acids P and K,
wherein X5 is an amino acid selected from amino acids T, a, s, q, k or is absent,
wherein X6 is an amino acid selected from amino acids T, D and A,
wherein X7 is an amino acid selected from amino acids N, n, r and K; and
wherein X8 is an amino acid selected from F, f and w,
with the proviso that at least one, at least two, at least three, at least four, at least five or six of the amino acids selected from the group consisting of X1, X2, X3, X5, X7 and X8 is/are a D-amino acid(s), preferably with the proviso that at least one, at least two, at least three or four of the amino acids selected from the group consisting of X3, X5, X7 and X8 is/are a D-amino acid(s).

The inhibitory (poly-)peptide sequence of the JNK inhibitor according to the present invention comprises L-amino acids and in most embodiments D-amino acids. Unless specified otherwise, L-amino acid residues are indicated herein in capital letters, while D amino acid residues are indicated in small letters. Glycine may be indicated in capital or small letters (since there is no D- or L-glycine). The amino acid sequences disclosed herein are always given from N— to C-terminus (left to right) unless specified otherwise. The given amino acid sequence may be modified or unmodified at the C- and/or N-terminus, e.g. acetylation at the C-terminus and/or amidation or modification with cysteamide at the N-terminus. For sake of clarity such possible but entirely optional modifications at the C- and/or N-terminus of the amino acid sequences disclosed herein are for sake of clarity not specifically indicated.

The JNK inhibitors of the present invention are (poly-)peptide inhibitors of the c-Jun N-terminal kinase (JNK). Said inhibitors inhibit the kinase activity of c-Jun N-terminal kinase (JNK), i.e. prevent or reduce the extent of phosphorylation of JNK substrates such as c-Jun, ATF2 and/or Elk-1. A person skilled in the art will understand that the term "inhibitor", as used herein, does not comprise compounds which irreversibly destroy the c-Jun N-terminal kinase (JNK) molecule and/or kinase activity. Furthermore, the term "inhibiting JNK activity" as used herein, refers to the inhibition of the kinase activity of c-Jun N-terminal kinase (JNK).

Furthermore, as used herein, a JNK inhibitor comprises at least one functional unit of a polymer of amino acids, i.e. a (poly-)peptide sequence. Moreover, this at least one functional polymer of amino acids provides for inhibition of JNK activity. The amino acid monomers of said inhibitory (poly-)peptide sequence are usually linked to each other via peptide bonds, but (chemical) modifications of said peptide bond(s) or of side chain residues may be tolerable, provided the inhibitory activity (inhibition of JNK activity) is not totally lost, i.e. the resulting chemical entity still qualifies as JNK inhibitor as functionally defined herein. The term "(poly-)peptide" shall not be construed as limiting the length of the (poly-)peptide unit. Preferably, the inhibitory (poly-)peptide sequence of the JNK inhibitors of the present invention is less than 500, 490, 480, 470, 460, 450, 440, 430, 420, 410, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 95, 90, 85, 80, 75, 70, 65, 60, 55, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, or less than 12 amino acids long. Preferably, the inhibitory (poly-)peptide sequence does not have less than 10 amino acid residues, more preferably not less than 11 amino acid residues.

Furthermore, a "JNK inhibitor" of the present invention inhibits JNK activity, e.g. exhibits with regard to the inhibition of human JNK mediated phosphorylation of a c-Jun substrate (SEQ ID NO: 198) an IC 50 value of:
a) less than 3000 nM, more preferably less than 2000 nM, even more preferably less than 1000 nM, even more preferably less than 500 nM, even more preferably less than 250 nM, even more preferably less than 200 nM, even more preferably less than 150 nM, most preferably less than 100 nM with regard to inhibition of human JNK1,
b) less than 3000 nM, more preferably less than 2000 nM, even more preferably less than 1000 nM, even more preferably less than 500 nM, even more preferably less than 250 nM, even more preferably less than 200 nM, even more preferably less than 150 nM, most preferably less than 100 nM with regard to inhibition of human JNK2, and/or
c) less than 3000 nM, more preferably less than 2000 nM, even more preferably less than 1000 nM, even more preferably less than 500 nM, even more preferably less than 250 nM, even more preferably less than 200 nM, even more preferably less than 150 nM, most preferably less than 100 nM with regard to inhibition of human JNK3.

For some applications it is preferred that the inhibitor inhibits human JNK2 and/or human JNK3 according to the above definition, but not JNK1 according to the above definition.

Whether JNK activity is inhibited or not, may easily be assessed by a person skilled in the art. There are several methods know in the art. One example is a radioactive kinase assay or a non-radioactive kinase assay (e.g. Alpha screen test; see for example Guenat et al. J Biomol Screen, 2006; 11: pages 1015-1026).

A JNK inhibitor according to the present invention may thus for example comprise an inhibitory (poly-)peptide sequence according to any of SEQ ID NOs: 2 to 27 (see table 1).

TABLE 1

Examples for inhibitory (poly-) peptide sequences of JNK-inhibitors according to the present invention

| Amino acid sequence | SEQ ID NO: |
|---|---|
| rPKRPTTLNLF | 2 |
| RPkRPTTLNLF | 3 |
| RPKRPaTLNLF | 4 |
| RPKRPTTLnLF | 5 |
| RPKRPTTLrLF | 6 |
| RPKRPTTLNLf | 7 |
| RPkRPaTLNLf | 8 |
| RPkRPTTLNLf | 9 |
| RPkRPTTLrLf | 10 |
| RRrRPTTLNLf | 11 |
| QRrRPTTLNLf | 12 |
| RPkRPTTLNLw | 13 |
| RPkRPTDLNLf | 14 |
| RRrRPTTLrLw | 15 |
| QRrRPTTLrLw | 16 |
| RRrRPTDLrLw | 17 |
| QRrRPTDLrLw | 18 |
| RRrRPaTLNLf | 19 |
| QRrRPaTLNLf | 20 |
| RrKRPaTLNLf | 21 |
| RPkRPsTLNLf | 22 |
| RPkRPqTLNLf | 23 |
| RPkRPkTLNLf | 24 |
| rGKRKALKLf | 25 |
| rGKRKALrLf | 26 |
| RRrRKALrLf | 27 |

The JNK inhibitor according to the present invention may also be a JNK inhibitor (variant) which comprises an inhibitory (poly-)peptide sequence sharing at least 50%, more preferably at least 55%, more preferably at least 60%, more preferably at least 65%, more preferably at least 70%, more preferably at least 75%, more preferably at least 80%, more preferably at least 85%, most preferably at least 90% sequence identity with a sequence selected from SEQ ID NOs: 1-27, in particular with SEQ ID NO: 8, with the proviso that with regard to the respective sequence selected from SEQ ID NOs: 1-27, such inhibitory (poly-)peptide sequence sharing sequence identity a) maintains the L-arginine (R) residue on position 4,
b) maintains the two L-leucine (L) residues at position 8 and 10 (positions 7 and 9 with regard to SEQ ID NOs: 25-27),
c) exhibits one, two, three, four, five or six D-amino acid(s) at the respective positions corresponding to the amino acids selected from the group consisting of X1, X2, X3, X5, X7 and X8 of SEQ ID NO: 1 and respective positions in SEQ ID NOs: 2-27, more preferably exhibits one, two, three or four D-amino acid(s) at the positions corresponding to the amino acids selected from the group consisting of X3, X5, X7 and X8 of SEQ ID NO: 1 and respective positions in SEQ ID NOs: 2-27, and
d) still inhibits JNK activity (i.e. is a JNK inhibitor as defined herein).

Certainly, variants disclosed herein (in particular JNK inhibitor variants comprising an inhibitory (poly-)peptide sequence sharing—within the above definition—a certain degree of sequence identity with a sequence selected from SEQ ID NOs: 1-27), share preferably less than 100% sequence identity with the respective reference sequence.

In view of said definition and for sake of clarity the residues which may not be changed in variants of JNK inhibitors comprising SEQ ID NOs: 1-27 (see a) and b) in the above definition) are underlined in table 1.

The non-identical amino acids are preferably the result of conservative amino acid substitutions.

Conservative amino acid substitutions, as used herein, may include amino acid residues within a group which have sufficiently similar physicochemical properties, so that a substitution between members of the group will preserve the biological activity of the molecule (see e.g. Grantham, R. (1974), Science 185, 862-864). Particularly, conservative amino acid substitutions are preferably substitutions in which the amino acids originate from the same class of amino acids (e.g. basic amino acids, acidic amino acids, polar amino acids, amino acids with aliphatic side chains, amino acids with positively or negatively charged side chains, amino acids with aromatic groups in the side chains, amino acids the side chains of which can enter into hydrogen bridges, e.g. side chains which have a hydroxyl function, etc.). Conservative substitutions are in the present case for example substituting a basic amino acid residue (Lys, Arg, His) for another basic amino acid residue (Lys, Arg, His), substituting an aliphatic amino acid residue (Gly, Ala, Val, Leu, Ile) for another aliphatic amino acid residue, substituting an aromatic amino acid residue (Phe, Tyr, Trp) for another aromatic amino acid residue, substituting threonine by serine or leucine by isoleucine. Further conservative amino acid exchanges will be known to the person skilled in the art. The isomer form should preferably be maintained, e.g. K is preferably substituted for R or H, while k is preferably substituted for r and h.

Further possible substitutions within the above definition for JNK inhibitor variants are for example if:

a) one, two or more of X1, X2, X3, X4, X5, X6, X7 and/or X8 of SEQ ID NO: 1 or the corresponding positions within the respective sequence selected from SEQ ID NOs: 2-27 are substituted for A or a, b) X1 or X8 of SEQ ID NO: 1 or the corresponding position within the respective sequence selected from SEQ ID NOs: 2-27 is deleted;
c) X5 of SEQ ID NO: 1 or the corresponding position within the respective sequence selected from SEQ ID NOs: 2-27 is E, Y, L, V, F or K;
d) X5 of SEQ ID NO: 1 or the corresponding position within the respective sequence selected from SEQ ID NOs: 2-27 is E, L, V, F or K; or
e) one, two or three of X1, X2, X3 of SEQ ID NO: 1 or the corresponding positions within the respective sequence selected from SEQ ID NOs: 2-27 are neutral amino acids.

As used herein, the term "% sequence identity", has to be understood as follows: Two sequences to be compared are aligned to give a maximum correlation between the sequences. This may include inserting "gaps" in either one or both sequences, to enhance the degree of alignment. A % identity may then be determined over the whole length of each of the sequences being compared (so-called global alignment), that is particularly suitable for sequences of the same or similar length, or over shorter, defined lengths (so-called local alignment), that is more suitable for sequences of unequal length. In the above context, an amino acid sequence having a "sequence identity" of at least, for example, 95% to a query amino acid sequence, is intended to mean that the sequence of the subject amino acid sequence is identical to the query sequence except that the subject amino acid sequence may include up to five amino acid alterations per each 100 amino acids of the query amino acid sequence. In other words, to obtain an amino acid sequence having a sequence of at least 95% identity to a query amino acid sequence, up to 5% (5 of 100) of the amino acid residues in the subject sequence may be inserted or substituted with another amino acid or deleted. For purposes of determining sequence identity, the substitution of an L-amino acid for a D-amino acid (and vice versa) is considered to yield a non-identical residue, even if it is merely the D- (or L-isomer) of the very same amino acid.

Methods for comparing the identity and homology of two or more sequences are well known in the art. The percentage to which two sequences are identical can for example be determined by using a mathematical algorithm. A preferred, but not limiting, example of a mathematical algorithm which can be used is the algorithm of Karlin et al. (1993), PNAS USA, 90:5873-5877. Such an algorithm is integrated in the BLAST family of programs, e.g. BLAST or NBLAST program (see also Altschul et at, 1990, J. Mol. Biol. 215, 403-410 or Altschul et al. (1997), Nucleic Acids Res, 25:3389-3402), accessible through the home page of the NCBI at world wide web site ncbi.nlm.nih.gov) and FASTA (Pearson (1990), Methods Enzymol. 183, 63-98; Pearson and Lipman (1988), Proc. Natl. Acad. Sci. U.S.A 85, 2444-2448.). Sequences which are identical to other sequences to a certain extent can be identified by these programmes. Furthermore, programs available in the Wisconsin Sequence Analysis Package, version 9.1 (Devereux et al, 1984, Nucleic Acids Res., 387-395), for example the programs BESTFIT and GAP, may be used to determine the % identity between two polypeptide sequences. BESTFIT uses the "local homology" algorithm of (Smith and Waterman (1981), J. Mol. Biol. 147, 195-197.) and finds the best single region of similarity between two sequences.

Certainly, the JNK inhibitor according to present invention may comprise—aside of the inhibitory (poly-)peptide sequence mentioned above—additional sequences, domains, labels (e.g. fluorescent or radioactive labels), epitopes etc. as long as the ability to inhibit JNK activity as defined herein is not lost. For example, the JNK inhibitor according to the present invention may also comprise a transporter sequence. A "transporter sequence" as used herein, is a (poly-)peptide sequence providing for translocation of the molecule it is attached to across biological membranes. Accordingly, a JNK inhibitor according to the present invention comprising a transporter sequence is preferably capable of translocating across biological membranes. Thus, such JNK inhibitor of the present invention may more readily enter a cell, a cellular subcompartment and/or into the nucleus of a cell.

Said transporter sequence may be joined for example (e.g. directly) N-terminally or (e.g. directly) C-terminally to the inhibitory (poly-)peptide sequence of the JNK inhibitor. The transporter sequence and the inhibitory (poly-)peptide sequence may also be spaced apart, e.g. may be separated by intermediate sequences. It is also contemplated that the transporter sequence may be positioned entirely elsewhere in the JNK inhibitor molecule than the inhibitory (poly-)peptide sequence, in particular if the JNK inhibitor is a more complex molecule (e.g. comprising several domains, is a multimeric conjugate etc.). It is also contemplated that the transporter sequence and the inhibitory (poly-)peptide sequence may overlap as long as the JNK inhibitory activity is maintained. Examples for such overlap are given further below.

Transporter sequences for use with the JNK inhibitor of the present invention may be selected from, without being limited thereto, transporter sequences derived from HIV TAT (HIV), e.g. native proteins such as e.g. the TAT protein (e.g. as described in U.S. Pat. Nos. 5,804,604 and 5,674,980, each of these references being incorporated herein by reference), HSV VP22 (Herpes simplex) (described in e.g. WO 97/05265; Elliott and O'Hare, Cell 88:223-233 (1997)), non-viral proteins (Jackson et al, Proc. Natl. Acad. Sci. USA 89:10691-10695 (1992)), transporter sequences derived from Antennapedia, particularly from *Drosophila antennapedia* (e.g. the antennapedia carrier sequence thereof), FGF, lactoferrin, etc. or derived from basic peptides, e.g. peptides having a length of 5 to 15 amino acids, preferably 10 to 12 amino acids and comprising at least 80%, more preferably 85% or even 90% basic amino acids, such as e.g. arginine, lysine and/or histidine, or may be selected from e.g. arginine rich peptide sequences, such as RRRRRRRRR ($R_9$; SEQ ID NO: 152), RRRRRRRR ($R_8$; SEQ ID NO: 153), RRRRRRR ($R_7$; SEQ ID NO: 154), RRRRRR ($R_6$, SEQ ID NO: 155), RRRRR ($R_5$, SEQ ID NO: 156) etc., from VP22, from PTD-4 proteins or peptides, from RGD-$K_{16}$, from PEPT1/2 or PEPT1/2 proteins or peptides, from SynB3 or SynB3 proteins or peptides, from PC inhibitors, from P21 derived proteins or peptides, or from JNKI proteins or peptides.

Examples of transporter sequences for use in the JNK inhibitor of the present invention are in particular, without being limited thereto, basic transporter sequences derived from the HIV-1 TAT protein. Preferably, the basic transporter sequence of the HIV-1 TAT protein may include sequences from the human immunodeficiency virus HIV-1 TAT protein, e.g. as described in, e.g., U.S. Pat. Nos. 5,804,604 and 5,674,980, each incorporated herein by reference. In this context, the full-length HIV-1 TAT protein has 86 amino acid residues encoded by two exons of the HIV TAT gene. TAT amino acids 1-72 are encoded by exon 1, whereas amino acids 73-86 are encoded by exon 2. The full-length TAT protein is characterized by a basic region which contains two lysines and six arginines (amino acids 49-57) and a cysteine-rich region which contains seven cysteine residues (amino acids 22-37). The basic region (i.e., amino acids 49-57) was thought to be important for nuclear localization. Ruben, S. et al, J. Virol. 63: 1-8 (1989); Hauber, J. et al., J. Virol. 63 1181-1187 (1989).

The cysteine-rich region mediates the formation of metal-linked dimers in vitro (Frankel, A. D. et al, Science 240: 70-73 (1988); Frankel, A. D. et al, Proc. Natl. Acad. Sci USA 85: 6297-6300 (1988)) and is essential for its activity as a trans-activator (Garcia, J. A. et al., EMBO J. 7: 3143 (1988); Sadaie, M. R. et al., J. Virol. 63:1 (1989)). As in other regulatory proteins, the N-terminal region may be involved in protection against intracellular proteases (Bachmair, A. et al., Cell 56: 1019-1032 (1989)). Preferred TAT transporter sequences for use in the JNK inhibitor of the present invention are preferably characterized by the presence of the TAT basic region amino acid sequence (amino acids 49-57 of naturally-occurring TAT protein); the absence of the TAT cysteine-rich region amino acid sequence (amino acids 22-36 of naturally-occurring TAT protein) and the absence of the TAT exon 2-encoded carboxy-terminal domain (amino acids 73-86 of naturally-occurring TAT protein). More preferably, the transporter sequence in the JNK inhibitor of the present invention may be selected from an amino acid sequence containing TAT residues 48-57 or 49 to 57 or variants thereof.

Preferably, the transporter sequence in a given JNK inhibitor of the present invention also exhibits D-amino acids, for example in order to improve stability towards proteases. Particularly preferred are transporter sequences which exhibit a specific order of alternating D- and L-amino acids. Such order of alternating D- and L-amino acids (the motif) may follow— without being limited thereto—the pattern of any one of SEQ ID NOs: 28-30:

$d_l LLL_x d_m LLL_y d_n$;  (SEQ ID NO: 28)

$dLLLd(LLLd)_a$;  (SEQ ID NO: 29)
and/or $dLLLdLLLd$;  (SEQ ID NO: 30)

wherein:
d is a D-amino acid;
L is a L-amino acid;
a is 0-3, preferably 0-2, more preferably 0, 1, 2 or 3, even more preferably 0, 1, or 2 and most preferably 1;
l, m and n are independently from each other 1 or 2, preferably 1;
x and y are independently from each other 0, 1 or 2, preferably 1.

Said order of D- and L-amino acids (motif) becomes relevant when the transporter sequence is synthesized, i.e. while the amino acid sequence (i.e. the type of side chain residues) remains unaltered, the respective isomers alternate. For example, a known transporter sequence derived from HIV TAT is RKKRRQRRR (SEQ ID NO: 43). Applying the D-/L amino acid order of SEQ ID NO: 30 thereto would yield rKKRrQRRr (SEQ ID NO: 46).

In a particular embodiment the transporter sequence of the JNK inhibitor of the present invention may comprise at least one sequence according to rXXXrXXXr (SEQ ID NO: 31), wherein:
r represents an D-enantiomeric arginine;
X is any L-amino acid (including glycine);
and wherein each X may be selected individually and independently of any other X within SEQ ID NO: 31. Preferably at least 4 out of said 6×L-amino acids within SEQ ID NO: 31 are K or R. In another embodiment the JNK inhibitor according to the present invention comprises the transporter sequence $rX_1X_2X_3rX_4X_5X_6r$ (SEQ ID NO: 32), wherein $X_1$ is K, $X_2$ is K, $X_3$ is R and $X_4$, $X_5$, and $X_6$ are any L-amino acid (including glycine) selected independently from each other. Similarly, the transporter sequence of the JNK inhibitor according to the present invention may comprise the sequence $rX_1X_2X_3rX_4X_5X_6r$ (SEQ ID NO: 33), wherein $X_4$ is Q, $X_5$ is R, $X_6$ is R and $X_1$, $X_2$, and $X_3$ are any L-amino acid (including glycine) selected independently from each other. The inventive JNK inhibitor may also comprise the sequence $rX_1X_2X_3rX_4X_5X_6r$ (SEQ ID NO: 34), wherein one, two, three, four, five or six X amino acid residues are chosen from the group consisting of: $X_1$ is K, $X_2$ is K, $X_3$ is R, $X_4$ is Q, $X_5$ is R, $X_6$ is R, while the remaining X amino acid residues not selected from above group may be any L-amino acid (including glycine) and are selected independently from each other. $X_1$ is then preferably Y and/or $X_4$ is preferably K or R.

Examples of transporter sequences for use in the inventive JNK inhibitor molecule may be selected, without being limited thereto, from sequences as given in table 2 below, (SEQ ID NOs: 31-170) or from any fragment or variant or chemically modified derivative thereof (preferably it retains the function of translocating across a biological membrane).

TABLE 2

Examples for transporter (poly-)peptide sequences for use in the JNK-inhibitors according to the present invention

| SEQUENCE/PEPTIDE NAME | SEQ ID NO | AA | SEQUENCE |
|---|---|---|---|
| r3 (generic) | 31 | 9 | rXXXrXXXr |
| r3 (generic; right half) | 32 | 9 | rKKRrX$_4$X$_5$X$_6$r |
| r3 (generic; left half) | 33 | 9 | rX$_1$X$_2$X$_3$rQRRr |
| r3 (generic; individual) | 34 | 9 | rX$_1$X$_2$X$_3$rX$_4$X$_5$X$_6$r |
| TAT (1-86) | 35 | 86 | MEPVDPRLEP WKHPGSQPKT ACTNCYCKKC CFHCQVCFIT KALGISYGRK KRRQRRRPPQ GSQTHQVSLS KQPTSQSRGD PTGPKE |
| TAT (37-72) | 36 | 36 | CFITKALGIS YGRKKRRQRR RPPQGSQTHQ VSLSKQ |
| TAT (37-58) | 37 | 22 | CFITKALGIS YGRKKRRQRR RP |
| TAT (38-58)GGC | 38 | 24 | FITKALGISY GRKKRRQRRR PGGC |

TABLE 2 -continued

Examples for transporter (poly-)peptide sequences for use in the JNK-inhibitors according to the present invention

| SEQUENCE/PEPTIDE NAME | SEQ ID NO | AA | SEQUENCE |
|---|---|---|---|
| TAT CGG(47-58) | 39 | 15 | CGGYGRKKRR QRRRP |
| TAT (47-58)GGC | 40 | 15 | YGRKKRRQRR RPGGC |
| TAT (1-72) Mut Cys/Ala 72 | 41 | 56 | MEPVDPRLEP WKHPGSQPKT AFITKALGIS YGRKKRRQRR RPPQGSQTHQ VSLSKQ |
| L-TAT (s1a) | 42 | 10 | GRKKRRQRRR (NH$_2$-GRKKRRQRRR-COOH) |
| L-TAT (s1b) | 43 | 9 | RKKRRQRRR (NH$_2$-GRKKRRQRRR-COON) |
| L-TAT (s1c) | 44 | 11 | YDRKKRRQRRR |
| D-TAT | 45 | 9 | rrrqrrkkr |
| r$_3$-L-TAT | 46 | 9 | rKKRrQRRr |
| r$_3$-L-TATi | 47 | 9 | rRRQrRKKr |
| βA-r$_3$-L-TAT | 48 | 9 | βA-rKKRrQRRr (βA: beta alanine) |
| βA-r$_3$-L-TATi | 49 | 9 | βA-rRRQrRKKr (βA: beta alanine) |
| FITC-βA-r3-L-TAT | 50 | 9 | FITC-βA-rKKRrQRRr (βA: beta alanine) |
| FITC-βA-r3-L-TATi | 51 | 9 | FITC-βA-rRRQrRKKr (βA: beta alanine) |
| TAT(s2-1) | 52 | 9 | rAKRrQRRr |
| TAT(s2-2) | 53 | 9 | rKARrQRRr |
| TAT(s2-3) | 54 | 9 | rKKArQRRr |
| TAT(s2-4) | 55 | 9 | rKKRrARRr |
| TAT(s2-5) | 56 | 9 | rKKRrQARr |
| TAT(s2-6) | 57 | 9 | rKKRrQRAr |
| TAT(s2-7) | 58 | 9 | rDKRrQRRr |
| TAT(s2-8) | 59 | 9 | rKDRrQRRr |
| TAT(s2-9) | 60 | 9 | rKKDrQRRr |
| TAT(s2-10) | 61 | 9 | rKKRrDRRr |
| TAT(s2-11) | 62 | 9 | rKKRrQDRr |
| TAT(s2-12) | 63 | 9 | rKKRrQRDr |
| TAT(s2-13) | 64 | 9 | rEKRrQRRr |
| TAT(s2-14) | 65 | 9 | rKERrQRRr |
| TAT(s2-15) | 66 | 9 | rKKErQRRr |
| TAT(s2-16) | 67 | 9 | rKKRrERRr |
| TAT(s2-17) | 68 | 9 | rKKRrQERr |
| TAT(s2-18) | 69 | 9 | rKKRrQREr |
| TAT(s2-19) | 70 | 9 | rFKRrQRRr |
| TAT(s2-20) | 71 | 9 | rKFRrQRRr |
| TAT(s2-21) | 72 | 9 | rKKFrQRRr |
| TAT(s2-22) | 73 | 9 | rKKRrFRRr |
| TAT(s2-23) | 74 | 9 | rKKRrQFRr |

TABLE 2 -continued

Examples for transporter (poly-)peptide sequences for use in the JNK-inhibitors according to the present invention

| SEQUENCE/PEPTIDE NAME | SEQ ID NO | AA | SEQUENCE |
|---|---|---|---|
| TAT(s2-24) | 75 | 9 | rKKRrQRFr |
| TAT(s2-25) | 76 | 9 | rRKRrQRRr |
| TAT(s2-26) | 77 | 9 | rKRRrQRRr |
| TAT(s2-27) | 78 | 9 | rKKKrQRRr |
| TAT(s2-28) | 79 | 9 | rKKRrRRRr |
| TAT(s2-29) | 80 | 9 | rKKRrQKRr |
| TAT(s2-30) | 81 | 9 | rKKRrQRKr |
| TAT(s2-31) | 82 | 9 | rHKRrQRRr |
| TAT(s2-32) | 83 | 9 | rKHRrQRRr |
| TAT(s2-33) | 84 | 9 | rKKHrQRRr |
| TAT(s2-34) | 85 | 9 | rKKRrHRRr |
| TAT(s2-35) | 86 | 9 | rKKRrQHRr |
| TAT(s2-36) | 87 | 9 | rKKRrQRHr |
| TAT(s2-37) | 88 | 9 | rIKRrQRRr |
| TAT(s2-38) | 89 | 9 | rKIRrQRRr |
| TAT(s2-39) | 90 | 9 | rKKIrQRRr |
| TAT(s2-40) | 91 | 9 | rKKRrIRRr |
| TAT(s2-41) | 92 | 9 | rKKRrQIRr |
| TAT(s2-42) | 93 | 9 | rKKRrQRIr |
| TAT(s2-43) | 94 | 9 | rLKRrQRRr |
| TAT(s2-44) | 95 | 9 | rKLRrQRRr |
| TAT(s2-45) | 96 | 9 | rKKLrQRRr |
| TAT(s2-46) | 97 | 9 | rKKRrLRRr |
| TAT(s2-47) | 98 | 9 | rKKRrQLRr |
| TAT(s2-48) | 99 | 9 | rKKRrQRLr |
| TAT(s2-49) | 100 | 9 | rMKRrQRRr |
| TAT(s2-50) | 101 | 9 | rKMRrQRRr |
| TAT(s2-51) | 102 | 9 | rKKMrQRRr |
| TAT(s2-52) | 103 | 9 | rKKRrMRRr |
| TAT(s2-53) | 104 | 9 | rKKRrQMRr |
| TAT(s2-54) | 105 | 9 | rKKRrQRMr |
| TAT(s2-55) | 106 | 9 | rNKRrQRRr |
| TAT(s2-56) | 107 | 9 | rKNRrQRRr |
| TAT(s2-57) | 108 | 9 | rKKNrQRRr |
| TAT(s2-58) | 109 | 9 | rKKRrNRRr |
| TAT(s2-59) | 110 | 9 | rKKRrQNRr |
| TAT(s2-60) | 111 | 9 | rKKRrQRNr |

TABLE 2 -continued

Examples for transporter (poly-)peptide sequences for use in the JNK-inhibitors according to the present invention

| SEQUENCE/PEPTIDE NAME | SEQ ID NO | AA | SEQUENCE |
|---|---|---|---|
| TAT(s2-61) | 112 | 9 | rQKRrQRRr |
| TAT(s2-62) | 113 | 9 | rKQRrQRRr |
| TAT(s2-63) | 114 | 9 | rKKQrQRRr |
| TAT(s2-64) | 115 | 9 | rKKRrKRRr |
| TAT(s2-65) | 116 | 9 | rKKRrQQRr |
| TAT(s2-66) | 117 | 9 | rKKRrQRQr |
| TAT(s2-67) | 118 | 9 | rSKRrQRRr |
| TAT(s2-68) | 119 | 9 | rKSRrQRRr |
| TAT(s2-69) | 120 | 9 | rKKSrQRRr |
| TAT(s2-70) | 121 | 9 | rKKRrSRRr |
| TAT(s2-71) | 122 | 9 | rKKRrQSRr |
| TAT(s2-72) | 123 | 9 | rKKRrQRSr |
| TAT(s2-73) | 124 | 9 | rTKRrQRRr |
| TAT(s2-74) | 125 | 9 | rKTRrQRRr |
| TAT(s2-75) | 126 | 9 | rKKTrQRRr |
| TAT(s2-76) | 127 | 9 | rKKRrTRRr |
| TAT(s2-77) | 128 | 9 | rKKRrQTRr |
| TAT(s2-78) | 129 | 9 | rKKRrQRTr |
| TAT(s2-79) | 130 | 9 | rVKRrQRRr |
| TAT(s2-80) | 131 | 9 | rKVRrQRRr |
| TAT(s2-81) | 132 | 9 | rKKVrQRRr |
| TAT(s2-82) | 133 | 9 | rKKRrVRRr |
| TAT(s2-83) | 134 | 9 | rKKRrQVRr |
| TAT(s2-84) | 135 | 9 | rKKRrQRVr |
| TAT(s2-85) | 136 | 9 | rWKRrQRRr |
| TAT(s2-86) | 137 | 9 | rKWRrQRRr |
| TAT(s2-87) | 138 | 9 | rKKWrQRRr |
| TAT(s2-88) | 139 | 9 | rKKRrWRRr |
| TAT(s2-89) | 140 | 9 | rKKRrQWRr |
| TAT(s2-90) | 141 | 9 | rKKRrQRWr |
| TAT(s2-91) | 142 | 9 | rYKRrQRRr |
| TAT(s2-92) | 143 | 9 | rKYRrQRRr |
| TAT(s2-93) | 144 | 9 | rKKYrQRRr |
| TAT(s2-94) | 145 | 9 | rKKRrYRRr |
| TAT(s2-95) | 146 | 9 | rKKRrQYRr |
| TAT(s2-96) | 147 | 9 | rKKRrQRYr |
| TAT(s2-97) | 148 | 8 | rKKRrQRr |

TABLE 2 -continued

Examples for transporter (poly-)peptide sequences for use in the JNK-inhibitors according to the present invention

| SEQUENCE/PEPTIDE NAME | SEQ ID NO | AA | SEQUENCE |
|---|---|---|---|
| TAT(s2-98) | 149 | 9 | rKKRrQRrK |
| TAT(s2-99) | 150 | 9 | rKKRrQRrR |
| $r_3R_6$ | 151 | 9 | rRRRrRRRr |
| $L-R_9$ | 152 | 9 | RRRRRRRRR |
| $L-R_8$ | 153 | 8 | RRRRRRRR |
| $L-R_7$ | 154 | 7 | RRRRRRR |
| $L-R_6$ | 155 | 6 | RRRRRR |
| $L-R_5$ | 156 | 5 | RRRRR |
| $r_9$ | 157 | 9 | rrrrrrrrr |
| $r_5R_4$ (D/L) | 158 | 9 | rRrRrRrRr |
| $r_5R_4$ (DD/LL) | 159 | 9 | rrRRrrRRr |
| PTD-4 | 160 | 11 | YARAAARQARA |
| PTD-4 (variant 1) | 161 | 11 | WARAAARQARA |
| PTD-4 (variant 2) | 162 | 11 | WARAQRAAARA |
| L-P1 Penetratin | 163 | 16 | RQVKVWFQNRRMKWKK |
| D-P1 Penetratin | 164 | 16 | KKWKMRRNQFWVKVQR |
| JNKI, bestfit | 165 | 17 | WKRAAARKARAMSLNLF |
| JNKI, bestfit (variant 1) | 166 | 17 | WKRAAARAARAMSLNLF |
| MDCK transcytose sequence | 167 | 9 | RYRGDLGRR |
| YKGL | 168 | 4 | YKGL |
| P1 | 169 | 4 | RRTK |
| P66 | 170 | 4 | RRPK |

As mentioned above, transporter sequences may also be selected from fragments or variants of the above sequences of table 2 (with the proviso that such fragment or variant retain preferably the function to provide for translocation across biological membranes). In this specific context, variants and/or fragments of those transporter sequences preferably comprise a peptide sequence sharing at least 10%, at least 20%, at least 30%, at least 40%, at least 50%, at least 60%, at least 70%, at least 80% or at least 85%, preferably at least 90%, more preferably at least 95% and most preferably at least 99% sequence identity over the whole length of the sequence of such a transporter sequence as defined in Table 2. In this specific context, a "fragment" of a transporter sequence as defined in Table 2, is preferably to be understood as a truncated sequence thereof, i.e. an amino acid sequence, which is N-terminally, C-terminally and/or intrasequentially truncated compared to the amino acid sequence of the original sequence.

Furthermore, a "variant" of a transporter sequence or its fragment as defined above, is preferably to be understood as a sequence wherein the amino acid sequence of the variant differs from the original transporter sequence or a fragment thereof as defined herein in one or more mutation(s), such as one or more substituted, (or, if necessary, inserted and/or deleted) amino acid(s). Preferably, variants of such a transporter sequence as defined above have the same biological function or specific activity compared to the respective original sequence, i.e. provide for transport, e.g. into cells or the nucleus. In this context, a variant of such a transporter sequence as defined above may for example comprise about 1 to 50, 1 to 20, more preferably 1 to 10 and most preferably 1 to 5, 4, 3, 2 or 1 amino acid alterations. Variants of such a transporter sequence as defined above may preferably comprise conservative amino acid substitutions. The concept of conservative amino acid substitutions is known in the art and has already been set out above for the JNK inhibitory (poly-)peptide sequence and applies here accordingly.

The length of a transporter sequence incorporated in the JNK inhibitor of the present invention may vary. It is contemplated that in some embodiments the transporter sequence of the JNK inhibitor according to the present invention is less than 150, less than 140, less than 130, less than 120, less than 110, less than 100, less than 90, less than 80, less than 70, less than 60, less than 50, less than 40, less than 30, less than 20, and/or less than 10 amino acids in length.

Whether a specific transporter sequence is still functional in the context of the JNK inhibitor according to the present invention may easily be determined by a person skilled in the art. For instance, the JNK inhibitor comprising a transporter domain may be fused to a label, e.g. a fluorescent protein such as GFP, a radioactive label, an enzyme, a fluorophore, an epitope etc. which can be readily detected in a cell. Then, the JNK inhibitor comprising the transporter sequence and the label is transfected into a cell or added to a culture supernatant and permeation of cell membranes can be monitored by using biophysical and biochemical standard methods (for example flow cytometry, (immuno)fluorescence microscopy etc.).

Specific examples of JNK inhibitors according to the present invention comprising a transporter sequence are given in table 3:

TABLE 3

Examples for JNK inhibitors comprising an inhibitory (poly-)peptide sequence and a transporter sequence

| Amino acid sequence | AA | SEQ ID NO: |
|---|---|---|
| rKKRrQRRrRPkRPTTLNLf | 20 | 171 |
| rKKRrQRRrRPkRPaTLNLf | 20 | 172 |
| rKKRrQRRrRPkRPTTLrLf | 20 | 173 |
| rKKRrQRRrRPTTLNLf | 17 | 174 |
| rKKRrQRrRPTTLNLf | 16 | 175 |
| rKKRrQRRrRPkRPTTLNLw | 20 | 176 |
| rKKRrQRRrRPkRPTDLNLf | 20 | 177 |
| rKKRrQRRrRPTTLrLw | 17 | 178 |
| rKKRrQRrRPTTLrLw | 16 | 179 |
| rKKRrQRRrRPTDLrLw | 17 | 180 |
| rKKRrQRrRPTDLrLw | 16 | 181 |
| rKKRrQRRrRPaTLNLf | 17 | 182 |
| rKKRrQRrRPaTLNLf | 16 | 183 |
| rKKRrQRrKRPaTLNLf | 17 | 184 |
| rKKRrQRRrRPkRPsTLNLf | 20 | 185 |
| rKKRrQRRrRPkRPqTLNLf | 20 | 186 |
| rKKRrQRRrRPkRPkTLNLf | 20 | 187 |
| rKKRrQRRrGKRKALKLf | 18 | 188 |
| rKKRrQRRrGKRKALrLf | 18 | 189 |
| rKKRrQRRrRKALrLf | 16 | 190 |

As mentioned above, in a particular embodiment of the present invention the transporter sequence and the inhibitory (poly-)peptide sequence may overlap. In other words, the N-terminus of the transporter sequence may overlap with the C-terminus of the inhibitory (poly-)peptide sequence or the C-terminus of the transporter sequence may overlap with the N-terminus of the inhibitory (poly-)peptide sequence. The latter embodiment is particularly preferred. Preferably, the transporter sequence overlaps by one, two or three amino acid residues with the inhibitory (poly-) peptide sequence. In such scenario a given transporter sequence may overlap with SEQ ID NO:1 or the respective variants thereof at position 1 (X1), position 1 and 2 (X1, X2), positions 1, 2 and 3 (X1, X2, X3).

SEQ ID NOs: 174, 175, 178, 179, 180, 181, 182, 183, 184, 188, 189 and 190 are good examples for JNK inhibitors according to the present invention, wherein transporter sequence and the inhibitory (poly-)peptide sequence overlap, e.g. rKKRrQRRrRPTTLNLf (SEQ ID NO: 174) is an overlap of SEQ ID NO: 46 (underlined) and SEQ ID NO: 11 (italics).

Certainly the JNK inhibitor according to the present invention may also be selected from JNK inhibitors, which are a variant of any one of the JNK inhibitors according to SEQ ID NOs: 171-190. Preferably, such variant shares at least 50%, more preferably at least 55%, more preferably at least 60%, more preferably at least 65%, more preferably at least 70%, more preferably at least 75%, more preferably at least 80%, more preferably at least 85%, more preferably at least 90%, most preferably at least 95% sequence identity with the sequence of SEQ ID NOs: 171-190, in particular with SEQ ID NO: 172,
with the proviso that with respect to the inhibitory (poly-)peptide sequence within said sequences of SEQ ID NOs: 171-190 (see for reference inhibitory (poly-)peptide sequence of SEQ ID NO: 1 and specific examples of SEQ ID NOs: 2-27)) such sequence sharing sequence identity a) maintains the L-arginine (R) residue on position 4 within the inhibitory (poly-)peptide sequence,
b) maintains the two L-leucine (L) residues at position 8 and 10 (positions 7 and 9 with regard to SEQ ID NOs: 25-27) within the inhibitory (poly-)peptide sequence,
c) exhibits at least one, at least two, at least three, at least four, at least five or six D-amino acid(s) at the respective positions corresponding to the amino acids selected from the group consisting of X1, X2, X3, X5, X7 and or X8 of SEQ ID NO: 1 and respective positions in SEQ ID NOs: 2-27, more preferably exhibits at least one, at least two, at least three or four D-amino acid(s) at the positions corresponding to the amino acids selected from the group consisting of X3, X5, X7 and X8 of SEQ ID NO: 1 and respective positions in SEQ ID NOs: 2-27, and
d) still inhibits JNK activity (i.e. is a JNK inhibitor as defined herein).

In view of said definition and for sake of clarity the residues which may not be changed in variants of JNK inhibitors comprising SEQ ID NOs: 171-190 (see a) and b) in the above definition) are underlined in table 3.

The non-identical amino acids in the variants of JNK inhibitors comprising SEQ ID NOs: 171-190 are preferably the result of conservative amino acid substitutions (see above). Certainly, the further possible substitutions mentioned above are also contemplated for variants of JNK inhibitors comprising SEQ ID NOs: 171-190. Likewise, the present invention certainly also contemplates variants of any one of the JNK inhibitors according to SEQ ID NOs: 171-190, which deviate from the original sequence not or not exclusively in the inhibitory (poly-)peptide sequence, but exhibits variant residues in the transporter sequence. For variants and fragments of transporter sequences see in particular respective disclosure above.

As mentioned previously, the transporter sequence and the JNK inhibitory (poly-)peptide sequence of the JNK inhibitors according to the present invention need not necessarily be directly joined to each other. They may also be spaced apart, e.g. by intermediate (poly-)peptide sequences. Preferred intermediate sequences separating the inhibitory (poly-)peptide sequences and other (functional) sequences such as transporter sequences consist of short peptide sequences less than 10 amino acids in length like a hexaamer, a pentamer, a tetramer, a tripeptide or even only a dipeptide or a single amino acid residue. Particularly preferred intermediate sequence are one, two or more copies of di-proline, di-glycine, di-arginine and/or di-lysine, all either in L-amino acid form only, or in D-amino acid form only, or with mixed D- and L-amino acids. Certainly, other known peptide spacer sequences may be employed as well.

A particularly preferred JNK inhibitor according to the present invention comprises SEQ ID NO: 8 (or a sequence sharing sequence identity with SEQ ID NO: 8 with the scope and limitations defined further above) and a transporter sequence. The transporter sequence is preferably selected from any one of SEQ ID Nos: 31-170 or variants thereof as defined herein, even more preferably from any one of SEQ ID NOs: 31-34 and 46-151. A particularly preferred embodiment of a JNK inhibitor according to the present invention is a JNK inhibitor comprising SEQ ID NO: 8 and SEQ ID NO: 46 (or sequences sharing respective sequence identity thereto within the scope and limitations defined further above). A preferred example is a JNK inhibitor comprising the sequence of SEQ ID NO: 172 or respective variants thereof varying in the transporter sequence and/or the inhibitory (poly-)peptide sequence as defined herein.

In a further aspect the present invention relates to a JNK inhibitor comprising
  a) an inhibitory (poly-)peptide comprising a sequence from the group of sequences consisting of RPTTLNLF (SEQ ID NO: 191), KRPTTLNLF (SEQ ID NO: 192), RRPTTLNLF and/or RPKRPTTLNLF (SEQ ID NO: 193), and
  b) a transporter sequence, preferably a transporter sequence selected from the transporter sequences disclosed in table 2 or variants/fragments thereof, even more preferably selected from SEQ ID NOs: 31-34 and 46-151 or respective variants or fragments thereof.

The transporter sequence and the inhibitory (poly-)peptide sequence may overlap. Preferred transporter sequences for said embodiment of the invention are particularly the transporter sequence of SEQ ID NO: 46, preferably joined (e.g. directly) to the N-Terminus of the inhibitory (poly-)peptide sequence.

A JNK inhibitor of the present invention may also be a JNK inhibitor comprising or consisting of the sequence GRKKRRQRRRPPKRPTTLNLFPQVPRSQD (SEQ ID NO: 194), or the sequence GRKKRRQRRRPTTLNLFPQVPRSQD (SEQ ID NO: 195).

In a further aspect the present invention relates to a (poly-)peptide comprising a transporter sequence selected from the group of sequences consisting of rKKRrQRr (SEQ ID NO: 148), rKKRrQRrK (SEQ ID NO: 149), and/or rKKRrQRrR (SEQ ID NO: 150).

As used herein, comprising a certain sequence or a certain SEQ ID NO: usually implies that (at least) one copy of said sequence is present, e.g. in the JNK inhibitor molecule. For example, one inhibitory (poly-)peptide sequence will usually suffice to achieve sufficient inhibition of JNK activity. However, the inventor certainly contemplate that the use of two or more copies of the respective sequence (e.g. two or more copies of an inhibitory (poly-)peptide sequence of different or same type and/or two or more copies of a transporter sequence of different or the same type) may also employed as long as the overall ability of the resulting molecule to inhibit JNK activity is not abolished (i.e. the respective molecule is still a JNK inhibitor as defined herein).

The inventive JNK inhibitors may be obtained or produced by methods well-known in the art, e.g. by chemical synthesis via solid-phase peptide synthesis using Fmoc (9-fluorenylmethyloxycarbonyl) strategy, i.e. by successive rounds of Fmoc deprotection and Fmoc-amino acid coupling cycles. A commercial service offering such peptide synthesis is provided by many companies, for example the company PolyPeptide (Straβbourg, France).

Antibodies

In a further aspect the present invention relates to the production of antibodies raised against the JNK inhibitors of the present invention, i.e. methods of producing antibodies recognizing the JNK inhibitors of the present invention. Methods for producing antibodies are extremely well known in the art.

Thus, the present invention relates also to a method of immunizing a non-human animal with a JNK inhibitor according to the present invention, the method comprising the following step:
  contacting (immunizing) a non-human animal suitable for antibody production,
    in particular a non-human mammal,
    more preferably an animal selected from goat and rodents such as mouse, rat, and rabbit
  with a JNK inhibitor of the present invention,
    more preferably with a JNK inhibitor comprising or consisting of a (poly-)peptide having a sequence selected from any one of SEQ ID NOs: 1-27.

As used herein "immunizing" is understood to be of non-therapeutic nature, since the JNK inhibitors according to the present invention are no pathogens (i.e. there is no need for therapy).

The present invention relates also to a method of producing an (polyclonal) antibody recognizing a JNK inhibitor according to the present invention, the method comprising the step of:
  Isolating from a non-human animal suitable for antibody production,
    in particular a non human mammal,
    more preferably an animal selected from goat and rodents such as mouse, rat, and rabbit,
  which has been contacted (immunized) previously with a JNK inhibitor of the present invention,
    more preferably with a JNK inhibitor comprising or consisting of a (poly-)peptide having a sequence selected from any one of SEQ ID NOs: 1-27,
  an (polyclonal) antibody recognizing said JNK inhibitor.

The present invention relates also to a method of isolating a cell producing an antibody recognizing a JNK inhibitor according to the present invention, the method comprising the step of:
  Isolating from a non-human animal suitable for antibody production,
    in particular a non human mammal,
    more preferably an animal selected from goat and rodents such as mouse, rat, and rabbit,
  which has been contacted (immunized) previously with a JNK inhibitor of the present invention,
    more preferably with a JNK inhibitor comprising or consisting of a (poly-)peptide
    having a sequence selected from any one of SEQ ID NOs: 1-27,
  a cell producing said antibody recognizing said JNK inhibitor, and
  optionally immortalizing said cell.

The present invention relates also to a method of producing a (monoclonal) antibody recognizing a JNK inhibitor according to the present invention, the method comprising the step of:
  Isolating an antibody recognizing a JNK inhibitor of the present invention, more preferably recognizing a JNK inhibitor consisting of a (poly-)peptide having a sequence selected from any one of SEQ ID NOs: 1-27,
from the cell culture supernatant of a cell producing said antibody, the cell being optionally immortalized.

A person skilled in the art will understand, that the method of immunizing a non-human animal and the method of producing an (polyclonal) antibody as disclosed herein may be carried out consecutively. Similarly, the method of immunizing a non-human animal, the method of isolating a cell producing an antibody and the method of producing an (monoclonal) antibody may be combined.

In a further aspect the present invention relates to an antibody producible (and/or produced) with the methods according to the present invention for producing a polyclonal or monoclonal antibody, wherein the antibody recognizes at least one (poly-)peptide comprising or consisting of a sequence selected from any one of SEQ ID NOs: 1-27, but does preferably not (or at least to lesser extent, e.g. at least by one order of magnitude) recognize the essentially same (poly-)peptide with L-amino acids in place of the D-amino acids in the respective sequence stretch of SEQ ID NO: 1-27. Preferably, such antibody does recognize a JNK inhibitor of the present invention, but does (or at least to lesser extent, e.g. at least by one order of magnitude) not recognize a (poly-)peptide comprising the sequence RPKRPTTLNLF (SEQ ID NO: 193)). A particularly preferred antibody (monoclonal or polyclonal) does recognize a JNK inhibitor comprising the sequence of SEQ ID NO: 8 (for example a JNK inhibitor comprising the sequence of SEQ ID NO: 172), but does not (or at least to lesser extent, e.g. at least by one order of magnitude) recognize a (poly-)peptide comprising the very same sequence with L-amino acids in place of the D-amino acids. Particularly preferred are such polyclonal or monoclonal antibodies recognizing a (poly-)peptide comprising SEQ ID NO: 172, but not recognizing (or at least recognizing to lesser extent, e.g. at least by one order of magnitude) a (poly-)peptide comprising the sequence RKKRRQRRRRP-KRPATLNLF (SEQ ID NO: 199).

The present invention also relates to a cell isolated according to the above specified method of isolating a cell producing an antibody recognizing a JNK inhibitor according to the present invention, wherein the cell produces an antibody which preferably recognizes at least one (poly-)peptide selected from any one of SEQ ID NOs: 1-27, but does not recognize the essentially same (poly-)peptide with L-amino acids in place of the D-amino acids in the sequence corresponding to SEQ ID NO: 1, (e.g. does recognize a (poly-)peptide comprising the sequence RPkRPaTLNLf (SEQ ID NO: 8), but does not recognize (or at least to lesser extent, e.g. at least by one order of magnitude) a (poly-)peptide comprising the sequence RPKRPTTLNLF (SEQ ID NO: 193).

The present invention also contemplates generating antibodies against the specific transporter sequences, thereby allowing to identify for example JNK inhibitors as disclosed in table 3. Consequently, all aspects (monoclonal or polyclonal antibodies; methods of generating the same, cells producing the same etc.) discussed above for antibodies recognizing a JNK inhibitor of the present invention (in particular at least one (poly-)peptide comprising or consisting of a sequence selected from any one of SEQ ID NOs: 1-27) may also be applied in the context of (poly-)peptide comprising or consisting of a sequence selected from any one of SEQ ID NOs: 31-34 and 46-151. Certainly, the reference sequence which must not be recognized (or at least to lesser extent, e.g. by at least one order of magnitude) is in this scenario again the very same sequence however with L-amino acids in place of the D-amino acids in the respective transporter sequence stretch.

Methods for testing (monoclonal and/or polyclonal) antibodies for their binding affinities are well known in the art. One possibility among other is to characterize the binding affinity of an antibody by means of a sandwich ELISA by using the target peptide as well as negative controls (e.g. the same peptide with L-amino acids only). The ELISA limit can—without being limited thereto—be calculated on blank replicates as follows:

ELISA limit=average(negative control)+(3×standard deviation of negative control).

If the sample value is less or equal to the ELISA limit the tested antibody may be considered to have no affinity to the target peptide. If the sample value exceeds the ELISA limit the tested antibody may be considered to exhibit affinity to the target peptide. Moreover, the higher the sample value, the stronger is the affinity of the tested antibody for the target.

A commercial service offering production of monoclonal or polyclonal antibodies is for example Eurogentec (Seraing, Belgium).

All references cited herein are herewith incorporated by reference.

EXAMPLES

In the following, particular examples illustrating various embodiments and aspects of the invention are presented. However, the present invention shall not to be limited in scope by the specific embodiments described herein. Indeed, various modifications of the invention in addition to those described herein will become readily apparent to those skilled in the art from the foregoing description, accompanying figures and the examples below. All such modifications fall within the scope of the appended claims.

Example 1

Synthesis of JNK Inhibitor SEQ ID NO: 172

As illustrative example, synthesis of the JNK inhibitor with SEQ ID NO: 172 is set out below. A person skilled in the art will know that said synthesis may also be used for and easily adapted to the synthesis of any other JNK inhibitor according to the present invention.

The JNK inhibitor with SEQ ID NO: 172 was manufactured by solid-phase peptide synthesis using the Fmoc (9-fluorenylmethyloxycarbonyl) strategy. The linker between the peptide and the resin was the Rink amide linker (p-[Fmoc-2,3-dimethoxybenzyl]-phenoxyacetic acid). The peptide was synthesized by successive Fmoc deprotection and Fmoc-amino acid coupling cycles. At the end of the synthesis, the completed peptide was cleaved by trifluoroacetic acid (TFA) directly to yield the crude C-terminal amide, which was then purified by preparative reverse phase HPLC. The purified fractions were pooled in a homogeneous batch that is treated by ion exchange chromatography to obtain its acetate salt. The peptide was then freeze-dried.

1.1 Solid Phase Synthesis of the Peptide

Except when noted, the manufacturing took place at room temperature (22° C.±7° C.) in an air-filtered environment. The scale of synthesis was 0.7 mmoles of the starting amino acid on the resin, for an expected yield of about 1 g of purified peptide. Synthesis was performed manually in a 30-50 mL reactor equipped with a fritted disk with mechanical stirring and/or nitrogen bubbling.

1.2 Preparation of the Resin

The p-methylbenzhydrylamide resin (MBNA-resin) was first washed with dichloromethane/dimethylformamide/diisoproplyethylamine under nitrogen. The washed resin was then coupled to the Rink amide linker (p-[Fmox-2,4-dimethoxybenzyl]-phenoxyacetic acid) in PyBOB(benzotriazole-1-yl-oxy-tris-pyrrolidi no-phosphonium hexafluorophosphate)/diisopropyl-ethylamine/1-hydroxybenzotriazole to yield Fmoc-Rink amide-MBNA resin.

1.3 Coupling of Amino Acids

Amino acids were coupled to the resin using the following cycle:

The Fmoc-Rink amide-MBHA resin was deprotected by washing it in 35% (v/v) piperidine/dimethylformamide, followed by di methylformamide. The deprotection reaction took approximately 16 minutes. Fmoc-protected amino acids (e.g., 2 eq of amino acid and HOBt (1-hydroxybenzotriazole) in dimethylformamide/dichloromethane (50/50) were added to the resin followed by addition of 2 eq of the coupling agent diisopropylcarbodiimide (DIC). The coupling reaction took from one hour to overnight depending upon the respective amino acid being added. Volumes were calculated on a basis of 0.5 mL/00 mg of peptide-resin and adjusted after each cycle. After coupling, the resin was washed 3 times with DMF. Completeness of coupling was tested by the ninhydrin test (or Kaiser test 1) on primary amines and the chloranyl test 2 on secondary amines. On some occasions, the chloranyl test may be associated with a ninhydrin test as a security control. In case the coupling test indicated incompleteness of reaction, coupling was repeated with a lower excess (0.5-1 eq) of amino acid, PYBOP, HOBT in dimethylformamide/dichloromethane and diisopropylethylamine. Functionality of the resin was measured and generally 0.6-0.2 meq/g, depending on the original loading of the resin. After the last amino acid has been coupled, the peptide-resin was deprotected as usual and then washed 5 times with DCM before drying in an oven under vacuum at 30° C. After the peptide-resin had dried, the yield of the solid-phase synthesis was calculated as the ratio of the weight increase of the peptide resin compared to the theoretical weight increase calculated from the initial loading of the resin. The yield may be close to 100%.

1.4 Cleavage and Deprotection

The peptide was cleaved from the resin in a mixture of trifluoroacetic acid/1,2-ethanedthiol/thioanisole/water/phenol (88/2.2/4.4/4.4/7 v/v), also called TFA/K reagent, for 4 hours at room temperature. The reaction volume was 1 mL/100 mg of peptide resin. During addition of the resin to the reagent, the mixture temperature was regulated to stay below 30° C.

1.5 Extraction of the Peptide from the Resin:

The peptide was extracted from the resin by filtration through a fritted disc. After concentration on a rotavapor to ⅓ of its volume, the peptide was precipitated by cold t-butyl methyl ether and filtered. The crude peptide was then dried under vacuum at 30° C.

1.6 Preparative HPLC Purification:

The crude peptide was then purified by reverse-phase HPLC to a purity of ≥95%. The purified fractions were concentrated on a rotavaporator and freeze-dried.

1.7 Ion Exchange Chromatography

The concentrated freeze-dried pools of purified peptide with the sequence of SEQ ID NO: 172 was dissolved in water and purified by ion exchange chromatography on Dowex acetate, 50-100 mesh resin.

The required starting reagents for the synthesis were:

| | CAS Registry Number | Chemical Name | Molecular Weight |
|---|---|---|---|
| Fmoc-Rink amide linker | 145069-56-3 | p-[Fmoc-2,4-dimethoxybenzyl]-phenoxyacetic acid | 539.6 |
| Fmoc-D-Ala-OH, $H_2O$ | 79990-15-1 | N-alpha-Fmoc-D-alanine | 311.3 |
| Fmoc-Arg(Pbf)-OH | 154445-77-9 | N-alpha-Fmoc-N [2,2,4,6,7-pentamethyldihydrobenzofuran-5-sulfonyl]-arginine | 648.8 |
| Fmoc-D-Arg(Pbf)-OH | 187618-60-6 | N-alpha-Fmoc-N [2,2,4,6,7-pentamethyldihydrobenzofuran-5-sulfonyl]-D-arginine | 648.8 |
| Fmoc-Asn(Trt)-OH | 132388-59-1 | N-alpha-Fmoc-N- -trityl-asparagine | 596.7 |
| Fmoc-Gln(Trt)-OH | 132327-80-1 | N-alpha-Fmoc-N- -trityl-glutamine | 610.7 |
| Fmoc-Leu-OH | 35661-60-0 | N-alpha-Fmoc-leucine | 353.4 |
| Fmoc-Lys(Boc)-OH | 71989-26-9 | N-alpha-Fmoc-N-Boc-lysine | 468.5 |
| Fmoc-D-Lys(Boc)-OH | 143824-78-6 | N-alpha-Fmoc-N-Boc-D-lysine | 468.5 |
| Fmoc-D-Phe-OH | 86123-10-6 | N-alpha-Fmoc-D-phenylalanine | 387.4 |
| Fmoc-Pro-OH | 71989-31-6 | N-alpha-Fmoc-proline | 337.4 |
| Fmoc-Thr(tBu)-OH | 71989-35-0 | N-alpha-Fmoc-O-t-butyl-threonine | 397.5 |

Other JNK inhibitors of the present invention may prepared in similar manner.

Example 2

Inhibitory Efficacy of Selected JNK Inhibitors According to the Present Invention In the following the standard operating procedure will be set forth describing how the Inhibitory efficacy of JNK inhibitors according to the present invention was measured. The method allows to measure in vitro, in a non radioactive standardized assay, the ability of a candidate compound to decrease the phosphorylation of the c-Jun specific substrate by JNK. Moreover, it will be illustrated how to determine the inhibitory effect (IC50) and the Ki of a chosen compound for JNK. The method is suitable to verify whether a candidate compound does or does not inhibit JNK activity. and a person skilled in the art will certainly understand how to adapt the below methods for his specific purposes and needs.

2.1 Material

AlphaScreen Reagent and Plate:
- His-JNK1 (ref 14-327, Upstate, 10 μg in 100 μl: concentration: 2.2 μM) 5 nM final
- His-JNK2 (ref 14-329, Upstate, 10 μg in 100 μl: concentration: 2 μM) 5 nM final
- His-JNK3 (ref 14-501, Upstate, 10 μg in 100 μl: concentration: 1.88 μM) 5 nM final
- Anti-Phospho-cJun (ref 06-828, Upstate, lot DAM1503356, concentration: 44.5 μM) 10 nM final
- Biotin-cJun (29-67):
  sequence: Biotin-SNPKILKQSMTLNLADPVGSLK-PHLRAKNSDLLTSPDVG (SEQ ID NO: 198), lot 100509 (mw 4382.11, P 99.28%) dissolved in $H_2O$, concentration: 10 mM) 30 nM final
- ATP (ref AS001A, Invitrogen, lot 50860B, concentration 100 mM)) 5 μM final
- SAD beads (ref 6760617M, PerkinElmer, lot 540-460-A, concentration 5 mg/ml) 20 μg/ml final AprotA beads (ref 6760617M, PerkinElmer, lot 540-460-A, concentration 5 mg/ml) 20 µg/ml final Optiplate 384 well white plate (ref 6007299, PerkinElmer, lot 654280/2008)

96 well plate for peptide dilution (ref 82.1581, Sarstedt)

TopSeals-A (ref 6005185, Perkin Elmer, Lot 65673)

Bioluminescent energy transfer reading

The bioluminescent energy transfer was read on the Fusion Alpha Plate reader (Perkin Elmer).

Pipette:

An electronic EDP3 pipette 20-300 (Ref 17007243; Rainin) was used to fill in the plate with the Enzme-Antibody mix, the Subtrate-ATP mix and the Beads.

A PIPETMAN® Ultra multichannel 8X20 (Ref 21040; Gilson) was used to fill in the plate with the inhibitory compounds.

Buffer and Solutions

Kinase Buffer: 20 mM Tris-base pH 7.4, 10 mM $MgCl_2$, 1 mM DTT, 100 µM $Na_3VO_4$, 0.01% Tween, (1% DMSO)

Stop Buffer: 20 mM Tris-base pH 7.4, 200 mM NaCl, 80 mM EDTA-K (pH de 8 with KOH instead of NaOH), 0.3% BSA JNK dilution Kinase buffer: 50 mM Tris-base pH 7.4, 150 mM NaCl, 0.1 mM EGTA, 0.03% Brij-35, 270 mM sucrose, 0.1% β-mercaptoethanol.

2.2 Method

To assess inhibitory effect of the peptides, a standard AlphaScreen assay (see for example Guenat et al. J Biomol Screen, 2006; 11: pages 1015-1026) was performed. The different components were prepared and subsequently mixed as indicated. The plates were sealed and incubated as following:

| | | |
|---|---|---|
| 5 µl | JNIK + Antibody | |
| 5 µl | TP kinase +/− inhibiteur | Pre-incubation 30 min |
| 5 µl | Biotin-cJun + ATP | Incubation 60 min at 24° C. |
| 10 µl | Beads SAD + A protA | Incubation 60 min in the dark at 24° C. |

To avoid contamination, the mixes were added with the pipette in different corner of the well. After the filling in of the plate with each mix, the plate was tapped (Keep one side fix and let the opposite side tap the table) to let the mix go down the walls of the wells.

The bioluminescent energy transfer was read on the Fusion Alpha Plate reader (Perkin Elmer).

All compounds should at least be tested in triplicate in 3 independent experiments for each isoform of JNK. Possibly concentrations of the compounds to be tested were 0, 0.03 nM, 0.1 nM, 0.3 nM, 1 nM, 3 nM, 10 nM, 30 nM, 100 nM, 300 nM, 1 µM, 3 µM, 10 µM, 30 µM, and 100 µM. Controls were samples either without JNK or without substrate (c-Jun).

Mix Preparation

JNK1, JNK2 and JNK3 5 nM

Biotin-cJun 30 nM

ATP 5 µM; Anti phospho-cJun (S63) 10 nM

Bille SAD/AprotA 20 µg/ml

Antibody [final]=10 nM (anti Phospho cJun (S63))

Detection part: [Mix] X5 (5 µl in final volume of 25 µl)

[Stock]=44.5 µM (ref 06-828, Upstate, Lot DAM1503356)

10 nM→50 nM in Kinase Buffer

JNK1, JNK2 and JNK3 [final]=5 nM

Reaction part: [Mix] X3 (5 µl in final volume of 15 µl)

[Stock]=2.2 µM for JNK1 (ref 14-327, Upstate, lot D7KN022CU)

2.0 µM for JNK2 (ref 14-329, Upstate, lot 33221CU)

1.88 µM for JNK3 (ref 14-501, Upstate, lot D7CN041CU)

5 nM→15 nM in Antibody Buffer

Inhibitor:

Reaction part: [Mix] X3 (5 µl in final volume of 15 µl)

| [Stock] = 10 mM | | |
|---|---|---|
| 100 µM | → | 300 µM in Kinase Buffer |
| 30 µM | → | 90 µM in Kinase Buffer |
| 10 µM | → | 30 µM in Kinase Buffer |
| ... | | |
| 0.03 nM | → | 0.09 nM in Kinase Buffer |
| And 0 nM | → | Kinase Buffer |

Two series of 10 times serial dilutions were performed in a 96 well plate, one beginning with 300 µM to 0 nM, the second with 90 µM to 0.03 nM. The peptides are added in the 384 plates with an 8 channels multipipette (ref F14401, Gilson, 8X20).

ATP [final]=5 µM

Reaction part: [Mix] X3 (5 µl in final volume of 15 µl)

[Stock]=100 mM (ref AS001A, Invitrogen, lot 50860B)

5 µM→15 µM in Kinase Buffer

Biotin c-Jun [final]=30 nM

Reaction part: [Mix] X3 (5 µl in final volume of 15 µl)

[Stock]=10 mM 30 nM→30 nM in ATP Buffer

Beads SAD/A ProtA [final]=20 µg/ml (Light sensitive)

Detection part: [Mix]×2.5 (10 µl in final volume of 25 µl)

[Stock]=5 mg/ml→20 µg/ml 50 µg/ml in STOP Buffer

Mix in the dark room (green Light) or in the darkness.

Analysis of the IC50 Curves:

The analysis was performed by the GraphPad Prism4 software with the following equation:

Sigmoidal dose-response (No constraint).

$$Y = \text{Bottom} + (\text{Top} - \text{Bottom})/(1 + 10^{((\text{Log } EC50 - X))})$$

The outliers data were avoided using Grugg's test.

Comparison of the IC50:

The analysis was performed by the GraphPad Prism4 software with the following test: One way ANOVA test followed by a Tukey's Multiple Comparison Test. P<0.05 was considerate as significant.

The Km of the ATP for JNK and the Km of biotin-cJun specific peptide were determined in the report AlphaScreen standardization assay The mathematical relation between Ki and IC50 (Ki=IC50/(1+((Substrate)/Km of the substrate)) may be used to calculate the Ki values.

Example 3

Internalization Experiments and Analysis 3.1 Materials and Methods for Uptake Experiments a) Cell Line:

The cell line used for this experiment was HL-60 (Ref CCL-240, ATCC, Lot 116523)

b) Culture Medium and Plates

RPMI (Ref 21875-091, Invitrogen, Lot 8296) or DMEM (Ref 41965, Invitrogen, Lot 13481) complemented on May 5, 2008 with:

10% FBS (Ref A64906-0098, PAA, Lot A15-151): decomplemented at 56° C., 30 min, on Apr. 4, 2008.

1 mM Sodium Pyruvate (Ref 58636, Sigma, Lot 56K2386)
Penicillin (100 unit/ml)/Streptomycin (100 µg/ml) (Ref P4333, Sigma, Lot 106K2321)
PBS 10× (Ref 70011, Invitrogen, Lot 8277): diluted to 1× with sterile $H_2O$
Trypsine-0.05% EDTA (Ref L-11660, PAA, Lot L66007-1194)
6 well culture plates (Ref 140675, Nunc, Lot 102613)
24 well culture plates (Ref 142475, Nunc, Lot 095849)
96 well culture plates (Ref 167008, Nunc, Lot 083310)
96 well plates for protein dosing (Ref 82.1581, Sarstedt)
96 well plates for fluorescence measurement (Ref 6005279, Perkin Elmer)

c) Solutions
Poly-D-lysine coating solution (Sigma P9011 Lot 095K5104): 25 µg/ml final diluted in PBS 1×
Acidic wash buffer: 0.2M Glycin, 0.15M NaCl, pH 3.0
Ripa lysis buffer: 10 mM $NaH_2PO_4$ pH 7.2, 150 mM NaCl, 1% Triton X-100, 1 mM EDTA pH 8.0, 200 µM $Na_3VO_2$, 0.1% SDS, 1× protease inhibitor cocktail (Ref 11873580001, Roche, Lot 13732700)

d) Microscopy and Fluorescence Plate Reader
Cells were observed and counted using an inverted microscope (Axiovert 40 CFL; Zeiss; 20×).
The fluorescence was read with the Fusion Alpha Plate reader (Perkin Elmer).

e) Method
FITC marked peptide internalization was studied on suspension cells. Cells were plated into poly-DL-lysine coated dishes at a concentration of $1×10^6$ cells/ml. Plates were then incubated for 24 h at 37° C., 5% $CO_2$ and 100% relative humidity prior to the addition of a known concentration of peptide. After peptide addition, the cells were incubated 30 min, 1, 6 or 24 h at 37° C., 5% $CO_2$ and 100% relative humidity. Cells were then washed twice with an acidic buffer (Glycin 0.2 M, NaCl 0.15 M, pH 3.0) in order to remove the cell-surface adsorbed peptide (see Kameyama et al., (2007), *Biopolymers*, 88, 98-107). The acidic buffer was used as peptides rich in basic amino acids adsorb strongly on the cell surfaces, which often results in overestimation of internalized peptide. The cell wash using an acidic buffer was thus employed to remove the cell-surface adsorbed peptides. The acid wash was carried out in determining cellular uptake of Fab/cell-permeating peptide conjugates, followed by two PBS washes. Cells were broken by the addition of the RIPA lysis buffer. The relative amount of internalized peptide was then determined by fluorescence after background subtraction and protein content normalization.
The steps are thus: 1. Cell culture
  2. Acidic wash and cellular extracts
  3. Analysis of peptide internalization with a fluorescence plate reader f) Cell Culture and Peptide Treatment
The 6 well culture plates are coated with 3 ml of Poly-D-Lys (Sigma P9011; 25 µg/ml in PBS), the 24 well plates with 600 µl and the 96 well plates with 125 µl and incubated for 4 h at 37° C., $CO_2$ 5% and 100% relative humidity.

After 4 hours the dishes were washed twice with 3.5 ml PBS, 700 µl or 150 µl PBS for the 6, 24 or 96 well plates, respectively.

The cells were plated into the dishes in 2.4 ml medium (RPMI) at plating densities of 1,000,000 cells/ml for suspension cells. After inoculation, the plates were incubated at 37° C., 5% $CO_2$ and 100% relative humidity for 24 hours prior to the addition of the peptide. Adherent cells should be at a density of 90-95% the day of treatment and were plated in DMEM:

| well | Surface of culture (cm²) | Medium | Nb adherent cells | Nb suspension cells |
| --- | --- | --- | --- | --- |
| 96 well | 0.3 | 100-200 µl | 8'000-30'000 | 100'000 |
| 24 well | 2 | 500-1000 µl | 100'000-200'000 | 500'000-1'000'000 |
| 35 mm (P35)/6 well | 10 | 2.4 ml | 250'000-2'100'000 | 2'400'000 |
| 60 mm (P60) | 20 | 3.5 ml | $15*10^5$ | 1'000'000/ml |
| 10 cm (P100) | 60 | 10 ml | $15-60*10^5$ | |

The cells were treated with the desired concentration of FITC labeled peptide (stock solution at a concentration of 10 mM in $H_2O$).

Following peptide addition, the cells were incubated 0 to 24 hours (e.g. 30 min, 1, 6 or 24 hours) at 37° C., $CO_2$ 5% and 100% relative humidity.

Acidic Wash and Cellular Extracts:
The extracts were cooled on ice.
Suspension cells (or cells, which don attach well to the dish):
Transfer the cells in <<Falcon 15 ml>>. To recover the maximum of cells, wash the dish with 1 ml of PBS.
Harvest the cells 2 min at 2400 rpm max.
Suspend the cells in 1 ml cold PBS.
Transfer the cells into a coated "Eppendorf tube" (coated with 1 ml of poly D-Lys for 4 hours and washed twice with 1 ml PBS).
Wash three times with 1 ml of cold acidic wash buffer and centrifuge 2 min at 2400 rpm max.
Beware of the spreading of the cells in the "eppendorf".
Wash twice with 1 ml cold PBS to neutralize.
Add 50 µl of lysis RIPA Buffer.
Incubate 30 min-1 h on ice with agitation.
Adherent cells:
Wash three times with 3 ml, 1 ml or 200 µl (for 6, 24 or 96 well plates, respectively) of cold acidic wash buffer. Beware of the cells who detach from the dish.
Wash twice with 1 ml cold PBS (for 6, 24 or 96 well plates, respectively) to neutralize.
Add 50 µl of lysis RIPA buffer.
Incubate 30 min-1 h on ice with agitation.
Scrap the cells with a cold scrapper. The 24 and 96 well plates were directly centrifuged at 4000 rpm at 4° for 15 min to remove the cellular debris. Then the supernatants (100 or 50 ml respectively for the 24 or 96 well plates) were directly transferred in a dark 96 well plated. The plates were read by a fluorescence plate reader (Fusion Alpha, Perkin Elmer).
Transfer the lysate in a coated "eppendorf" (coated with 1 ml of poly D-Lys for 4 hours and wash twice with 1 ml PBS).
The lysed cells were then centrifuged 30 min at 10000 g at 4° C. to remove the cellular debris. Remove the supernatant and store it at −80° C. in a coated "Eppendorf tube" (coated with 1 ml of poly D-Lys for 4 hours and washed twice with 1 ml PBS).

Analysis of Peptide Internalization with a Fluorescence Plate Reader:

The content of each protein extract was determined by a standard BCA assay (Kit N° 23225, Pierce), following the instructions of the manufacturer.

The relative fluorescence of each sample is determined after reading 10 µl of each sample in a fluorescence plate reader (Fusion Alpha, Perkin Elmer), background subtraction and normalization by protein concentration.

3.2 Uptake Experiments

The time dependant internalization (uptake) of FITC-labeled TAT derived transporter constructs into cells of the HL-60 cell line was carried out as described above using sequences transporter peptides of SEQ ID NOs: 52-96, 43, and 45-47. These sequences are listed below in Table 4.

TABLE 4

Transporter sequence tested in uptake experiments

| SEQ ID NO: | peptide No: abbreviation in FIG. 6 | | | | | | | | | | |
|---|---|---|---|---|---|---|---|---|---|---|---|
| 46 | r3-L-TAT | H2N | dR | K | K | R | dR | Q | R | R | dR | CONH2 |
| 52 | 1 | H2N | dR | A | K | R | dR | Q | R | R | dR | CONH2 |
| 53 | 2 | H2N | dR | K | A | R | dR | Q | R | R | dR | CONH2 |
| 54 | 3 | H2N | dR | K | K | A | dR | Q | R | R | dR | CONH2 |
| 55 | 4 | H2N | dR | K | K | R | dR | A | R | R | dR | CONH2 |
| 56 | 5 | H2N | dR | K | K | R | dR | Q | A | R | dR | CONH2 |
| 57 | 6 | H2N | dR | K | K | R | dR | Q | R | A | dR | CONH2 |
| 58 | 7 | H2N | dR | D | K | R | dR | Q | R | R | dR | CONH2 |
| 59 | 8 | H2N | dR | K | D | R | dR | Q | R | R | dR | CONH2 |
| 60 | 9 | H2N | dR | K | K | D | dR | Q | R | R | dR | CONH2 |
| 61 | 10 | H2N | dR | K | K | R | dR | D | R | R | dR | CONH2 |
| 62 | 11 | H2N | dR | K | K | R | dR | Q | D | R | dR | CONH2 |
| 63 | 12 | H2N | dR | K | K | R | dR | Q | R | D | dR | CONH2 |
| 64 | 13 | H2N | dR | E | K | R | dR | Q | R | R | dR | CONH2 |
| 65 | 14 | H2N | dR | K | E | R | dR | Q | R | R | dR | CONH2 |
| 66 | 15 | H2N | dR | K | K | E | dR | Q | R | R | dR | CONH2 |
| 67 | 16 | H2N | dR | K | K | R | dR | E | R | R | dR | CONH2 |
| 68 | 17 | H2N | dR | K | K | R | dR | Q | E | R | dR | CONH2 |
| 69 | 18 | H2N | dR | K | K | R | dR | Q | R | E | dR | CONH2 |
| 70 | 19 | H2N | dR | F | K | R | dR | Q | R | R | dR | CONH2 |
| 71 | 20 | H2N | dR | K | F | R | dR | Q | R | R | dR | CONH2 |
| 72 | 21 | H2N | dR | K | K | F | dR | Q | R | R | dR | CONH2 |
| 73 | 22 | H2N | dR | K | K | R | dR | F | R | R | dR | CONH2 |
| 74 | 23 | H2N | dR | K | K | R | dR | Q | F | R | dR | CONH2 |
| 75 | 24 | H2N | dR | K | K | R | dR | Q | R | F | dR | CONH2 |
| 76 | 25 | H2N | dR | R | K | R | dR | Q | R | R | dR | CONH2 |
| 77 | 26 | H2N | dR | K | R | R | dR | Q | R | R | dR | CONH2 |
| 78 | 27 | H2N | dR | K | K | K | dR | Q | R | R | dR | CONH2 |
| 79 | 28 | H2N | dR | K | K | R | dR | R | R | R | dR | CONH2 |
| 80 | 29 | H2N | dR | K | K | R | dR | Q | K | R | dR | CONH2 |
| 81 | 30 | H2N | dR | K | K | R | dR | Q | R | K | dR | CONH2 |
| 82 | 31 | H2N | dR | H | K | R | dR | Q | R | R | dR | CONH2 |
| 83 | 32 | H2N | dR | K | H | R | dR | Q | R | R | dR | CONH2 |
| 84 | 33 | H2N | dR | K | K | H | dR | Q | R | R | dR | CONH2 |
| 85 | 34 | H2N | dR | K | K | R | dR | H | R | R | dR | CONH2 |
| 86 | 35 | H2N | dR | K | K | R | dR | Q | H | R | dR | CONH2 |
| 87 | 36 | H2N | dR | K | K | R | dR | Q | R | H | dR | CONH2 |
| 88 | 37 | H2N | dR | I | K | R | dR | Q | R | R | dR | CONH2 |
| 89 | 38 | H2N | dR | K | I | R | dR | Q | R | R | dR | CONH2 |
| 90 | 39 | H2N | dR | K | K | I | dR | Q | R | R | dR | CONH2 |
| 91 | 40 | H2N | dR | K | K | R | dR | I | R | R | dR | CONH2 |
| 92 | 41 | H2N | dR | K | K | R | dR | Q | I | R | dR | CONH2 |
| 93 | 42 | H2N | dR | K | K | R | dR | Q | R | I | dR | CONH2 |
| 94 | 43 | H2N | dR | L | K | R | dR | Q | R | R | dR | CONH2 |
| 45 | 44 (D-TAT) | H2N | dR | dR | dR | dQ | dR | dR | dK | dK | dR | CONH2 |
| 47 | 45 (r3-L-TATi) | H2N | dR | R | R | Q | dR | R | K | K | dR | CONH2 |
| 46 | 46 (r3-L-TAT) | H2N | dR | K | K | R | dR | Q | R | R | dR | CONH2 |
| 43 | 47 (L-TAT) | H2N | R | K | K | R | R | Q | R | R | R | CONH2 |
| 99 | 48 | H2N | dR | K | K | R | dR | Q | R | L | dR | CONH2 |
| 100 | 49 | H2N | dR | M | K | R | dR | Q | R | R | dR | CONH2 |
| 101 | 50 | H2N | dR | K | M | R | dR | Q | R | R | dR | CONH2 |
| 102 | 51 | H2N | dR | K | K | M | dR | Q | R | R | dR | CONH2 |
| 103 | 52 | H2N | dR | K | K | R | dR | M | R | R | dR | CONH2 |
| 104 | 53 | H2N | dR | K | K | R | dR | Q | M | R | dR | CONH2 |
| 105 | 54 | H2N | dR | K | K | R | dR | Q | R | M | dR | CONH2 |
| 106 | 55 | H2N | dR | N | K | R | dR | Q | R | R | dR | CONH2 |
| 107 | 56 | H2N | dR | K | N | R | dR | Q | R | R | dR | CONH2 |
| 108 | 57 | H2N | dR | K | K | N | dR | Q | R | R | dR | CONH2 |
| 109 | 58 | H2N | dR | K | K | R | dR | N | R | R | dR | CONH2 |
| 110 | 59 | H2N | dR | K | K | R | dR | Q | N | R | dR | CONH2 |
| 111 | 60 | H2N | dR | K | K | R | dR | Q | R | N | dR | CONH2 |
| 112 | 61 | H2N | dR | Q | K | R | dR | Q | R | R | dR | CONH2 |
| 113 | 62 | H2N | dR | K | Q | R | dR | Q | R | R | dR | CONH2 |

TABLE 4-continued

Transporter sequence tested in uptake experiments

| SEQ ID NO: | peptide No: abbreviation in FIG. 6 | | | | | | | | | | |
|---|---|---|---|---|---|---|---|---|---|---|---|
| 114 | 63 | H2N | dR | K | K | Q | dR | Q | R | R | dR | CONH2 |
| 115 | 64 | H2N | dR | K | K | R | dR | K | R | R | dR | CONH2 |
| 116 | 65 | H2N | dR | K | K | R | dR | Q | Q | R | dR | CONH2 |
| 117 | 66 | H2N | dR | K | K | R | dR | Q | R | Q | dR | CONH2 |
| 118 | 67 | H2N | dR | S | K | R | dR | Q | R | R | dR | CONH2 |
| 119 | 68 | H2N | dR | K | S | R | dR | Q | R | R | dR | CONH2 |
| 120 | 69 | H2N | dR | K | K | S | dR | Q | R | R | dR | CONH2 |
| 121 | 70 | H2N | dR | K | K | R | dR | S | R | R | dR | CONH2 |
| 122 | 71 | H2N | dR | K | K | R | dR | Q | S | R | dR | CONH2 |
| 123 | 72 | H2N | dR | K | K | R | dR | Q | R | S | dR | CONH2 |
| 124 | 73 | H2N | dR | T | K | R | dR | Q | R | R | dR | CONH2 |
| 125 | 74 | H2N | dR | K | T | R | dR | Q | R | R | dR | CONH2 |
| 126 | 75 | H2N | dR | K | K | T | dR | Q | R | R | dR | CONH2 |
| 127 | 76 | H2N | dR | K | K | R | dR | T | R | R | dR | CONH2 |
| 128 | 77 | H2N | dR | K | K | R | dR | Q | T | R | dR | CONH2 |
| 129 | 78 | H2N | dR | K | K | R | dR | Q | R | T | dR | CONH2 |
| 130 | 79 | H2N | dR | V | K | R | dR | Q | R | R | dR | CONH2 |
| 131 | 80 | H2N | dR | K | V | R | dR | Q | R | R | dR | CONH2 |
| 132 | 81 | H2N | dR | K | K | V | dR | Q | R | R | dR | CONH2 |
| 133 | 82 | H2N | dR | K | K | R | dR | V | R | R | dR | CONH2 |
| 134 | 83 | H2N | dR | K | K | R | dR | Q | V | R | dR | CONH2 |
| 135 | 84 | H2N | dR | K | K | R | dR | Q | R | V | dR | CONH2 |
| 136 | 85 | H2N | dR | W | K | R | dR | Q | R | R | dR | CONH2 |
| 137 | 86 | H2N | dR | K | W | R | dR | Q | R | R | dR | CONH2 |
| 138 | 87 | H2N | dR | K | K | W | dR | Q | R | R | dR | CONH2 |
| 139 | 88 | H2N | dR | K | K | R | dR | W | R | R | dR | CONH2 |
| 140 | 89 | H2N | dR | K | K | R | dR | Q | W | R | dR | CONH2 |
| 141 | 90 | H2N | dR | K | K | R | dR | Q | R | W | dR | CONH2 |
| 142 | 91 | H2N | dR | Y | K | R | dR | Q | R | R | dR | CONH2 |
| 143 | 92 | H2N | dR | K | Y | R | dR | Q | R | R | dR | CONH2 |
| 144 | 93 | H2N | dR | K | K | Y | dR | Q | R | R | dR | CONH2 |
| 145 | 94 | H2N | dR | K | K | R | dR | Y | R | R | dR | CONH2 |
| 146 | 95 | H2N | dR | K | K | R | dR | Q | Y | R | dR | CONH2 |
| 147 | 96 | H2N | dR | K | K | R | dR | Q | R | Y | dR | CONH2 |

In the above table D amino acids are indicated by a small "d" prior to the respective amino acid residue (e.g. dR=D-Arg).

For a few sequences synthesis failed in the first approach unfortunately due to technical reasons. These sequences are abbreviated in FIG. 6 as 1, 2, 3, 4, 5, 6, 7, 8, 43, 52, 53, 54, 55, 56, 57, 85, 86, 87, 88, 89, and 90. However, the remaining sequences were used in the internalization experiments.

The results are shown in FIG. 6.

As can be seen in FIG. 6, after 24 hours incubation, all transporters with the consensus sequence rXXXrXXXr (SEQ ID NO: 31) showed a higher internalization capability than the L-TAT transporter (SEQ ID NO: 43). Hela cells were incubated 24 hours in 96 well plate with 10 mM of the r3-L-TAT-derived transporters. The cells were then washed twice with an acidic buffer (0.2M Glycin, 0.15M NaCl, pH 3.0) and twice with PBS. Cells were broken by the addition of RIPA lysis buffer. The relative amount of internalized peptide was then determined by reading the fluorescence intensity (Fusion Alpha plate reader; PerkinElmer) of each extract followed by background subtraction As can be seen in FIG. 6, one positions appears to be critical for highest transporter activity and for improved kinetics of transport activity: Y in position 2 (peptide N°91 corresponding to SEQ ID NO: 142).

The conclusion of this experiment is as follows:

After 24 hours incubation, all transporters with the consensus sequence rXXXrXXXr (SEQ ID NO: 31) (see Table 2 for a selection of possible sequences) showed a higher internalization capability than the L-TAT transporter (SEQ ID NO: 43) (FIG. 6). Those results fully validate the consensus sequence rXXXrXXXr (SEQ ID NO: 31).

One position is critical for highest transporter activity and (FIG. 6): Y in position 2 (sequence 91 corresponding to SEQ ID NO: 142).

Accordingly, such TAT derived sequences as shown in Table 4 are preferred, which exhibit an Y in position 2, particularly when the sequence exhibits 9 aa and has the consensus sequence rXXXrXXXr (SEQ ID NO: 31).

Example 4

Measurement of Cytokine and Chemokine Release

In the following the procedure will be set forth describing how the released amount of several human cytokines after ligand induced secretion from human cells (Blood, WBC, PBMC, purified primary lymphocytes, cell lines, . . . ) was measured.

The technique used is a Sandwich ELISA, which allows measuring the amount of antigen between two layers of antibodies (i.e. capture and detection antibody). The antigen to be measured must contain at least two antigenic sites capable of binding to antibody, since at least two antibodies act in the sandwich. Either monoclonal or polyclonal antibodies can be used as the capture and detection antibodies in Sandwich ELISA systems. Monoclonal antibodies recognize a single epitope that allows fine detection and quantification of small differences in antigen. A polyclonal is often used as the capture antibody to pull down as much of the antigen as possible.

The advantage of Sandwich ELISA is that the sample does not have to be purified before analysis, and the assay can be very sensitive (up to 2 to 5 times more sensitive than direct or indirect).

The method may be used to determine the effect of the JNK inhibitors of the present invention in vitro/cell culture. At non toxic doses, compound efficacy is indicated by the decrease of the cytokine levels (the variation of optical density (absorbance at 450 nm)) as compared to non-treated samples and is monitored by ELISA. Results are express in ng/ml.

4.1 Material
- 96 well plate:
  - for collecting the supernatants (Ref 82.1581, Sarstedt)
  - for ELISA (F96 maxisorp, Ref 442404, Nunc)
- TopSeal-A: 96 well microplate seals (Ref 600585, PerkinElmer).
- ELISA reagent
  - Coating buffer ELISA: 0.1M NaCarbonate pH 9.5 (=7.13 g $NaHCO_3$ (ref 71627, Fluka)+1.59 g $Na_2CO_3$ (ref 71345, Fluka) in 1 liter H2O, pH to 9.5 with NaOH concentrated)
  - Wash buffer ELISA: PBS 1×+0.01% Tween20. Prepare 1 liter PBS 1× (PBS10×: ref 70011, GIBCO) and add 100 ul of Tween20 (ref P1379, Sigma) slowly while mixing with magnetic agitator)
  - Assay diluent: PBS 1×+10% FBS (Ref A15-151, PAA, decomplemented at 56° C., 30 min).
  - DAKO TMB (ref S1599, DAKO): commercial substrate solution
  - Stop Solution: 1M $H_3PO_4$ (→ for 200 ml=177 ml $H_2O$+ 23 ml $H_3PO_4$ 85% (ref 345245, Aldrich).
- ELISA Kit (reagent for 20 plates)
  - IFN-γ: Human IFN– ELISA set, BD OptEIA™ (ref 555142, DB).
  - IL-1β: Human IL-1 ELISA set II, BD OptEIA™ (ref 557953, BD)
  - IL-10: Human IL-10 ELISA set II, BD OptEIA™ (ref 555157, DB).
  - IL-12: Human IL-12 (p70) ELISA set, BD OptEIA™ (ref 555183, DB).
  - IL-15: Human IL-15 ELISA Set, BD OptEIA™ (ref 559268, DB).
  - IL-2: Human IL-2 ELISA set, BD OptEIA™ (ref 555190, DB).
  - IL-4: Human IL-4 ELISA set, BD OptEIA™ (ref 555194, DB).
  - IL-5: Human IL-5 ELISA set, BD OptEIA™ (ref 555202, DB).
  - IL-6: Human IL-6 ELISA setl, BD OptEIA™ (ref 555220, DB).
  - IL-8: Human IL-8 ELISA set, BD OptEIA™ (ref 555244, DB).
  - MCP-1: Human MCP-1 ELISA set, BD OptEIA™ (ref 555179, BD)
  - TNF-α: Kit human TNF ELISA set, BD OptEIA™ (ref 555212, DB).
- Absorbance reading: The absorbance was read on the Fusion Alpha Plate reader (Perkin Elmer).
- Repeating pipettes, digital pipettes or multichannel pipettes.

4.2 Method

Preparation of the Samples

The samples are culture medium supernatant from cultured human cells (typically whole blood, WBC, PBMC, Purified subtype of WBC, cancerous cell lines). Remove any particulate material by centrifugation (400 g 5 min 4° C.) and assay immediately or store samples at −20° C. Avoid repeated freeze-thaw cycles. One hour before using, defrost the samples on ice and centrifuge them. At step 11, dilute the samples in assay diluent directly into the plate (add first assay diluent, then the samples and pipette up and down):

Preparation of Standard

After warming lyophilized standard to room temperature, carefully open vial to avoid loss of material. Reconstitute lyophilized standard with the proposed volume of deionized water to yield a stock standard. Allow the standard to equilibrate for at least 15 minutes before making dilutions. Vortex gently to mix. After reconstitution, immediately aliquot standard stock in polypropylene vials at 50 µl per vial and freeze at −20° C. for up to 6 months. If necessary, store at 2-8° C. for up to 8 hours prior to aliquotting/freezing. Do not leave reconstituted standard at room temperature.

Immediately before use, prepare a ten point standard curve using 2-fold serial dilutions in reagent Diluent. A high standard of 4000 µg/ml is recommended.

Preparation of Detector Mix

One-step incubation of Biotin/SAv reagents. Add required volume of Detection Antibody to Assay Diluent. Within 15 minutes prior to use, add required quantity of Enzyme Reagent, vortex or mix well. For recommended dilutions, see lot-specific Instruction/Analysis Certificate. Discard any remaining Working Detector after use.

Coating with Capture Antibody

1. Coat the wells of a PVC microtiter plate with 100 µL per well of Capture Antibody diluted in Coating Buffer. For recommended antibody coating dilution, see lot-specific Instruction/Analysis Certificate.
2. Cover the plate with an adhesive plastic and incubate overnight at 4° C.
3. Remove the coating solution and wash the plate by filling the wells with 150 µl wash buffer.
4. The solutions or washes are removed by flicking the plate over a sink.
5. Repeat the process two times for a total of three washes.
6. After the last wash, remove any remaining wash buffer by patting the plate on a paper towel.

Blocking

7. Block the remaining protein-binding sites in the coated wells by adding 100 µl reagent Diluent per well.
8. Cover the plate with an adhesive plastic and incubate for 1 h at room temperature.
9. During the incubation, start preparing the standard.

Adding Samples

10. Do one wash as in step 3 with 150 µl of wash buffer. The plates are now ready for sample addition.
11. Add 50 µl of appropriately diluted samples in assay diluent to each well. For accurate quantitative results, always compare signal of unknown samples against those of a standard curve. Standards (triplicates) and blank must be run with each cytokine to ensure accuracy.
12. Cover the plate with an adhesive plastic and incubate for 2 h at room temperature.

Incubation with Detection Antibody and Secondary Antibody

13. Wash the plate four times with 150 µl wash buffer like step 3.
14. Add 50 µl of detector MIX (detection antibody+Secondary Streptavidin-HRP antibody in assay diluent) to each well at recommended dilutions (see lot-specific Instruction/Analysis Certificate).
15. Cover the plate with an adhesive plastic and incubate for 1 h at room temperature light protect.

16. Wash the plate six times with 150 μl wash buffer as in step 3.
17. Add 50 μl DAKO TMB solution to each well, incubate for 15-20 min at room temperature, in the dark, not sealed.
18. Add 50 μl of stop solution to each well. Gently tap the plate to ensure thorough mixing.
19. Mix the plate 5 min at 500 rpm on a plate mixer.
20. Read the optical density at 450 nm. (Program: Cytokine_ELISA on Fusion Alpha Plate reader).

Data Analysis

Average the triplicate readings for each standard control and each sample. Subtract the average zero standard optical density (O.D). Create a standard curve plotting the log of the cytokine concentration versus the log of the O.D and the best fit line can be determined by regression analysis. If samples have been diluted, the concentration read from the standard curve must be multiplied by the dilution factor. A standard curve should be generated for each set of samples assayed. The outliers data were avoided using Grugg's test. Then the data which weren't in the interval of two times the SD, were discard. The independent experiments are taken into account if the positive control showed data as previously observed. The independent experiments are pooled (N>3).

The data are presented in pg/ml of cytokine release or in %, compared to the induced condition without inhibitor treatment.

Example 5

THP1 Differentiation—Stimulation for Cytokine Release

In the following the procedure will be set forth describing how cytokine production from human PMA differentiated THP1 cells challenged by LPS for 6 h was induced in order to test the ability of JNK inhibitors of the present invention, in particular of a JNK inhibitor with SEQ ID NO: 172, to reduce stimulation-induced cytokine release. THP1 cells were stimulated ex-vivo by different ligands for the readout of cytokine release. At non toxic doses, JNK inhibitor efficacy is indicated by the decrease of the cytokine levels as compared to non-treated samples and is monitored by ELISA. The toxicity of the compound are evaluated by the reduction of a tretazolium salt (MTS) to formazan, giving a purple colour.

Procedure:
a. Material
Cell Line: THP-1 (Ref TIB-202, ATCC, lot 57731475)
Culture medium, reagent and plates
RPMI (Ref 21875-091, Invitrogen) complemented with:
10% FBS (Ref A15-151, PAA): decomplemented at 56° C., 30 min.
10 mM Hepes (Ref H0887, Sigma)
50 M-mercaptoethanol (Ref 63690, Fluka: stock at 14.3M): add 560 l of 50 mM aliquots in PBS stocked at −20° C.)
1 mM Sodium Pyruvate (Ref 58636, Sigma)
Penicilline (100 unit/ml)/Streptomycine (100 g/ml) (Ref P4333, Sigma)
The RPMI medium is then filtrated with a 0.22 M filter (Ref SCGPU05RE, Millipore).
PBS 10× (Ref 70011, Invitrogen): diluted to 1× with sterile $H_2O$
DMSO: Ref 41444, Fluka
PMA (phorbol 12-myristate 13-acetate, Ref P1585, Sigma, concentration 1 mM=616.8 ug/ml in DMSO at −20° C.). Use directly at a final concentration of 100 nM in RPMI (1 ul in 10 ml of medium).
LPS ultrapure (Lipopolysaccharide, Ref tlrl-eklps, Invivogen, concentration 5 mg/ml): Stock solution of LPS: 3 g/ml in PBS at 4° C. Use directly to prepare a 4× concentrated solution of 40 ng/ml in RPMI medium (min 1800 l/plate; for 5 plates: 125 l of LPS 3 g/ml+9250 l RPMI).
96 well plate:
for adherent cell culture (Ref 167008, Nunc)
for collecting the supernatants (Ref 82.1581, Sarstedt)
for ELISA (F96 maxisorp, Ref 442404, Nunc)
Coating solutions: poly-D-lysine (Ref P9011, Sigma): 25 g/ml final diluted in PBS 1×
ELISA reagent and kits
Coating buffer ELISA: 0.1 M NaCarbonate pH 9.5 (=7.13 g $NaHCO_3$ (ref 71627, Fluka)+1.59 g $Na_2CO_3$ (ref 71345, Fluka) in 1 liter H2O, pH to 9.5 with NaOH concentrated)
Wash buffer ELISA: PBS 1X+0.01% Tween20 (ref P1379, Sigma, lot 094K0052) (=prepare 1 liter PBS 1× and add 100 ul of Tween20 slowly while mixing with magnetic agitator)
Assay diluent: PBS 1X+10% FBS (Ref A15-151, PAA, decomplemented at 56° C., 30 min).
DAKO TMB (ref S1599, DAKO): commercial substrate solution
Stop Solution: 1M $H_3PO_4$ (→ for 200 ml=177 ml $H_2O$+23 ml $H_3PO_4$ 85% (ref 345245, Aldrich).
TNF−: Kit human TNF ELISA set, BD OptEIA (ref 555212, DB).
Cytotoxicity measurement: CellTiter 96 reagent (ref G3581, Promega)
Control compound: 5P600125 (ref ALX-270-339-M025, Alexis, concentration: 20 mM DMSO)
Absorbance reading: The absorbance was read on the Fusion Alpha Plate reader (Perkin Elmer).
Repeating pipettes, digital pipettes or multichannel pipettes.
TopSeal-A: 96 well microplate seals (Ref 600585, PerkinElmer).

b. Method

Well Coating

The plates had been coated with 200 l of poly D-Lysine (1×) and incubated 2 hours at 37° C., $CO_2$ 5% and 100% relative humidity.

Cell Plating

After 2 hours the wells were washed twice with 200 l PBS 1× (use immediately or leave with 200 l of PBS 1× at 37° C. till use, but no more than 3 days).

The cells were counted. The desired number of cells was taken and resuspended in the amount of media necessary to get a dilution of 1,000,000 cells/ml. 100 nM of PMA was added to induce the differentiation of the THP1 from suspension monocytes to adherent macrophages. The cells were plated into the wells in 100 l medium at plating densities of 100,000 cells/well. After inoculation, the plates were incubated at 37° C., 5% CO2 and 100% relative humidity 3 days to let them differentiate, prior to the addition of experimental drugs.

Cell Treatment

After 3 days, the adherent cells were observed with the microscope. The media containing PMA was aspirated and replaced by 100 l of fresh RPMI media without PMA (no washing step with PBS 1×).

Experimental drug were prepared at the concentration of 10 mM in H$_2$O or DMSO and stored at −80° C. Prior to each daily use, one aliquot of JNK inhibitor was defrost and diluted to reach a 4× concentrated solution (120 M) in RPMI medium and then to the desired concentration in RPMI. The SP600125 was diluted to reach a 4× concentrated solution (40 M) in RPMI medium and then to the desired concentration in RPMI containing 0.8% DMSO.

The plates were treated with 50 l of medium or a solution of 4× the final desired drug concentration (0, 100 nM, 1, 3, 10 or 30 M final for JNK compound or at 0, 10, 100 nM, 1, 3 or 10 M final for the SP600125 positive control). Following drug addition, the plates were incubated for an additional 1 h at 37° C., 5% CO$_2$ and 100% relative humidity.

After 1 hours, the secretion of TNF was induced by the addition of 50 l of a 4× concentrated dilution of LPS ultrapure (3 ng/ml final).

Assay

After 6 hours, 100 l of the supernatant were transferred to new 96 well plates. Those plates were sealed and stored at −20° till the analysis by ELISA (e.g. see example 4) of the secretion of the cytokines.

The cytotoxic effect of the compounds was evaluated by MTS absorbance (e.g. see example 4) and cells were observed using an inverted microscope (Axiovert 40 CFL; Zeiss; 10×).

Data Analysis

Analyses of the data are performed as indicated in the ELISA (see example 4). Briefly, for ELISA: Average the triplicate readings for each standard control and each sample. Subtract the average zero standard optical density (O.D). Create a standard curve plotting the log of the cytokine concentration versus the log of the O.D and the best fit line can be determined by regression analysis. If samples have been diluted, the concentration read from the standard curve must be multiplied by the dilution factor. A standard curve should be generated for each set of samples assayed. The outliers data were avoid using Grugg's test. Then the data which weren't in the interval of two times the SD, were discard. The independent experiments are taken into account if the positive control showed data as previously observed. The independent experiments are pooled (N>3).

For the Cytotoxicity effect evaluation: on each plate of each independent experiment taken into account for the cytokine release experiment analysis, the average of the absorbance of the medium alone was considerate as the background and subtracted to each absorbance value. The average of triplicate of the non treated cells of each compound was considerate as the 100% viability. The average of triplicate of each compound was normalized by its 100%. The outliers data were avoid using Grugg's test. Then the data which weren't in the interval of two times the SD, were discard. The independent experiments are pooled (N>3).

All statistical comparisons of conditions were performed by the GraphPad Prism4 software with the following test: One way ANOVA test followed by a Tukey's Multiple Comparison Test. P<0.05 was considerate as significant.

Example 6

JNK Inhibitor of SEQ ID NO: 172 and TNFα Release in Primary Rat or Human Whole Blood Cells Whole blood is collected from anesthetized rat or human healthy volunteers using a venipuncture connected to a prelabeled vacuum tube containing sodium citrate. Tubes are gently mixed by inversion 7-8 times; and are then kept at RT until stimulation. JNK inhibitor of SEQ ID NO: 172 is prepared 6 times concentrated in PBS, and 30 μl/well of mix is added into 96-well plate. Whole blood is diluted by 1:2 in PBS and 120 μl of diluted blood is added in each well where either PBS alone or JNK inhibitor of SEQ ID NO: 172 has been previously added. Whole blood is incubated at 37° C.; 85 rpm (Stuart Orbital incubator SI500) for 60 min. Activators (LPS) are the prepared, 30 μl/well of LPS, 6 times concentrated. After 60 min incubation, LPS is added to the blood, blood is mixed by pipetting up and down, and then kept for 4 h under agitation (85 rpm), at 37° C. After the 4 h incubation, the plates are centrifuged at about 770 g, 4° C. for 15 min in a pre-cooled centrifuge. Supernatants are finally collected and kept at −20° C. until cytokine measurement. Cytokine (IL-6, IL-2, IFNγ and TNFα) were then measured using standard Elisa kits (e.g. from R&D Systems: DuoSet Elisas; or from BD Biosciences: BD Opteia Set Elisa). Results are expressed as pg/ml of supernatant of the measured cytokine.

A similar experiment was conducted with PMA+ionomycin instead of LPS as activator/stimulant.

Example 7

Half-Life of Specific JNK Inhibitors Disclosed Herein

The JNK inhibitors with the sequence of SEQ ID NOs: 196, 197, and 172 (0.1 mM final concentration) were digested in human serum (10 and 50% in PBS 1×). The experiment was performed as described by Tugyi et al. (Proc Natl Acad Sci USA, 2005, 413-418). The remaining intact peptide was quantified by UPLC-MS. Stability was assessed for SEQ ID NOs: 196, 197, and 172 identically but in two separate assays. While the JNK inhibitor with SEQ ID NO: 196 was totally degraded into amino acids residues within 6 hours, the JNK inhibitor with SEQ ID NO: 172 was completely degraded only after 14 days. The JNK inhibitor with SEQ ID NO: 197 was still stable after 30 days.

Example 8

Dose-Dependent Inhibition by JNK Inhibitor with Sequence of SEQ ID NO: 172 of CD3/CD28-Induced IL-2 Release in Rat Primary T-Cells Control animal were sacrificed, lymph nodes (LN) were harvested and kept in complete RPMI medium. LN were smashed with complete RPMI on 70 μm filter using a 5 ml piston. A few drops of media were added to keep strainer wet. Cells were centrifuged for 7 min at 450 g and 4° c. Pellet was resuspended in 5 ml fresh medium. Cells were passed again through cell strainer. An aliquot of cells was counted, while cells were centrifuged again 10 min at 1400 rpm and 4° c. Cells were resupended in MACS buffer (80 μl of MACS buffer per 10$^7$ cells). 10 μl of anti-rat MHC microbeads were added per 10 million cells, cells were incubated for 15 min at 4°-8° C. Cells were washed with 15 ml MACS buffer and centrifuge for 7 min at 700 g and 4° C. Pellet was resuspended in 500 μl MACS buffer per 10$^8$ cells. One LS column was placed in the magnetic field of the MACS separator per animal. Column was first rinsed with 3 ml of MACS buffer. One tube was placed below the column in ice to collect cells=T cells (negative selection so we collect what is eluted). Cell suspension was added and elute was collected on ice. Column was washed 3 times with 3 mL MACS buffer. Eluted T cells were centrifuges for 7 min at 700 g and 4° C. Resuspended cells were counted and plated at density of 200000 cells/well in 100 μl of complete medium. Plates were precoated the day before experiment with 2 μg/mL of CD3 antibody, and the day of experiment plates were washed three times with PBS. Cells were treated with 100 μl of (poly-)peptide JNK inhibitor (SEQ ID NO: 172), two times concentrated for 1 h before ligand activation. After 1 h of pretreatment with (poly-)peptide JNK inhibitor (SEQ ID NO: 172), cells were then stimulated with 2 μg/mL of anti CD28 antibody for 24 h. After 24 h of stimulation, supernatant were collected and stored at −20° C. until analysis. Cytokines were then measured using standard Elisa kits. Results are expressed as pg/ml of supernatant of the measured cytokine.

In a further experiment, essentially the same protocol as set forth above was used, but in addition to the (poly-)peptide JNK inhibitors with SEQ ID NO: 172, JNK inhibitors with the sequence of SEQ ID NO: 197 and the drug molecule SP600125 were also tested thus allowing to compare the effects of these inhibitors on the inhibition of CD3/CD28-induced IL-2 release.

Example 9

JNK Inhibitor and TNFα/IL-2 Release in Human Whole Blood

Whole blood from human healthy volunteers was collected using a venipuncture connected to a pre-labeled vacuum tube containing sodium citrate. Tubes are gently mixed by inversion 7-8 times; and are then kept at RT until stimulation. 350 μl of RPMI+P/S were added into 1.2 ml-96-well plate. 10 times concentrated of SEQ ID NO: 172 was prepared in RPMI+P/S (50 μl per well). 50 μl was added into 1.2 ml-96 well plates. 50 μl of whole blood was then added in each well where either medium alone or JNK inhibitor has been previously added. Whole blood was incubated at 37° C., 5% CO2 for 60 min. 50 μl/well of ligands diluted in RPMI+P/S was prepared, corresponding to the final dilution 10 times concentrated. After 60 min of incubation, ligand was added; wells were then mixed by pipetting up and down the blood. Whole blood was incubated for 3 days at 37° C. (wells were mixed by pipetting each well up and down once per day). At the end of incubation, plates were mixed and then centrifuged at 2500 rpm, 4° C. for 15 min in a pre-cooled centrifuge. Cytokine were then measured using standard Elisa kits. Results are expressed as pg/ml of supernatant of the measured cytokine.

A similar experiment was carried out with slight modifications. In the case of CD3/CD8 stimulation, CD3 antibody was coated at 2 μg/mL in PBS overnight at 4° C. The day of experiment, wells were washed three times with PBS and left in PBS until use at 37° C. CD28 antibody was added 1 h after SEQ ID NO: 172 at final concentration of 2 μg/mL; supernatants were collected after 3 days of stimulation.

The invention claimed is:

1. A JNK inhibitor comprising an inhibitory polypeptide sequence sharing at least 80% sequence identity with SEQ ID NO: 8.

2. The JNK inhibitor according to claim 1, wherein the inhibitory polypeptide sequence is SEQ ID NO: 8.

3. The JNK inhibitor of claim 1, wherein the inhibitory polypeptide sequence sharing at least 80% sequence identity with SEQ ID NOs: 8 has a D-Ala residue at a position corresponding to position 6 of SEQ ID NO: 8.

4. The JNK inhibitor of claim 1, wherein the JNK inhibitor further comprises a transporter sequence.

5. The JNK inhibitor according to claim 4, wherein the inhibitory polypeptide sequence and the transporter sequence overlap.

6. The JNK inhibitor according to claim 4, wherein the transporter sequence comprises a sequence of alternating D- and L-amino acids according to anyone of SEQ ID NOs: 28-30.

7. The JNK inhibitor of claim 4, wherein said transporter sequence is SEQ ID NO: 46.

8. The JNK inhibitor of claim 4, wherein said transporter sequence is selected from any one of SEQ ID NOs: 31-34, 46, 47 and 52-151.

9. The JNK inhibitor of claim 4, wherein said transporter sequence is positioned directly N-terminal or directly C-terminal of the inhibitory polypeptide sequence.

10. The JNK inhibitor of claim 4, wherein the JNK inhibitor comprises a sequence selected from SEQ ID NOs: 171-173, 176-177 and 182-187.

11. The JNK inhibitor of claim 4, wherein the JNK inhibitor comprises the sequence of SEQ ID NO: 172.

12. The JNK inhibitor of claim 1, wherein the L arginine (R) residue at position 4 and the L-leucine (L) residue at positions 8 and 10 of SEQ ID NO: 8 cannot be changed, and wherein at least one other amino acid of the inhibitory polypeptide sequence is in the D conformation.

13. The JNK inhibitor of claim 12, wherein the amino acid corresponding to position 1 of SEQ ID NO: 8 is selected from the group consisting of R, P, Q and r, the amino acid corresponding to position 2 of SEQ ID NO: 8 is selected from the group consisting of R, P, G and r, the amino acid corresponding to position 3 of SEQ ID NO: 8 is selected from the group consisting of K, R, k and r, the amino acid corresponding to position 5 of SEQ ID NO: 8 is selected from the group consisting of P and K, the amino acid corresponding to position 6 of SEQ ID NO: 8 is absent or is selected from the group consisting of T, a, s, q, k, the amino acid corresponding to position 7 of SEQ ID NO: 8 is selected from the group consisting of T, D and A, the amino acid corresponding to position 9 of SEQ ID NO: 8 is selected from the group consisting of N, n, r and K, and the amino acid corresponding to position 11 of SEQ ID NO: 8 is selected from the group consisting of F, f and w, wherein an amino acid residue in a capital letter indicates an L-amino acid, and an amino acid residue in a lower case letter indicates a D amino acid residue.

14. The JNK inhibitor of claim 1, wherein the inhibitory polypeptide sequence sharing at least 80% sequence identity with SEQ ID NOs: 8 has a D-Lys residue at a position corresponding to position 3 of SEQ ID NO: 8.

15. The JNK inhibitor of claim 1, wherein the inhibitory polypeptide sequence sharing at least 80% sequence identity with SEQ ID NOs: 8 has a D-Phe residue at a position corresponding to position 11 of SEQ ID NO: 8.

* * * * *